US007829685B2

(12) United States Patent
Watanabe et al.

(10) Patent No.: US 7,829,685 B2
(45) Date of Patent: Nov. 9, 2010

(54) REGULATION OF KINASE, REGULATED IN COPD KINASE (RC KINASE)

(75) Inventors: Shinichi Watanabe, Nara (JP); Jeffrey A. Encinas, San Diego, CA (US); Shinichi Kondo, Nara (JP); Kevin Bacon, San Diego, CA (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 728 days.

(21) Appl. No.: 10/561,570

(22) PCT Filed: Jun. 16, 2004

(86) PCT No.: PCT/EP2004/006474

§ 371 (c)(1), (2), (4) Date: Sep. 11, 2007

(87) PCT Pub. No.: WO2005/001083

PCT Pub. Date: Jan. 6, 2005

(65) Prior Publication Data

US 2008/0261903 A1 Oct. 23, 2008

(30) Foreign Application Priority Data

Jun. 27, 2003 (EP) .................................. 03014688
Mar. 2, 2004 (EP) .................................. 04004818

(51) Int. Cl.
*C07H 21/04* (2006.01)
*C12N 5/00* (2006.01)
*C12N 5/02* (2006.01)
*A61K 48/00* (2006.01)

(52) U.S. Cl. .................... 536/23.2; 536/23.1; 536/23.5; 435/325; 424/93.2; 424/93.21

(58) Field of Classification Search ................ 536/23.2, 536/23.1, 23.5; 435/325; 424/93.2, 93.21
See application file for complete search history.

(56) References Cited

U.S. PATENT DOCUMENTS

2003/0054529 A1 3/2003 Yan et al.

FOREIGN PATENT DOCUMENTS

WO WO02/33099 4/2002
WO WO 02090525 A2 * 11/2002
WO WO03/018786 3/2003
WO PCT/EP2004/006474 11/2004

OTHER PUBLICATIONS

Burgess et al., J. of Cell Bio., 111: 2129-2138 (1990).*
Lazar et al., Mol. & Cell. Bio., 8: 1247-1252 (1998).*
Alignment of SEQ ID No. 4 and 10 to WO 02/090525.*
Seffernick et al. J. Bacteriol. 183(8):2405-2410, 2001.*
GenBank Accession No. AK122935.
GenBank Accession No. AC016725.
Puchelle et al., 2001 "Chronic Obstructive Pulmonary Disease: An old Disease with Novel Concepts and Drug Strategies," *Trends in Pharmacological Sciences*, 22(10): 495-497.
Rahman Irfan, 2002 "Oxidative Stress and Gene Transcription in Asthma and Chronic Obstructive Pulmonary Disease: Antioxidant Therapeutic Targets," *Current Drug Targets—Inflammation and Allergy*, 1(3): 291-315.

* cited by examiner

*Primary Examiner*—Thaian N Ton
(74) *Attorney, Agent, or Firm*—Jones Day

(57) ABSTRACT

Reagents which regulate human RC Kinase activity and reagents which bind to human RC Kinase gene products can be used to regulate this protein for therapeutic effects. Such regulation is particularly useful for treating chronic obstructive pulmonary disease, asthma, cancer, and diseases in which cell signaling is defective.

12 Claims, 11 Drawing Sheets

Figure 1

| Rank | Acc. No. | Description | Fold upregulated |
|---|---|---|---|
| 1 | BI83334 | 603087960f1 Homo Sapiens cDNA, 5' End (GADD34) | 21.28 |
| 2 | NM_024833 | Hypothetical Protein FLJ23506 (FLJ23506), mRNA. Zinc Finger Protein | 15.35 |
| 3 | BG68092 | 602628721F1 Homo Sapiens cDNA, 5' End | 12.71 |
| 4 | AL11741 | Homo Sapiens mRNA; cDNA DKFZP434k0521 (From Clone DKFZP434k0521) | 11.15 |
| 5 | NM_000095 | Cartilage Oligomeric Matrix Protein (Pseudoachondroplasia, Epiphyseal Dysplasia 1, Multiple), mRNA. | 7.99 |
| 6 | NM_005672 | Prostate Stem Cell Antigen (PSCA), mRNA. | 7.53 |
| 7 | NM_005181 | Carbonic Anhydrase III, Muscle Specific (Ca3), mRNA. | 7.48 |
| 8 | NM_021870 | Fibrinogen, Gamma Polypeptide (FGG), Transcript Variant Gamma-b, mRNA. | 7.22 |
| 9 | AL05038 | Homo Sapiens mRNA; cDNA DKFZP564m2422 (From Clone DKFZP564m2422); Partial CDS | 6.96 |
| 10 | NM_013332 | Hypoxia-inducible Protein 2 (HIG2), mRNA. | 6.86 |
| 11 | NM_021992 | Thymosin, Beta, Identified in Neuroblastoma Cells (TMSNB), mRNA. | 6.22 |
| 12 | NM_002228 | V-jun Sarcoma Virus 17 Oncogene Homolog (Avian) (JUN), mRNA. | 5.97 |
| 13 | NM_021052 | H2a Histone Family, Member a (H2AFA), mRNA | 5.71 |
| 14 | NM_007021 | Decidual Protein Induced by Progesterone (DEPP), mRNA. | 5.62 |
| 15 | NM_001179 | ADP-ribosyltransferase 3 (ART3), mRNA. | 5.07 |
| 16 | AL13361 | Homo Sapiens mRNA; cDNA DKFZP434f1928 (From Clone DKFZP434f1928) | 4.81 |
| 17 | NM_005064 | Small Inducible Cytokine Subfamily a (Cys-cys), Member 23 (SCYA23), mRNA. | 4.70 |
| 18 | NM_025052 | Hypothetical Protein FLJ23074 (FLJ23074), mRNA. Putative Protein Kinase **RC Kinase fragment** | 4.58 |
| 19 | NM_000519 | Hemoglobin, Delta (HBD), mRNA. | 4.57 |
| 20 | NM_006145 | DNAJ (HSP40) Homolog, Subfmaily B, Member 1 (DNAJB1), mRNA. | 4.57 |

REGULATION OF KINASE, REGULATED IN COPD KINASE (RC KINASE)

This application is the National Stage of International Application No. PCT/EP2004/006474, filed Jun. 16, 2004, and claims priority from European Patent Application No. 03014688.0, filed Jun. 27, 2003, and European Patent Application No. 04004818.3, filed Mar. 2, 2004, the contents of which are incorporated by reference in their entireties.

TECHNICAL FIELD OF THE INVENTION

The invention relates to the area of regulation of kinase activity. More particularly, the invention relates to the regulation of a novel human kinase, Regulated in COPD Kinase (RC Kinase). The invention discloses that the gene of RC Kinase is overexpressed in COPD patients and is useful as a diagnostic marker and target for treatment. Methods are disclosed for predicting, diagnosing and prognosing as well as preventing and treating COPD with the use of RC Kinase. Methods are also disclosed for predicting, diagnosing and prognosing as well as preventing and treating other ailments in which RC Kinase is dysregulated or in which modulation or enhancement of the activity of RC Kinase can modify disease progression. Modulation of RC Kinase activity can affect disease status such as, COPD, asthma, cancer, Alzheimer's disease, inflammatory diseases, and cardiovascular diseases.

BACKGROUND OF THE INVENTION

Intracellular signaling regulates a variety of important biological functions. One common method used by cells to conduct signals is protein phosphorylation. In order to transmit signals, activated enzymes called protein kinases attach phosphate groups to downstream molecules in a signaling cascade and thereby, depending on the type of molecule, regulate their enzymatic activity, their subcellular localization, their interaction with other molecules, their shape, or their halflife. One important family of protein kinases involved in this type of signal transmission is the mitogen-activated protein kinases (MAPKs) (Widmann, C. et al., *Physiol Rev* 79(1):143-80, 1999). Because MAPKs are themselves regulated by phosphorylation, they are often members of complex phosphorelay systems within cells involving other kinases. For example a MAPK can be phosphorylated by MAPK kinases (MKKs), which in turn can be phosphorylated by MAPK kinase kinases (MKKKs). Such a phosphorelay system can serve to amplify a signal, determine the specificity of a signal, and allow regulation at different points in the signaling cascade. MAPKs, MKKs, and MKKKs have been found to play roles in a large variety to cellular activities, including gene expression, mitosis, proliferation, cell movement, metabolism, and programmed cell death. Because of the important functions of protein kinase family enzymes such as the MAPKs, MKKs, and MKKKs, there is a need in the art to identify new MAPK pathway kinases and methods of regulating these new kinases for therapeutic effects.

SUMMARY OF THE INVENTION

It is an object of the invention to provide reagents and methods of regulating a human RC Kinase. These and other objects of the invention are provided by one or more of the embodiments described below.

One embodiment of the invention is an isolated polynucleotide encoding a RC Kinase polypeptide and being selected from the group consisting of:

a) a polynucleotide encoding a RC Kinase polypeptide comprising an amino acid sequence selected from the group consisting of:
   amino acid sequences which are at least about 50% identical to
   the amino acid sequence shown in SEQ ID NO: 7, 8, 9, 10, 11, or 12; and
   the amino acid sequence shown in SEQ ID NO: 7, 8, 9, 10, 11, or 12.
b) a polynucleotide comprising the sequence of SEQ ID NO: 1, 2, 3, 4, 5, or 6;
c) a polynucleotide which hybridizes under stringent conditions to a polynucleotide specified in (a) and (b);
d) a polynucleotide the sequence of which deviates from the polynucleotide sequences specified in (a) to (c) due to the degeneration of the genetic code; and
e) a polynucleotide which represents a fragment, derivative or allelic variation of a polynucleotide sequence specified in (a) to (d).

Another embodiment of the invention is a substantially purified RC Kinase polypeptide encoded by a polynucleotide of the above.

The present invention further relates to novel preventive, predictive, diagnostic, prognostic and therapeutic compositions and uses for COPD. Since RC Kinase expression levels are increased in the disease state, its gene product is a particularly useful target for treatment methods as well as diagnostic and clinical monitoring methods.

The present invention further relates to novel preventive, predictive, diagnostic, prognostic and therapeutic compositions and uses for COPD based on derivatives, fragments, analogues and homologues of the RC Kinase gene.

The present invention further relates to methods for detecting the dysregulation of RC Kinase in COPD on the DNA and mRNA levels.

The present invention further relates to a method for the prediction, diagnosis or prognosis of COPD by the detection of RC Kinase gene or RC Kinase genomic nucleic acid sequence which is altered in COPD.

In one embodiment the expression of the RC Kinase gene can be detected with arrays.

In a further embodiment, the expression of the gene can be detected with bead based direct fluorescent readout techniques such as provided by Luminex corporation (U.S. Pat. No. 6,268,222).

In one embodiment, the invention pertains to a method of determining the phenotype of a cell or tissue, comprising detecting the differential expression, relative to a normal or untreated cell, of the polynucleotide comprising SEQ ID NO: 1, 2, 3, 4, 5, or 6, wherein the polynucleotide is differentially expressed by at least about 1.5 fold, at least about 2 fold or at least about 3 fold.

In yet another embodiment the invention provides the human genomic region on chromosome 2q21.3, specifically the genomic region found on the human genomic sequence contig with the Genbank accession number NT_005058, for use in prediction, diagnosis and prognosis as well as prevention and treatment of COPD. In particular not only the intragenic regions, but also intergenic regions, pseudogenes or non-transcribed genes of said chromosomal regions can be used for diagnostic, predictive, prognostic and preventive and therapeutic compositions and methods.

In yet another embodiment the invention provides methods of screening for agents which regulate the activity of a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6. A test compound is contacted with a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6. Binding of the test compound to the polypeptide is detected. A test compound which binds to the polypeptide is thereby identified as a potential therapeutic agent for the treatment of COPD.

In even another embodiment the invention provides another method of screening for agents which regulate the activity of a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6. A test compound is contacted with a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6. A biological activity mediated by the polypeptide is detected. A test compound which decreases the biological activity is thereby identified as a potential therapeutic agent for decreasing the activity of the polypeptide encoded by a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 in COPD. A test compound which increases the biological activity is thereby identified as a potential therapeutic agent for increasing the activity of the polypeptide encoded by the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 in COPD.

In another embodiment the invention provides a method of screening for agents which regulate the activity of a polynucleotide comprising the polynucleotide of SEQ ID NO: 1, 2, 3, 4, 5, or 6. A test compound is contacted with a polynucleotide comprising the polynucleotide of SEQ ID NO: 1, 2, 3, 4, 5, or 6. Binding of the test compound to the polynucleotide comprising the polynucleotide of SEQ ID NO: 1, 2, 3, 4, 5, or 6 is detected. A test compound which binds to the polynucleotide is thereby identified as a potential therapeutic agent for regulating the activity of a polynucleotide comprising the polynucleotide of SEQ ID NO: 1, 2, 3, 4, 5, or 6 in COPD.

The invention thus provides polypeptides if SEQ ID NO: 7, 8, 9, 10, 11, or 12 or a polypeptide encoded by a polynucleotide comprising the polynucleotide of SEQ ID NO: 1, 2, 3, 4, 5, or 6 which can be used to identify compounds which may act, for example, as regulators or modulators such as agonists and antagonists, partial agonists, inverse agonists, activators, co-activators and inhibitors of the polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6. Accordingly, the invention provides reagents and methods for regulating a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 in COPD. The regulation can be an up- or down regulation. Reagents that modulate the expression, stability or amount of a polynucleotide comprising a polynucleotide of SEQ ID NO: 1, 2, 3, 4, 5, or 6 or the activity of the polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 can be a protein, a peptide, a peptidomimetic, a nucleic acid, a nucleic acid analogue (e.g. peptide nucleic acid, locked nucleic acid) or a small molecule. Methods that modulate the expression, stability or amount of a polynucleotide comprising a polynucleotide of SEQ ID NO: 1, 2, 3, 4, 5, or 6 or the activity of the polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 can be gene replacement therapies, antisense, ribozyme, RNA interference and triplex nucleic acid approaches.

In one embodiment of the invention provides antibodies which specifically bind to a full-length or partial polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 or a polynucleotide comprising the polynucleotide of SEQ ID NO: 1, 2, 3, 4, 5, or 6 for use in prediction, prevention, diagnosis, prognosis and treatment of COPD.

Yet another embodiment of the invention is the use of a reagent which specifically binds to a polynucleotide comprising a polynucleotide of SEQ ID NO: 1, 2, 3, 4, 5, or 6 or a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 in the preparation of a medicament for the treatment of COPD.

Still another embodiment is the use of a reagent that modulates the activity or stability of a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6 or the expression, amount or stability of a polynucleotide comprising a polynucleotide of SEQ ID NO: 1, 2, 3, 4, 5, or 6 in the preparation of a medicament for the treatment of COPD.

Still another embodiment of the invention is a pharmaceutical composition which includes a reagent which specifically binds to a polynucleotide comprising the polynucleotide of SEQ ID NO: 1, 2, 3, 4, 5, or 6 or a polypeptide comprising the polypeptide of SEQ ID NO: 7, 8, 9, 10, 11, or 12 or a polypeptide encoded by a polynucleotide comprising the polynucleotide of SEQ ID NO: 1, 2, 3, 4, 5, or 6, and a pharmaceutically acceptable carrier.

Yet another embodiment of the invention is a pharmaceutical composition including a polynucleotide comprising the polynucleotide of SEQ ID NO: 1, 2, 3, 4, 5, or 6 or encoding a polypeptide comprising the polypeptide of SEQ ID NO: 7, 8, 9, 10, 11, or 12.

In one embodiment, a reagent which alters the level of expression in a cell of a polynucleotide comprising the polynucleotide of SEQ ID NO: 1, 2, 3, 4, 5, or 6 or encoding a polypeptide comprising the polypeptide of SEQ ID NO: 7, 8, 9, 10, 11, or 12, or a sequence complementary thereto, is identified by providing a cell, treating the cell with a test reagent, determining the level of expression in the cell of a polynucleotide comprising the polynucleotide of SEQ ID NO: 1, 2, 3, 4, 5, or 6 or encoding a polypeptide comprising the polypeptide of SEQ ID NO: 7, 8, 9, 10, 11, or 12 or a sequence complementary thereto, and comparing the level of expression of the polynucleotide in the treated cell with the level of expression of the polynucleotide in an untreated cell, wherein a change in the level of expression of the polynucleotide in the treated cell relative to the level of expression of the polynucleotide in the untreated cell is indicative of an agent which alters the level of expression of the polynucleotide in a cell.

The invention further provides a pharmaceutical composition comprising a reagent identified by this method.

Another embodiment of the invention is a pharmaceutical composition which includes a polypeptide comprising the polypeptide of SEQ ID NO: 7, 8, 9, 10, 11, or 12 or which is encoded by a polynucleotide comprising the polynucleotide of SEQ ID NO: 1, 2, 3, 4, 5, or 6.

A further embodiment of the invention is a pharmaceutical composition comprising a polynucleotide including a sequence which hybridizes under stringent conditions to a polynucleotide comprising a polynucleotide of SEQ ID NO: 1, 2, 3, 4, 5, or 6 and encoding a polypeptide exhibiting the same biological function as RC Kinase, or encoding a polypeptide of SEQ ID NO: 7, 8, 9, 10, 11, or 12. Pharmaceutical compositions, useful in the present invention may further include fusion proteins comprising a polypeptide comprising a polynucleotide of SEQ ID NO: 1, 2, 3, 4, 5, or 6, or a fragment thereof, antibodies, or antibody fragments

BRIEF DESCRIPTION OF THE DRAWINGS

FIG. 1 shows the top 20 upregulated genes in lung tissue from COPD patients as determined by microarray analysis. The fold increase in expression of these genes compared with the average expression in lung tissue from normal subjects is shown in the far right column. RC Kinase is shown to have an increased expression of 4.58 fold in COPD compared to normal, and is ranked $18^{th}$ among the approximately 10,000 genes represented on the microarray.

DETAILED DESCRIPTION OF THE INVENTION

Figure 2:
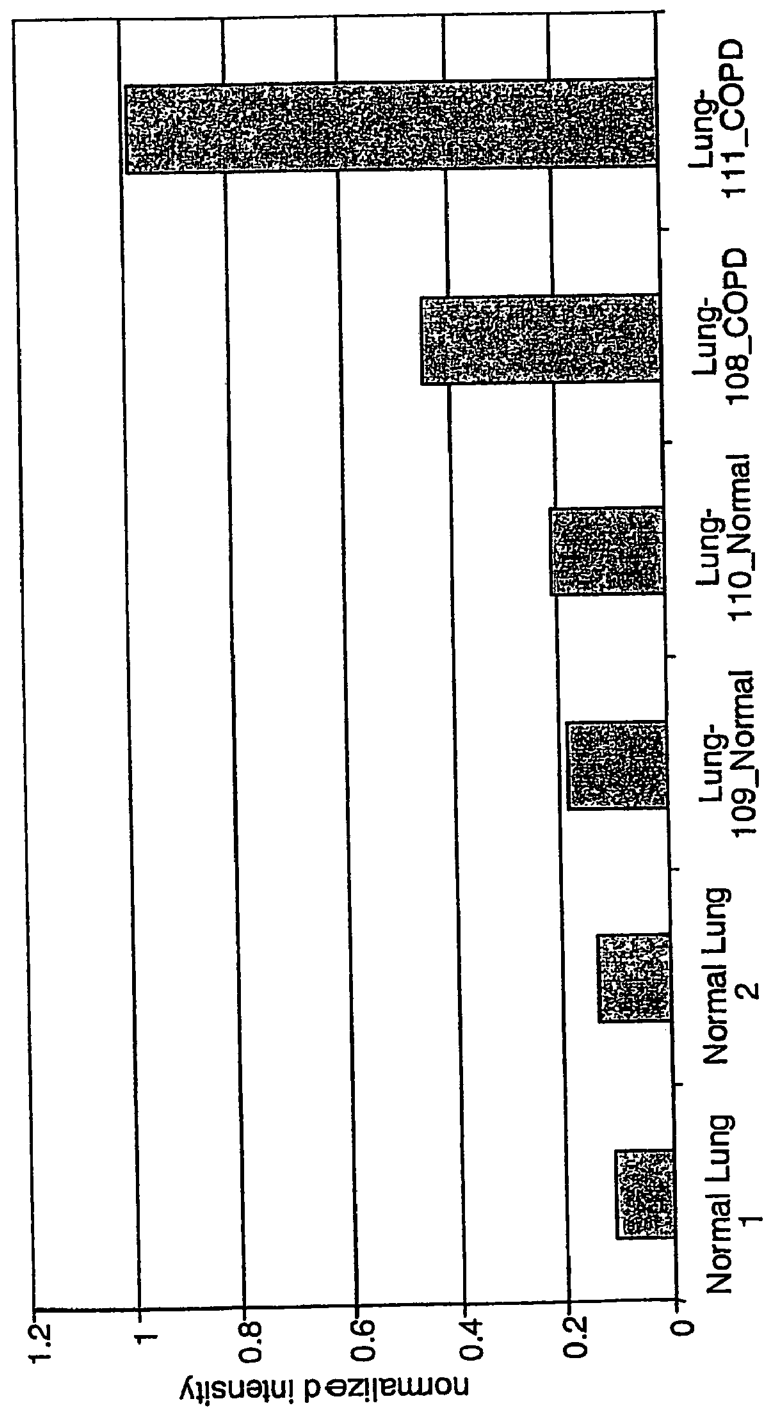
FIG. 2 shows the relative expression levels for human RC Kinase obtained from microarray experiments using various normal and COPD lung samples.

"RC Kinase" as used herein refers to the polypeptide of SEQ ID NO 7, 8, 9, 10, 11 or 12, as well as it derivatives, fragments, analogs, and homologues thereof, or the polypeptides encoded by the polynucleotide of SEQ ID NO: 1 as well as derivatives, fragments, analogs and homologues thereof.

SEQ ID NO: 1 shows variant 1 of the DNA-sequence encoding an RC Kinase polypeptide. This variant is 3719 bp in length, with an open reading frame extending from bases 1-3679 of the sequence. SEQ ID NO: 2 shows variant 2 of the DNA-sequence encoding an RC Kinase polypeptide. This variant is 3338 bp in length, with an open reading frame extending from bases 1-3243 of the sequence. SEQ ID NO: 3 shows variant 3 of the DNA-sequence encoding an RC Kinase polypeptide. This variant is 3510 bp in length, with an open reading frame extending from bases 1-3415 of the sequence. SEQ ID NO: 4 shows variant 4 of the DNA-sequence encoding an RC Kinase polypeptide. This variant is 4058 bp in length, with an open reading frame extending from bases 1-4018 of the sequence. SEQ ID NO: 5 shows variant 5 of the DNA-sequence encoding an RC Kinase polypeptide. This variant is 1460 bp in length, with an open reading frame extending from bases 1-1420 of the sequence. SEQ ID NO: 6 shows variant 6 of the DNA-sequence encoding an RC Kinase polypeptide. This variant is 1604 bp in length, with an open reading frame extending from bases 1-1564 of the sequence. SEQ ID NO: 7 shows the amino acid sequence deduced from the DNA-sequence of SEQ ID NO: 1. SEQ ID NO: 8 shows the amino acid sequence deduced from the DNA-sequence of SEQ ID NO: 2.

SEQ ID NO: 9 shows the amino acid sequence deduced from the DNA-sequence of SEQ ID NO: 3. SEQ ID NO: 10 shows the amino acid sequence deduced from the DNA-sequence of SEQ ID NO: 4. SEQ ID NO: 11 shows the amino acid sequence deduced from the DNA-sequence of SEQ ID NO: 5. SEQ ID NO: 12 shows the amino acid sequence deduced from the DNA-sequence of SEQ ID NO: 6.

Furthermore, the activity of a novel RC Kinase, particularly a human RC Kinase, is a discovery of the present invention. Human RC Kinase contains a single S_TKc kinase domain (Serine/-Threonine protein kinases, catalytic domain), beginning approximately 268 amino acid residues from the carboxy terminal of SEQ ID NO: 7, 8, 10 or 12 and spanning approximately 256 residues. Two of the variants of Human RC Kinase, SEQ ID NO: 9 and 11, are missing part of this kinase domain. The kinase domain of Human RC Kinase is highly homologous to the kinase domains of other known kinase type enzymes. Human RC Kinase as shown in SEQ ID NO: 7, 8, 10 or 12 is 44% identical and 67% similar over 287 amino acids (kinase domain) to the slime mold *Dictyostelium discoideum* protein identified by GenBank Accession No. AAC97114 and annotated as a "MEK kinase alpha." Similarly, human RC Kinase as shown in SEQ ID NO: 7, 8, 10, or 12 is 47% identical and 67% similar over 276 amino acids (kinase domain) to the common tobacco *Nicotiana tabacum* protein identified by GenBank Accession No. A48084 and annotated as a "STE11 protein kinase homolog NPK1," and is 46% identical and 63% similar over. 291 amino acids (kinase domain) to the human protein identified by GenBank Accession No. NP_002392 and annotated as a "MAP/ERK kinase kinase 3; MAPKKK3."

The coding sequences for SEQ ID NOS: 7-12 are shown in SEQ ID NOS: 1-6, respectively. The gene containing these coding sequences is located within the human chromosome 2 genomic contig identified with GenBank accession no. NT_005058, and is divided into at least 11 exons spanning more than 61,000 bases of the genome. If the 11 3'-most exons are labeled as exons C, D, E, F, G, H, I, J, K, L, and M, respectively, reading in order along the gene from 5' to 3', then six alternative splice variants are described by the invention as follows. SEQ ID NO: 1 describes a splice variant which uses all exons except exons E, G, and H. SEQ ID NO: 2 describes a splice variant which uses all exons except a portion of exon L. SEQ ID NO: 3 describes a splice variant which uses all exons except exons E and a portion of L. SEQ ID NO: 4 describes a splice variant which uses all exons except exon E. SEQ ID NO: 5 describes a splice variant which uses all exons except exons E, J, and a portion of L. SEQ ID NO: 6 describes a splice variant which uses all exons except exons E, and J.

A single exon containing most of the kinase catalytic domain has previously been annotated as "hypothetical protein FLJ23074," a gene with protein product and function unknown.

RCKinase has the ability to phosphorylate other RC Kinase polypeptides, MKK4, and MKK6. Taken together with the fact of importance of MAPK signalling, the modification of RC kinase activity can give chance of remedy against COPD, asthma, cancer, Alzheimer's disease, inflammatory diseases, and cardiovascular diseases.

Polypeptides

RC Kinase polypeptides according to the invention comprise the amino acid sequence shown in SEQ ID NO: 7, 8, 9, 10, 11, or 12 or a biologically active variant thereof, as defined below. A RC Kinase polypeptide of the invention therefore can be a portion of a RC Kinase molecule, a full-length RC Kinase molecule, or a fusion protein comprising all or a portion of a RC Kinase molecule.

Biologically Active Variants

RC Kinase variants which are biologically active, i.e., retain a RC Kinase activity, also are RC Kinase polypeptides. Preferably, naturally or non-naturally occurring RC Kinase variants have amino acid sequences which are at least about 50, preferably about 70, 75, 90, 96, or 98% identical to an amino acid sequence shown in SEQ ID NO: 7, 8, 9, 10, 11, or 12. Percent identity between a putative RC Kinase variant and an amino acid sequence of SEQ ID NO: 7, 8, 9, 10, 11, or 12 is determined by conventional methods. See, for example, Altschul et al., *Bull. Math. Bio.* 48:603 (1986), and Henikoff & Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff & Henikoff, 1992.

Those skilled in the art appreciate that there are many established algorithms available to align two amino acid sequences. The "FASTA" similarity search algorithm of Pearson & Lipman is a suitable protein alignment method for examining the level of identity shared by an amino acid sequence disclosed herein and the amino acid sequence of a putative variant. The PASTA algorithm is described by Pearson & Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman & Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity can be found using computer programs well known in the art, such as DNASTAR software. Whether an amino acid change results in a biologically active RC Kinase polypeptide can readily be determined by assaying for fibronectin binding or for RC Kinase activity, as is known in the art and described, for example, in Example 2.

Fusion Proteins

Fusion proteins are useful for generating antibodies against RC Kinase amino acid sequences and for use in various assay systems. For example, fusion proteins can be used to identify proteins which interact with portions of a RC Kinase polypeptide, including its active site. Methods such as protein affinity chromatography or library-based assays for protein-protein interactions, such as the yeast two-hybrid or phage display systems, can be used for this purpose. Such methods are well known in the art and also can be used as drug screens.

A RC Kinase fusion protein comprises two protein segments fused together by means of a peptide bond. Contiguous amino acids for use in a fusion protein can be selected from the amino acid sequence shown in SEQ ID NO: 7, 8, 9, 10, 11, or 12 or from a biologically active variant thereof, such as those described above. Preferably, a fusion protein comprises a kinase domain and/or an ATP binding site of human RC Kinase. The first protein segment also can comprise full-length RC Kinase.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the RC Kinase polypeptide-encoding sequence and the heterologous protein sequence, so that the RC Kinase polypeptide can be cleaved and purified away from the heterologous moiety.

A fusion protein can be synthesized chemically, as is known in the art. Preferably, a fusion protein is produced by covalently linking two protein segments or by standard procedures in the art of molecular biology. Recombinant DNA methods can be used to prepare fusion proteins, for example, by making a DNA construct which comprises RC Kinase coding sequences disclosed herein in proper reading frame with nucleotides encoding the second protein segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human RC Kinase can be obtained using RC Kinase polynucleotides (described below) to make suitable probes or primers to screening cDNA expression libraries from other species, such as mice, monkeys, or yeast, identifying cDNAs which encode homologs of RC Kinase, and expressing the cDNAs as is known in the art.

Polynucleotides

A RC Kinase polynucleotide can be single- or double-stranded and comprises a coding sequence or the complement of a coding sequence for a RC Kinase polypeptide. A partial coding sequence of a RC Kinase polynucleotide is shown in SEQ ID NO: 1, 2, 3, 4, 5, or 6; coding sequences of RC Kinase also are contained within the genomic sequence shown in SEQ ID NO: 3, from nucleotides 11885 to 12023 and from nucleotides 10564 to 10693.

Degenerate nucleotide sequences encoding human RC Kinase polypeptides, as well as homologous nucleotide sequences which are at least about 50, preferably about 75, 90, 96, or 98% identical to the RC Kinase coding sequences nucleotide sequences shown in SEQ ID NOS: 1 and 3 also are RC Kinase polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of RC Kinase polynucleotides which encode biologically active RC Kinase polypeptides also are RC Kinase polynucleotides.

Identification of Variants and Homologs

Variants and homologs of the RC Kinase polynucleotides disclosed above also are RC Kinase polynucleotides. Typically, homologous RC Kinase polynucleotide sequences can be identified by hybridization of candidate polynucleotides to known RC Kinase polynucleotides under stringent conditions, as is known in the art. For example, using the following wash conditions-2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25-30% basepair mismatches. More preferably, homologous nucleic acid strands contain 15-25% basepair mismatches, even more preferably 5-15% basepair mismatches.

Species homologs of the RC Kinase polynucleotides disclosed herein can be identified by making suitable probes or primers and screening cDNA expression libraries from other species, such as mice, monkeys, or yeast. Human variants of RC Kinase polynucleotides can be identified, for example, by screening human cDNA expression libraries. It is well known that the $T_m$ of a double-stranded DNA decreases by 1-1.5° C. with every 1% decrease in homology (Bonner et al., *J. Mol. Biol.* 81, 123 (1973). Variants of human RC Kinase polynucleotides or RC Kinase polynucleotides of other species can therefore be identified, for example, by hybridizing a putative homologous RC Kinase polynucleotide with a polynucleotide having a nucleotide sequence of SEQ ID NO: 1, 2, 3, 4, 5, or 6 or an ephrin-like serine protease coding sequence of SEQ ID NO: 3 to form a test hybrid. The melting temperature of the test hybrid is compared with the melting temperature of a hybrid comprising RC Kinase polynucleotides having perfectly complementary nucleotide sequences, and the number or percent of basepair mismatches within the test hybrid is calculated.

Nucleotide sequences which hybridize to RC Kinase polynucleotides or their complements following stringent hybridization and/or wash conditions are also RC Kinase polynucleotides. Stringent wash conditions are well known and understood in the art and are disclosed, for example, in Sambrook et al., MOLECULAR CLONING: A LABORATORY MANUAL, 2d ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a RC Kinase polynucleotide having a coding sequence disclosed herein and a polynucleotide sequence which is at least about 50, preferably about 75, 90, 96, or 98% identical to that nucleotide sequence can be calculated, for example, using the equation of Bolton and McCarthy, *Proc. Natl. Acad. Sci. U.S.A.* 48, 1390 (1962):

$$T_m=81.5^\circ \text{ C.}-16.6(\log_{10}[\text{Na}^+])+0.41(\%G+C)-0.63(\%\text{formamide})-600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A naturally occurring RC Kinase polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction (PCR), or synthesized using an automatic synthesizer. Methods for isolating polynucleotides are routine and are known in the art. Any such technique for obtaining a polynucleotide can be used to obtain isolated RC Kinase polynucleotides. For example, restriction enzymes and probes can be used to isolate polynucleotide fragments which comprise RC Kinase nucleotide sequences. Isolated polynucleotides are in preparations which are free or at least 70, 80, or 90% free of other molecules.

RC Kinase cDNA molecules can be made with standard molecular biology techniques, using RC Kinase mRNA as a template. RC Kinase cDNA molecules can thereafter be replicated using molecular biology techniques known in the art and disclosed in manuals such as Sambrook et al. (1989). An amplification technique, such as PCR, can be used to obtain additional copies of RC Kinase polynucleotides, using either human genomic DNA or cDNA as a template.

Alternatively, synthetic chemistry techniques can be used to synthesize RC Kinase polynucleotides. The degeneracy of the genetic code allows alternate nucleotide sequences to be synthesized which will encode a RC Kinase polypeptide having, for example, the amino acid sequence shown in SEQ ID NO: 7, 8, 9, 10, 11, or 12 or a biologically active variant of that sequence.

Obtaining Full-Length Polynucleotides

The partial sequence of SEQ ID NO: 1, 2, 3, 4, 5, or 6 or its complement can be used to identify the corresponding full length gene from which they were derived. The partial sequences can be nick-translated or end-labeled with $^{32}$P using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., 1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting radiographies are compared to duplicate plates of colonies or plaques; each exposed spot corresponds to a positive colony or plaque. The colonies or plaques are selected and expanded, and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease III digestion (McCombie et al., *Methods* 3, 33-40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences encoding the disclosed portions of human RC Kinase to detect upstream sequences such as promoters and regulatory elements. For example, restriction-site PCR uses universal primers to retrieve unknown sequence adjacent to a known locus (Sarkar, *PCR Methods Applic.* 2, 318-322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111-119, 1991). In this method, multiple restriction enzyme digestions and ligations are used to place an engineered double-stranded sequence into an unknown fragment of the DNA molecule before performing PCR.

Another method which can be used to retrieve unknown sequences is that of Parker et al., *Nucleic Acids Res.* 19, 3055-3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA which might be present in limited amounts in a particular sample.

Obtaining Polypeptides

RC Kinase polypeptides can be obtained, for example, by purification from human cells, by expression of RC Kinase polynucleotides, or by direct chemical synthesis.

Protein Purification

RC Kinase polypeptides can be purified from cells, including cells which have been transfected with RC Kinase expression constructs. Kidney, fetal lung, testis, B cells, adult lung epithelium, and chronic lymphatic leukemia cells are particularly useful sources of RC Kinase polypeptides. A purified RC Kinase polypeptide is separated from other compounds which normally associate with the RC Kinase polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified RC Kinase polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described in Example 2.

Expression of Polynucleotides

To express a RC Kinase polypeptide, a RC Kinase polynucleotide can be inserted into an expression vector which contains the necessary elements for the transcription and translation of the inserted coding sequence. Methods which are well known to those skilled in the art can be used to construct expression vectors containing sequences encoding RC Kinase polypeptides and appropriate transcriptional and translational control elements. These methods include in vitro recombinant DNA techniques, synthetic techniques, and in vivo genetic recombination. Such techniques are described, for example, in Sambrook et al. (1989) and Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a RC Kinase polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a RC Kinase polypeptide, vectors based on SV40 or EBV can be used with an appropriate selectable marker.

Bacterial and Yeast Expression Systems

In bacterial systems, a number of expression vectors can be selected depending upon the use intended for the RC Kinase polypeptide. For example, when a large quantity of a RC Kinase polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene), in which the sequence encoding the RC Kinase polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503-5509, 1989 or pGEX vectors (Promega, Madison, Wis.) can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or Factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516-544, 1987.

Plant and Insect Expression Systems

If plant expression vectors are used, the expression of sequences encoding RC Kinase polypeptides can be driven by any of a number of promoters. For example, viral promoters such as the $^{35}$S and 19S promoters of CaMV can be used alone or in combination with the omega leader sequence from TMV (Takamatsu *EMBO J.* 6, 307-311, 1987). Alternatively, plant promoters such as the small subunit of RUBISCO or heat shock promoters can be used (Coruzzi et al., *EMBO J.* 3, 1671-1680, 1984; Broglie et al., *Science* 224, 838-843, 1984; Winter et al., *Results Probl. Cell Differ.* 17, 85-105, 1991). These constructs can be introduced into plant cells by direct DNA transformation or by pathogen-mediated transfection. Such techniques are described in a number of generally available reviews (see, for example, Hobbs or Murray, in McGraw Hill Yearbook of Science and Technology, McGraw Hill, New York, N.Y., pp. 191-196, 1992).

An insect system also can be used to express a RC Kinase polypeptide. For example, in one such system *Autographa californica* nuclear polyhedrosis virus (AcNPV) is used as a vector to express foreign genes in *Spodoptera frugiperda* cells or in *Trichoplusia larvae*. Sequences encoding RC Kinase polypeptides can be cloned into a non-essential region of the virus, such as the polyhedrin gene, and placed under control of the polyhedrin promoter. Successful insertion of RC Kinase polypeptides will render the polyhedrin gene inactive and produce recombinant virus lacking coat protein. The recombinant viruses can then be used to infect, for example, *S. frugiperda* cells or *Trichoplusia larvae* in which RC Kinase polypeptides can be expressed (Engelhard et al., *Proc. Nat. Acad. Sci.* 91, 3224-3227, 1994).

Mammalian Expression Systems

A number of viral-based expression systems can be utilized in mammalian host cells. For example, if an adenovirus is used as an expression vector, sequences encoding RC Kinase polypeptides can be ligated into an adenovirus transcription/translation complex consisting of the late promoter and tripartite leader sequence. Insertion in a non-essential E1 or E3 region of the viral genome can be used to obtain a viable virus which is capable of expressing a RC Kinase polypeptide in infected host cells (Logan & Shenk, *Proc. Natl. Acad. Sci.* 81, 3655-3659, 1984). In addition, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding RC Kinase polypeptides. Such signals include the ATG initiation codon and adjacent sequences. In cases where sequences encoding a RC Kinase polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125-162, 1994).

Host Cells

A host cell strain can be chosen for its ability to modulate the expression of the inserted sequences or to process an expressed RC Kinase polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express RC Kinase polypeptides can be transformed using expression vectors which can contain viral origins of replication and/or endogenous expression elements and a selectable marker gene on the same or on a separate vector. Following the introduction of the vector, cells can be allowed to grow for 1-2 days in an enriched medium before they are switched to a selective medium. The purpose of the selectable marker is to confer resistance to selection, and its presence allows growth and recovery of cells which successfully express the introduced RC Kinase sequences. Resistant clones of stably transformed cells can be proliferated using tissue culture techniques appropriate to the tell type.

Any number of selection systems can be used to recover transformed cell lines. These include, but are not limited to, the herpes simplex virus thymidine kinase (Wigler et al., *Cell* 11, 223-32, 1977) and adenine phosphoribosyltransferase (Lowy et al., *Cell* 22, 817-23, 1980). Genes which can be employed in $tk^-$ or $aprt^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567-70, 1980); npt confers resistance to the aminoglycosides, neomycin and G-418 (Colbere-Garapin et al., *J. Mol. Biol.* 150, 1-14, 1981); and als and pat confer resistance to chlorsulfron and phosphinotricin acetyltransferase, respectively (Murray, 1992 supra). Additional selectable genes have been described, for example trpB, which allows cells to utilize indole in place of tryptophan, or hisD, which allows cells to utilize histinol in place of histidine (Hartman & Mulligan, *Proc. Natl. Acad. Sci* 85, 8047-51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121-131, 1995).

Detecting Expression of Polypeptides

Although the presence of marker gene expression suggests that the RC Kinase polynucleotide is also present, its presence and expression may need to be confirmed. For example, if a sequence encoding a RC Kinase polypeptide is inserted within a marker gene sequence, transformed cells containing sequences which encode a RC Kinase polypeptide can be identified by the absence of marker gene function. Alternatively, a marker gene can be placed in tandem with a sequence encoding a RC Kinase polypeptide under the control of a single promoter. Expression of the marker gene in response to induction or selection usually indicates expression of the RC Kinase polynucleotide.

Alternatively, host cells which contain a RC Kinase polynucleotide and which express a RC Kinase polypeptide can be identified by a variety of procedures known to those of skill in the art. These procedures include, but are not limited to, DNA-DNA or DNA-RNA hybridizations and protein bioassay or immunoassay techniques which include membrane, solution, or chip-based technologies for the detection and/or quantification of nucleic acid or protein.

The presence of a polynucleotide sequence encoding a RC Kinase polypeptide can be detected by DNA-DNA or DNA-RNA hybridization or amplification using probes or fragments or fragments of polynucleotides encoding a RC Kinase polypeptide. Nucleic acid amplification-based assays involve the use of oligonucleotides selected from sequences encoding a RC Kinase polypeptide to detect transformants which contain a RC Kinase polynucleotide.

A variety of protocols for detecting and measuring the expression of a RC Kinase polypeptide, using either polyclonal or monoclonal antibodies specific for the polypeptide, are known in the art Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a RC Kinase polypeptide can be used, or a competitive binding assay can be employed. These and other assays are described in Hampton et al., Serological Methods: a Laboratory Manual, APS Press, St. Paul, Minn., 1990) and Maddox et al., *J. Exp. Med.* 158, 1211-1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding RC Kinase polypeptides include oligolabeling, nick translation, end-labeling, or PCR amplification using a labeled nucleotide. Alternatively, sequences encoding a RC Kinase polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding a RC Kinase polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode RC Kinase polypeptides can be designed to contain signal sequences which direct secretion of RC Kinase polypeptides through a prokaryotic or eukaryotic cell membrane.

Other constructions can be used to join a sequence encoding a RC Kinase polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the RC Kinase polypeptide can be used to facilitate purification. One such expression vector provides for expression of a fusion protein containing a RC Kinase polypeptide and 6 histidine residues preceding a thioredoxin or an enterokinase cleavage site. The histidine residues facilitate purification on IMAC (immobilized metal ion affinity chromatography as described in Porath et al., *Prot. Exp. Purif.* 3, 263-281, 1992), while the enterokinase cleavage site provides a means for purifying the RC Kinase polypeptide from the fusion protein. Vectors which contain fusion proteins are disclosed in Kroll et al., *DNA Cell Biol.* 12, 441-453, 1993).

Chemical Synthesis

Sequences encoding a RC Kinase polypeptide can be synthesized, in whole or in part, using chemical methods well known in the art (see Caruthers et al., *Nucl. Acids Res. Symp. Ser.* 215-223, 1980; Horn et al. *Nucl. Acids Res. Symp. Ser.* 225-232, 1980). Alternatively, a RC Kinase polypeptide itself can be produced using chemical methods to synthesize its amino acid sequence. For example, RC Kinase polypeptides can be produced by direct peptide synthesis using solid-phase techniques (Merrifield, *J. Am. Chem. Soc.* 85, 2149-2154, 1963; Roberge et al., *Science* 269, 202-204, 1995). Protein synthesis can be performed using manual techniques or by automation. Automated synthesis can be achieved, for example, using Applied Biosystems 431A Peptide Synthesizer (Perkin Elmer). Various fragments of RC Kinase polypeptides can be separately synthesized and combined using chemical methods to produce a full-length molecule.

The newly synthesized peptide can be substantially purified by preparative high performance liquid chromatography (e.g., Creighton, Proteins: Structures and Molecular Principles, WH Freeman and Co., New York, N.Y., 1983). The composition of a synthetic RC Kinase polypeptide can be confirmed by amino acid analysis or sequencing (e.g., the Edman degradation procedure; see Creighton, supra). Additionally, any portion of the amino acid sequence of the RC Kinase polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce RC Kinase polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences disclosed herein can be engineered using methods generally known in the art to alter RC Kinase polypeptide-encoding sequences for a variety of reasons, including modification of the cloning, processing, and/or expression of the gene product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a RC Kinase polypeptide. "Antibody" as used herein includes intact immunoglobulin molecules, as well as fragments thereof, such as Fab, $F(ab')_2$, and Fv, which are capable of binding an epitope of a RC Kinase polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a RC Kinase polypeptide can be used therapeutically, as well as in immunochemical assays, including but not limited to Western blots, ELISAs, radioimmunoassays, immunohistochemical assays, immunoprecipitations, or other immunochemical assays known in the art. Various immunoassays can be used to identify anti-bodies having the desired specificity. Numerous protocols for competitive binding or immuno-radiometric assays are well known in the art. Such immunoassays typically involve the measurement of complex formation between an immunogen and an antibody which specifically binds to the immunogen.

Typically, an antibody which specifically binds to a RC Kinase polypeptide provides a detection signal at least 5-, 10-, or 20-fold higher than a detection signal provided with other proteins when used in an immunochemical assay. Preferably, antibodies which specifically bind to RC Kinase polypeptides do not detect other proteins in immunochemical assays and can immunoprecipitate a RC Kinase polypeptide from solution.

RC Kinase polypeptides can be used to immunize a mammal, such as a mouse, rat, rabbit, guinea pig, monkey, or human, to produce polyclonal antibodies. If desired, a RC Kinase polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole ant hemocyanin, and dinitrophenol). Among adjuvants used in humans, BCG (*bacilli Calmette-Guerin*) and *Corynebacterium parvum* are especially useful.

Monoclonal antibodies which specifically bind to a RC Kinase polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495-497, 1985; Kozbor et al., *J. Immunol. Methods* 81, 31-42, 1985; Cote et al., *Proc. Natl. Acad. Sci.* 80, 2026-2030, 1983; Cole et al., *Mol. Cell. Biol.* 62, 109-120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851-6855, 1984; Neuberger et al., *Nature* 312, 604-608, 1984; Takeda et al., *Nature* 314, 452-454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, one can produce humanized antibodies using recombinant methods, as described in GB2188638B. Antibodies which specifically bind to a RC Kinase polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to RC Kinase polypeptides. Antibodies with related specificity, but of distinct idiotypic composition, can be generated by chain shuffling from random combinatorial immunoglobin libraries (Burton, *Proc. Natl. Acad. Sci.* 88, 11120-23, 1991).

Single-chain antibodies also can be constructed using a DNA amplification method, such as PCR, using hybridoma cDNA as a template (Thirion et al., 1996, *Eur. J. Cancer Prev.* 5, 507-11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 15963. Construction of bivalent, bispecific single-chain antibodies is taught in Mallender & Voss, 1994, *J. Biol. Chem.* 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61, 497-501; Nicholls et al., 1993, *J. Immunol. Meth.* 165, 81-91.

Antibodies which specifically bind to RC Kinase polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833-3837, 1989; Winter et al., *Nature* 349, 293-299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies of the invention can be purified by methods well known in the art. For example, antibodies can be affinity purified by passage over a column to which a RC Kinase polypeptide is bound. The bound antibodies can then be eluted from the column using a buffer with a high salt concentration.

Antisense Oligonucleotides

Antisense oligonucleotides are nucleotide sequences which are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of RC Kinase gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkyl-phosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1-8, 1994; Sonveaux, *Meth. Mol. Biol.* 26, 1-72, 1994; Uhlmann et al., *Chem. Rev.* 90, 543-583, 1990.

Modifications of RC Kinase gene expression can be obtained by designing antisense oligo-nucleotides which will form duplexes to the control, 5', or regulatory regions of the RC Kinase gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, Molecular and Immunologic Approaches, Futura Publishing Co., Mt. Kisco, N.Y., 1994). An antisense oligonucleotide also can be designed to block translation of mRNA by preventing the transcript from binding to ribosomes.

Precise complementarity is not required for successful duplex formation between an antisense oligonucleotide and the complementary sequence of a RC Kinase polynucleotide. Antisense oligonucleotides which comprise, for example, 2, 3, 4, or 5 or more stretches of contiguous nucleotides which are precisely complementary to a RC Kinase polynucleotide, each separated by a stretch of contiguous nucleotides which are not complementary to adjacent RC Kinase nucleotides, can provide targeting specificity for RC Kinase mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular RC Kinase polynucleotide sequence.

Antisense oligonucleotides can be modified without affecting their ability to hybridize to a RC Kinase polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152-158, 1992; Uhlmann et al., *Chem. Rev.* 90, 543-584, 1990; Uhlmann et al., *Tetrahedron Lett.* 215, 3539-3542, 1987.

Ribozymes

Ribozymes are RNA molecules with catalytic activity. See, e.g., Cech, *Science* 236, 1532-1539; 1987; Cech, *Ann. Rev. Biochem.* 59, 543-568; 1990, Cech, *Curr. Opin. Struct. Biol.* 2, 605-609; 1992, Couture & Stinchcomb, *Trends Genet.* 12, 510-515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a RC Kinase polynucleotide can be used to generate ribozymes which will specifically bind to mRNA transcribed from the RC Kinase polynucleotide. Methods of designing and constructing ribozymes which can cleave other RNA molecules in trans in a highly sequence specific manner have been developed and described in the art (see Haseloff et al. *Nature* 334; 585-591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a RC Kinase RNA target are initially identified by scanning the RNA molecule for ribozyme cleavage sites which include the following sequences: GUA, GUU, and GUC. Once identified, short RNA sequences of between 15 and 20 ribonucleotides corresponding to the region of the RC Kinase target RNA containing the cleavage site can be evaluated for secondary structural features which may render the target inoperable. The suitability of candidate targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related; thus, upon hybridizing to the RC Kinase target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease RC Kinase expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of RC Kinase mRNA occurs only when both a ribozyme and a target gene are induced in the cells.

Screening Methods

The invention provides methods for identifying modulators, i.e., candidate or test compounds which bind to RC Kinase polypeptides or polynucleotides and/or have a stimulatory or inhibitory effect on, for example, expression or activity of the RC Kinase polypeptide or polynucleotide, so as to regulate signaling through a MAP kinase phosphorelay system, regulate the production of inflammatory mediators, and regulate degradation of the extracellular matrix. Decreased signaling through a MAP kinase phosphorelay system and decreased production of inflammatory mediators are useful for preventing undesired inflammation, cell proliferation, cell differentiation, cytokine production, or apoptosis. Increased signaling through a MAP kinase phosphorelay system and increased production of inflammatory mediators is useful for enhancing the repair of damaged tissues, enhancing resistance to irritants or toxins, or increasing the resistance to infection. Decreased extracellular matrix degradation is useful for preventing damage or irreversible changes to lung microstructures and preventing or suppressing malignant cells from metastasizing. Increased extracellular matrix degradation may be desired, for example, in developmental disorders characterized by inappropriately low levels of extracellular matrix degradation or in regeneration.

The invention provides assays for screening test compounds which bind to or modulate the activity of a RC Kinase polypeptide or a RC Kinase polynucleotide. A test compound preferably binds to a RC Kinase polypeptide or polynucleotide. More preferably, a test compound decreases a RC Kinase activity of a RC Kinase polypeptide or expression of a RC Kinase polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl. Acad. Sci. U.S.A.* 90, 6909, 1993; Erb et al. *Proc. Natl. Acad. Sci. U.S.* 91, 11422, 1994; Zuckermann et al., *J. Med. Chem.* 37, 2678, 1994; Cho et al., *Science* 261, 1303, 1993; Carell et al., *Angew. Chem. Int. Ed. Engl.* 33, 2059, 1994; Carell et al., *Angew. Chem. Int. Ed. Engl.* 33, 2061; Gallop et al., *J. Med. Chem.* 37, 1233, 1994). Libraries of compounds can be presented in solution (see, e.g., Houghten, *BioTechniques* 13, 412-421, 1992), or on beads (Lam, *Nature* 354, 82-84, 1991), chips (Fodor, *Nature* 364, 555-556, 1993), bacteria or spores (Ladner, U.S. Pat. No. 5,223,409), plasmids (Cull et al., *Proc. Natl. Acad. Sci. U.S.A.* 89, 1865-1869, 1992), or phage (Scott & Smith, *Science* 249, 386-390, 1990; Devlin, *Science* 249, 404-406, 1990); Cwirla et al., *Proc. Natl. Acad. Sci.* 97, 6378-6382, 1990; Felici, *J. Mol. Biol.* 222, 301-310, 1991; and Ladner, U.S. Pat. No. 5,223,409).

High Throughput Screening

Test compounds can be screened for the ability to bind to RC Kinase polypeptides or polynucleotides or to affect RC Kinase activity or RC Kinase gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 161418 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries Novel and Traditional Approaches," reported at the First Annual Conference of The Society for Biomolecular Screening in Philadelphia, Pa. Nov. 7-10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 5763 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule which binds to and occupies the active site or a fibronectin domain of the RC Kinase polypeptide, thereby making the active site or fibronectin domain inaccessible to substrate such that normal biological activity is prevented. Examples of such small molecules include, but are not limited to, small peptides or peptide-like molecules. In binding assays, either the test compound or the RC Kinase polypeptide can comprise a detectable label, such as a fluorescent, radioisotopic, chemiluminescent, or enzymatic label, such as horseradish peroxidase, alkaline phosphatase, or luciferase. Detection of a test compound which is bound to the RC Kinase polypeptide can then be accomplished, for example, by direct counting of radioemission, by scintillation counting, or by determining conversion of an appropriate substrate to a detectable product.

Alternatively, binding of a test compound to a RC Kinase polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a RC Kinase polypeptide. (McConnell et al., *Science* 257, 1906-1912, 1992).

Determining the ability of a test compound to bind to a RC Kinase polypeptide also can be accomplished using a technology such as real-time Bimolecular Interaction Analysis (BIA). Sjolander & Urbaniczky, *Anal. Chem.* 63, 2338-2345, 1991, and Szabo et al., *Curr. Opin. Struct Biol.* 5, 699-705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a RC Kinase polypeptide can be used as a "bait protein" in a two-hybrid assay or three-hybrid assay (see, e.g., U.S. Pat. No. 5,283,317; Zervos et al., *Cell* 72, 223-232, 1993; Madura et al., *J. Biol. Chem.* 268, 12046-12054, 1993; Bartel et al., *BioTechniques* 14, 920-924, 1993; Iwabuchi et al., *Oncogene* 8, 1693-1696, 1993; and Brent WO94/10300), to identify other proteins which bind to or interact with the RC Kinase polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding a RC Kinase polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein which interacts with the RC Kinase polypeptide.

It may be desirable to immobilize either the RC Kinase polypeptide (or polynucleotide) or the test compound to facilitate separation of bound from unbound forms of one or both of the interactants, as well as to accommodate automation of the assay. Thus, either the RC Kinase polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the RC Kinase polypeptide (or polynucleotide) or test compound to a solid support, including use of covalent and non-covalent linkages, passive absorption, or pairs of binding moieties attached respectively to the polypeptide or test compound and the solid support. Test compounds are preferably bound to the solid support in an array, so that the location of individual test compounds can be tracked. Binding of a test compound to a RC Kinase polypeptide (or polynucleotide) can be accomplished in any vessel suitable for containing the reactants. Examples of such vessels include microtiter plates, test tubes, and microcentrifuge tubes.

In one embodiment, a RC Kinase polypeptide is a fusion protein comprising a domain that allows the RC Kinase polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed RC Kinase polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either a RC Kinase polypeptide (or polynucleotide) or a test compound can be immobilized utilizing conjugation of biotin and streptavidin. Biotinylated RC Kinase polypeptides or test compounds can be prepared from biotin-NHS (N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a RC Kinase polypeptide polynucleotides, or a test compound, but which do not interfere with a desired binding site, such as the active site or a fibronectin domain of the RC Kinase polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the RC Kinase polypeptide (or polynucleotides) or test compound, enzyme-linked assays which rely on detecting a RC Kinase activity of the RC Kinase polypeptide, and SDS gel electrophoresis under non-reducing conditions.

Screening for test compounds which bind to a RC Kinase polypeptide or polynucleotide also can be carried out in an intact cell. Any cell which comprises a RC Kinase polynucleotide or polypeptide can be used in a cell-based assay system. A RC Kinase polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA468, SK-BR3, and BT474, the A549 lung cancer cell line, and the H392 glioblastoma cell line, can be used. An intact cell is contacted with a test compound. Binding of the test compound to a RC Kinase polypeptide or polynucleotide is determined as described above, after lysing the cell to release the RC Kinase polypeptide-test compound complex.

Enzyme Assays

Test compounds can be tested for the ability to increase or decrease a RC Kinase activity of a RC Kinase polypeptide. RC Kinase activity can be measured, for example, using the methods referenced in Example 1. RC Kinase activity can be measured after contacting either a purified RC Kinase polypeptide, a cell extract, or an intact cell with a test compound. A test compound which decreases RC Kinase activity by at least about 10, preferably about 50, more preferably about 75, 90, or 100% is identified as a potential agent for decreasing signaling through a MAP kinase phosphorelay system, production of inflammatory mediators, or extracellular matrix degradation. A test compound which increases RC Kinase activity by at least about 10, preferably about 50, more preferably about 75, 90, or 100% is identified as a potential agent for increasing signaling through a MAP kinase phosphorelay system, production of inflammatory mediators, or extracellular matrix degradation.

Gene Expression

In another embodiment, test compounds which increase or decrease RC Kinase gene expression are identified. A RC Kinase polynucleotide is contacted with a test compound, and the expression of an RNA or polypeptide product of the RC Kinase polynucleotide is determined. The level of expression of RC Kinase mRNA or polypeptide in the presence of the test compound is compared to the level of expression of RC Kinase mRNA or polypeptide in the absence of the test compound. The test compound can then be identified as a modulator of expression based on this comparison. For example, when expression of RC Kinase mRNA or polypeptide is greater in the presence of the test compound than in its absence, the test compound is identified as a stimulator or enhancer of RC Kinase mRNA or polypeptide is less expression. Alternatively, when expression of the mRNA or protein is less in the presence of the test compound than in its absence, the test compound is identified as an inhibitor of RC Kinase mRNA or polypeptide expression.

The level of RC Kinase mRNA or polypeptide expression in the cells can be determined by methods well known in the art for detecting mRNA or protein. Either qualitative or quantitative methods can be used. The presence of polypeptide products of a RC Kinase polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a RC Kinase polypeptide.

Such screening can be carried out either in a cell-free assay system or in an intact cell. Any cell which expresses a RC Kinase polynucleotide can be used in a cell-based assay system. The RC Kinase polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA468, SK-BR3, and BT474, the A549 lung cancer cell line, and the H392 glioblastoma cell line, can be used.

Pharmaceutical Compositions

The invention also provides pharmaceutical compositions which can be administered to a patient to achieve a therapeutic effect. Pharmaceutical compositions of the invention can comprise a RC Kinase polypeptide, RC Kinase polynucleotide, antibodies which specifically bind to a RC Kinase polypeptide, or mimetics, agonists, antagonists, or inhibitors of a RC Kinase polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents which increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1-50 mM histidine, 0.1%-2% sucrose, and 2-7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Predictive, Diagnostic and Prognostic Assays

The present invention provides methods for determining whether a subject is at risk for developing COPD and other disorders by detecting the disclosed biomarkers, i.e., the disclosed polynucleotide marker comprising the polynucleotide sequence of the SEQ ID NO: 1, 2, 3, 4, 5, or 6 and/or the polypeptide markers encoded thereby or polypeptide markers comprising the polypeptide sequences of the SEQ ID NO: 7, 8, 9, 10, 11, or 12.

In clinical applications, biological samples can be screened for the presence and/or absence of the biomarkers identified herein. Such samples are for example needle biopsy cores, surgical resection samples, or body fluids like serum, thin needle nipple aspirates and urine. For example, these methods include obtaining a biopsy, which is optionally fractionated by cryostat sectioning to enrich diseases cells to about 80% of the total cell population. In certain embodiments, polynucleotides extracted from these samples may be amplified using techniques well known in the art. The expression levels of selected markers detected would be compared with statistically valid groups of diseased and healthy samples.

In one embodiment the diagnostic method comprises determining whether a subject has an abnormal mRNA and/or protein level of the disclosed markers, such as by Northern blot analysis, reverse transcription-polymerase chain reaction (RT-PCR), in situ hybridization, immunoprecipitation, Western blot hybridization, or immunohistochemistry. According to the method, cells are obtained from a subject and the levels of the disclosed biomarkers, protein or mRNA level, is determined and compared to the level of these markers in a healthy subject. An abnormal level of the biomarker polypeptide or mRNA levels is likely to be indicative of diseases such as COPD.

In another embodiment the diagnostic method comprises determining whether a subject has an abnormal DNA content of said genes or said genomic loci, such as by Southern blot analysis, dot blot analysis, Fluorescence or Colorimetric In Situ Hybridization, Comparative Genomic Hybridization or quantitative PCR. In general these assays comprise the usage of probes from representative genomic regions. The probes contain at least parts of said genomic regions or sequences complementary or analogous to said regions. In particular intra- or intergenic regions of said genes or genomic regions. The probes can consist of nucleotide sequences or sequences of analogous functions (e.g. PNAs, Morpholino oligomers) being able to bind to target regions by hybridization. In general genomic regions being altered in said patient samples are compared with unaffected control samples (normal tissue from the same or different patients, surrounding unaffected tissue, peripheral blood) or with genomic regions of the same sample that don't have said alterations and can therefore serve as internal controls. In a preferred embodiment regions located on the same chromosome are used. Alternatively, gonosomal regions and/or regions with defined varying amount in the sample are used. In one favored embodiment the DNA content, structure, composition or modification is compared that lie within distinct genomic regions. Especially favored are methods that detect the DNA content of said samples, where the amount of target regions are altered by amplification and or deletions. In another embodiment the target regions are analyzed for the presence of polymorphisms (e.g. Single Nucleotide Polymorphisms or mutations) that affect or predispose the cells in said samples with regard to clinical aspects, being of diagnostic, prognostic or therapeutic value. Preferably, the identification of sequence variations is used to define haplotypes that result in characteristic behavior of said samples with said clinical aspects.

One embodiment of the invention is a method for the prediction, diagnosis or prognosis of COPD by the detection of at least 10, at least 5, or at least 4, or at least 3 and more preferably at least 2 markers whereby the markers are genes and/or genomic nucleic acid sequences that are located on one chromosomal region which is altered in COPD.

One further embodiment of the invention is a method for the prediction, diagnosis or prognosis of COPD by the detection of RC Kinase gene and/or genomic nucleic acid sequence.

In one embodiment, the method for the prediction, diagnosis or prognosis of COPD and COPD in particular is done by the detection of:

(a) polynucleotide of the SEQ ID NO: 1, 2, 3, 4, 5, or 6;
(b) a polynucleotide which hybridizes under stringent conditions to a polynucleotide specified in (a) encoding a polypeptide exhibiting the same biological function as RC Kinase;
(c) a polynucleotide the sequence of which deviates from the polynucleotide specified in (a) and (b) due to the degeneracy of the genetic code encoding a polypeptide exhibiting the same biological function as RC Kinase; or
(d) a polynucleotide which represents a specific fragment, derivative or allelic variation of a polynucleotide sequence specified in (a) to (c) encoding a polypeptide exhibiting the same biological function as RC Kinase;

in a biological sample comprising the following steps: hybridizing any polynucleotide or analogous oligomer specified in (a) to (d) to a polynucleotide material of a biological sample, thereby forming a hybridization complex; and detecting said hybridization complex.

In another embodiment the method for the prediction, diagnosis or prognosis of COPD is done as just described but, wherein before hybridization, the polynucleotide material of the biological sample is amplified.

In another embodiment the method for the diagnosis or prognosis of COPD in particular is done by the detection of:

(a) a polynucleotide selected from the polynucleotides of the SEQ ID NO: 1, 2, 3, 4, 5, or 6;
(b) a polynucleotide which hybridizes under stringent conditions to a polynucleotide specified in (a) encoding a polypeptide exhibiting the same biological function as RC Kinase;
(c) a polynucleotide the sequence of which deviates from the polynucleotide specified in (a) and (b) due to the degeneracy of the genetic code encoding a polypeptide exhibiting the same biological function as RC Kinase;

(d) a polynucleotide which represents a specific fragment, derivative or allelic variation of a polynucleotide sequence specified in (a) to (c) encoding a polypeptide exhibiting the same biological function as RC Kinase;

(e) a polypeptide encoded by a polynucleotide sequence specified in (a) to (d); or (f) a polypeptide comprising the polypeptide of SEQ ID NO: 7, 8, 9, 10, 11, or 12:

comprising the steps of contacting a biological sample with a reagent which specifically interacts with the polynucleotide specified in (a) to (d) or the polypeptide specified in (e) or (f).

1. DNA Array Technology

In one embodiment, the present Invention also provides a method wherein polynucleotide probes are immobilized an a DNA chip in an organized array. Oligonucleotides can be bound to a solid Support by a variety of processes, including lithography. For example a chip can hold up to 41,000 oligonucleotides (GeneChip, Affymetrix). The present invention provides significant advantages over the available tests for COPD, such as COPD, because it increases the reliability of the test by providing an array of polynucleotide markers on a single chip.

The method includes obtaining a biopsy of an affected person, which is optionally fractionated by cryostat sectioning to enrich diseased cells to about 80% of the total cell population and the use of body fluids such as serum or urine, serum or cell containing liquids (e.g. derived from fine needle aspirates). The DNA or RNA is then extracted, amplified, and analyzed with a DNA chip to determine the presence of absence of the marker polynucleotide sequences. In one embodiment, the polynucleotide probes are spotted onto a substrate in a two-dimensional matrix or array. samples of polynucleotides can be labeled and then hybridized to the probes. Double-stranded polynucleotides, comprising the labeled sample polynucleotides bound to probe polynucleotides, can be detected once the unbound portion of the sample is washed away.

The probe polynucleotides can be spotted on substrates including glass, nitrocellulose, etc. The probes can be bound to the Substrate by either covalent bonds or by non-specific interactions, such as hydrophobic interactions. The sample polynucleotides can be labeled using radioactive labels, fluorophores, chromophores, etc. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. No. 5,593,839; U.S. Pat. No. 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631, 734. Further, arrays can be used to examine differential expression of genes and can be used to determine gene function. For example, arrays of the instant polynucleotide sequences can be used to determine if any of the polynucleotide sequences are differentially expressed between normal cells and diseased cells, for example. High expression of a particular message in a diseased sample, which is not observed in a corresponding normal sample, can indicate a COPD specific protein.

Accordingly, in one aspect, the invention provides probes and primers that are specific to the unique polynucleotide markers disclosed herein.

In one embodiment, the method comprises using a polynucleotide probe to determine the presence of malignant or COPD cells in particular in a tissue from a patient. Specifically, the method comprises:

1) providing a polynucleotide probe comprising a nucleotide sequence at least 12 nucleotides in length, preferably at least 15 nucleotides, more preferably, 25 nucleotides, and most preferably at least 40 nucleotides, and up to all or nearly all of the coding sequence which is complementary to a portion of the coding sequence of a polynucleotide of the SEQ ID NO: 1, 2, 3, 4, 5, or 6 or a sequence complementary thereto and is
2) differentially expressed in COPD;
3) obtaining a tissue sample from a patient with COPD;
4) providing a second tissue sample from a patient with no COPD;
5) contacting the polynucleotide probe under stringent conditions with RNA of each of said first and second tissue samples (e.g., in a Northern blot or in situ hybridization assay); and
6) comparing (a) the amount of hybridization of the probe with RNA of the first tissue sample, with (b) the amount of hybridization of the probe with RNA of the second tissue sample;

wherein a statistically significant difference in the amount of hybridization with the RNA of the first tissue sample as compared to the amount of hybridization with the RNA of the second tissue sample is indicative of COPD and COPD in particular in the first tissue sample.

2. Data Analysis Methods

Comparison of the expression levels of one or more "RC Kinase" with reference expression levels, e.g., expression levels in diseased cells of COPD or in normal counterpart cells, is preferably conducted using computer systems. In one embodiment, expression levels are obtained in two cells and these two sets of expression levels are introduced into a computer system for comparison. In a preferred embodiment, one set of expression levels is entered into a computer system for comparison with values that are already present in the computer system, or in computer-readable form that is then entered into the computer system.

In one embodiment, the invention provides a computer readable form of the gene expression profile data of the invention, or of values corresponding to the level of expression of at least one "RC Kinase" in a diseased cell. The values can be mRNA expression levels obtained from experiments, e.g., microarray analysis. The values can also be mRNA levels normalized relative to a reference gene whose expression is constant in numerous cells under numerous conditions, e.g., GAPDH. In other embodiments, the values in the computer are ratios of, or differences between, normalized or non-normalized mRNA levels in different samples.

The gene expression profile data can be in the form of a table, such as an Excel table. The data can be alone, or it can be part of a larger database, e.g., comprising other expression profiles. For example, the expression profile data of the invention can be part of a public database. The computer readable form can be in a computer. In another embodiment, the invention provides a computer displaying the gene expression profile data.

In one embodiment, the invention provides a method for determining the similarity between the level of expression of one or more "RC Kinase" in a first cell, e.g., a cell of a subject, and that in a second cell, comprising obtaining the level of expression of one or more "RC Kinase" in a first cell and entering these values into a computer comprising a database including records comprising values corresponding to levels of expression of one or more "RC Kinase" in a second cell, and processor instructions, e.g., a user interface, capable of receiving a selection of one or more values for comparison purposes with data that is stored in the computer. The computer may further comprise a means for converting the comparison data into a diagram or chart or other type of output.

In another embodiment, values representing expression levels of "RC Kinase" are entered into a computer system, comprising one or more databases with reference expression levels obtained from more than one cell. For example, the computer comprises expression data of diseased and normal cells. Instructions are provided to the computer, and the computer is capable of comparing the data entered with the data in the computer to determine whether the data entered is more similar to that of a normal cell or of a diseased cell.

In another embodiment, the computer comprises values of expression levels in cells of subjects at different stages of COPD, and the computer is capable of comparing expression data entered into the computer with the data stored, and produce results indicating to which of the expression profiles in the computer, the one entered is most similar, such as to determine the stage of COPD in the subject.

In yet another embodiment, the reference expression profiles in the computer are expression profiles from cells of COPD of one or more subjects, which cells are treated in vivo or in vitro with a drug used for therapy of COPD. Upon entering of expression data of a cell of a subject treated in vitro or in vivo with the drug, the computer is instructed to compare the data entered to the data in the computer, and to provide results indicating whether the expression data input into the computer are more similar to those of a cell of a subject that is responsive to the drug or more similar to those of a cell of a subject that is not responsive to the drug. Thus, the results indicate whether the subject is likely to respond to the treatment with the drug or unlikely to respond to it.

In one embodiment, the invention provides a system that comprises a means for receiving gene expression data for one or a plurality of genes; a means for comparing the gene expression data from each of said one or plurality of genes to a common reference frame; and a means for presenting the results of the comparison. This system may further comprise a means for clustering the data.

In another embodiment, the invention provides a computer program for analyzing gene expression data comprising (i) a computer code that receives as input gene expression data for a plurality of genes and (ii) a computer code that compares said gene expression data from each of said plurality of genes to a common reference frame.

The invention also provides a machine-readable or computer-readable medium including program instructions for performing the following steps: (i) comparing a plurality of values corresponding to expression levels of one or more genes characteristic of COPD in a query cell with a database including records comprising reference expression or expression profile data of one or more reference cells and an annotation of the type of cell; and (ii) indicating to which cell the query cell is most similar based on similarities of expression profiles. The reference cells can be cells from subjects at different stages of COPD. The reference cells can also be cells from subjects responding or not responding to a particular drug treatment and optionally incubated in vitro or in vivo with the drug.

The reference cells may also be cells from subjects responding or not responding to several different treatments, and the computer system indicates a preferred treatment for the subject. Accordingly, the invention provides a method for selecting a therapy for a patient having COPD, the method comprising: (i) providing the level of expression of one or more genes characteristic of COPD in a diseased cell of the patient; (ii) providing a plurality of reference profiles, each associated with a therapy, wherein the subject expression profile and each reference profile has a plurality of values, each value representing the level of expression of a gene characteristic of COPD; and (iii) selecting the reference profile most similar to the subject expression profile, to thereby select a therapy for said patient. In a preferred embodiment step (iii) is performed by a computer. The most similar reference profile may be selected by weighing a comparison value of the plurality using a weight value associated with the corresponding expression data.

The relative abundance of an mRNA in two biological samples can be scored as a perturbation and its magnitude determined (i.e., the abundance is different in the two sources of mRNA tested), or as not perturbed (i.e., the relative abundance is the same). In various embodiments, a difference between the two sources of RNA of at least a factor of about 25% (RNA from one source is 25% more abundant in one source than the other source), more usually about 50%, even more often by a factor of about 2 (twice as abundant), 3 (three times as abundant) or 5 (five times as abundant) is scored as a perturbation. Perturbations can be used by a computer for calculating and expression comparisons.

Preferably, in addition to identifying a perturbation as positive or negative, it is advantageous to determine the magnitude of the perturbation. This can be carried out, as noted above, by calculating the ratio of the emission of the two fluorophores used for differential labeling, or by analogous methods that will be readily apparent to those of skill in the art.

The computer readable medium may further comprise a pointer to a descriptor of a stage of COPD or to a treatment for COPD.

In operation, the means for receiving gene expression data, the means for comparing the gene expression data, the means for presenting, the means for normalizing, and the means for clustering within the context of the systems of the present invention can involve a programmed computer with the respective functionalities described herein, implemented in hardware or hardware and software; a logic circuit or other component of a programmed computer that performs the operations specifically identified herein, dictated by a computer program; or a computer memory encoded with executable instructions representing a computer program that can cause a computer to function in the particular fashion described herein.

Those skilled in the art will understand that the systems and methods of the present invention may be applied to a variety of systems, including IBM-compatible personal computers running MS-DOS or Microsoft Windows.

The computer may have internal components linked to external components. The internal components may include a processor element interconnected with a main memory. The computer system can be an Intel Pentium®-based processor of 200 MHz or greater clock rate and with 32 MB or more of main memory. The external component may comprise a mass storage, which can be one or more hard disks (which are typically packaged together with the processor and memory). Such hard disks are typically of 1 GB or greater storage capacity. Other external components include a user interface device, which can be a monitor, together with an inputting device, which can be a "mouse", or other graphic input devices, and/or a keyboard. A printing device can also be attached to the computer.

Typically, the computer system is also linked to a network link, which can be part of an Ethernet link to other local computer systems, remote computer systems, or wide area communication networks, such as the Internet. This network link allows the computer system to share data and processing tasks with other computer systems.

Loaded into memory during operation of this system are several software components, which are both standard in the art and special to the instant invention. These software components collectively cause the computer system to function according to the methods of this invention. These software components are typically stored on a mass storage. A software component represents the operating system, which is responsible for managing the computer system and its network interconnections. This operating system can be, for example, of the Microsoft Windows' family, such as Windows 95, Windows 98, Windows NT or Windows XP. A software component represents common languages and functions conveniently present on this system to assist programs implementing the methods specific to this invention. Many high or low level computer languages can be used to program the analytic methods of this invention. Instructions can be interpreted during run-time or compiled. Preferred languages include C/C++, and JAVA®. Most preferably, the methods of this invention are programmed in mathematical software packages which allow symbolic entry of equations and high-level specification of processing, including algorithms to be used, thereby freeing a user of the need to procedurally program individual equations or algorithms. Such packages include Matlab from Mathworks (Natick, Mass.), Mathematica from Wolfram Research (Champaign, Ill.), or S-Plus from Math Soft (Cambridge, Mass.). Accordingly, a software component represents the analytic methods of this invention as programmed in a procedural language or symbolic package. In a preferred embodiment, the computer system also contains a database comprising values representing levels of expression of one or more genes characteristic of COPD. The database may contain one or more expression profiles of genes characteristic of COPD in different cells.

In an exemplary implementation, to practice the methods of the present invention, a user first loads expression profile data into the computer system. These data can be directly entered by the user from a monitor and keyboard, or from other computer systems linked by a network connection, or on removable storage media such as a CD-ROM or floppy disk or through the network. Next the user causes execution of expression profile analysis software which performs the steps of comparing and, e.g., clustering co-varying genes into groups of genes.

In another exemplary implementation, expression profiles are compared using a method described in U.S. Pat. No. 6,203,987. A user first loads expression profile data into the computer system Geneset profile definitions are loaded into the memory from the storage media or from a remote computer, preferably from a dynamic geneset database system, through the network. Next the user causes execution of projection software which performs the steps of converting expression profile to projected expression profiles. The projected expression profiles are then displayed.

In yet another exemplary implementation, a user first leads a projected profile into the memory. The user then causes the loading of a reference profile into the memory. Next, the user causes the execution of comparison software which performs the steps of objectively comparing the profiles.

3. Detection of Variant Polynucleotide Sequence

In yet another embodiment, the invention provides methods for determining whether a subject is at risk for developing a disease, such as a predisposition to develop COPD, for example COPD, associated with an aberrant activity of any one of the polypeptides encoded by any of the polynucleotides of the SEQ ID NO: 1, wherein the aberrant activity of the polypeptide is characterized by detecting the presence or absence of a genetic lesion characterized by at least one of these:

(i) an alteration affecting the integrity of a gene encoding a marker polypeptides, or (ii) the misexpression of the encoding polynucleotide.

To illustrate, such genetic lesions can be detected by ascertaining the existence of at least one of these:

I. a deletion of one or more nucleotides from the polynucleotide sequence
II. an addition of one or more nucleotides to the polynucleotide sequence
III. a substitution of one or more nucleotides of the polynucleotide sequence
IV. a gross chromosomal rearrangement of the polynucleotide sequence
V. a gross alteration in the level of a messenger RNA transcript of the polynucleotide sequence
VI. aberrant modification of the polynucleotide sequence, such as of the methylation pattern of the genomic DNA
VII. the presence of a non-wild type splicing pattern of a messenger RNA transcript of the gene
VIII. a non-wild type level of the marker polypeptide
IX. allelic loss of the gene
X. inappropriate post-translational modification of the marker polypeptide The present Invention provides assay techniques for detecting mutations in the encoding polynucleotide sequence. These methods include, but are not limited to, methods involving sequence analysis, Southern blot hybridization, restriction enzyme site mapping, and methods involving detection of absence of nucleotide pairing between the polynucleotide to be analyzed and a probe.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene in a subject can render the subject susceptible to developing a specific disease or disorder. Polymorphic regions in genes, can be identified, by determining the nucleotide sequence of genes in populations of individuals. If a polymorphic region is identified, then the link with a specific disease can be determined by studying specific populations of individuals, e.g. individuals which developed a specific disease, such as COPD. A polymorphic region can be located in any region of a gene, e.g., exons, in coding or non coding regions of exons, introns, and promoter region.

In an exemplary embodiment, there is provided a polynucleotide composition comprising a polynucleotide probe including a region of nucleotide sequence which is capable of hybridising to a sense or antisense sequence of a gene or naturally occurring mutants thereof, or 5' or 3' flanking sequences or intronic sequences naturally associated with the subject genes or naturally occurring mutants thereof. The polynucleotide of a cell is rendered accessible for hybridization, the probe is contacted with the polynucleotide of the sample, and the hybridization of the probe to the sample polynucleotide is detected. Such techniques can be used to detect lesions or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridising specifically to allelic variants are attached to a solid phase support, e.g., a "chip". Mutation detection analysis using these chips comprising oligonucleotides, also termed "DNA probe arrays" is described e.g., in Cronin et al. (119). In one embodiment, a chip comprises all the allelic variants of at least one polymorphic region of a gene. The solid phase support is then contacted with a test polynucleotide and hybridization to the specific probes is detected. Accordingly, the identity of numerous allelic variants of one or more genes can be identified in a simple hybridization experiment.

In certain embodiments, detection of the lesion comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) [Landegran et al., 1988, (120) and Nakazawa et al., 1994 (121)], the latter of which can be particularly useful for detecting point mutations in the gene; Abravaya et al., 1995, (122)]. In a merely illustrative embodiment, the method includes the steps of (i) collecting a sample of cells from a patient, (ii) isolating polynucleotide (e.g., genomic, mRNA or both) from the cells of the sample, (iii) contacting the polynucleotide sample with one or more primers which specifically hybridize to a polynucleotide sequence under conditions such that hybridization and amplification of the polynucleotide (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication [Guatelli, J. C. et al., 1990, (123)], transcriptional amplification system [Kwoh, D. Y. et al., 1989, (124)], Q-Beta replicase [Lizardi, P. M. et al., 1988, (125)], or any other polynucleotide amplification method, followed by the detection of the amplified molecules using techniques well known to those of skill in the art. These detection schemes are especially useful for the detection of polynucleotide molecules if such molecules are present in very low numbers.

In a preferred embodiment of the subject assay, mutations in, or allelic variants, of a gene from a sample cell are identified by alterations in restriction enzyme cleavage patterns. For example, sample and control DNA is isolated, amplified (optionally), digested with one or more restriction endonucleases, and fragment length sizes are determined by gel electrophoresis. Moreover, the use of sequence specific ribozymes (see, for example, U.S. Pat. No. 5,498,531) can be used to score for the presence of specific mutations by development or loss of a ribozyme cleavage site.

4. In Situ Hybridization

In one aspect, the method comprises in situ hybridization with a probe derived from a given marker polynucleotide, which sequence is selected from any of the polynucleotide sequences of the SEQ ID NO: 1, 2, 3, 4, 5, or 6 or a sequence complementary thereto. The method comprises contacting the labeled hybridization probe with a sample of a given type of tissue from a patient potentially having COPD and COPD in particular as well as normal tissue from a person with no COPD, and determining whether the probe labels tissue of the patient to a degree significantly different (e.g., by at least a factor of two, or at least a factor of five, or at least a factor of twenty, or at least a factor of fifty) than the degree to which normal tissue is labeled.

Therapeutic Indications and Methods

The human RC Kinase disclosed herein is likely to be useful for the same purposes as previously identified serine/threonine kinases, or more specifically for the same purposes as previously identified MAPK kinase kinases. For example, transforming growth factor type beta (TGF-β) regulates the proliferation and differentiation of a variety of cell types binding to and activating cell surface receptors which possess serine/threonine kinase activity. Atfi et al. (*Proc. Natl. Acad. Sci. U.S.A.* 92, 12110-04, 1995) have shown that TGF-β activates a 78-kDa protein (p78) serine/threonine kinase; the p78 kinase was activated only in cells for which TGF-β acts as a growth inhibitory factor. Another example is MAPKKK3, the human kinase to which RC Kinase is most closely related. MAPKKK3 is known to directly regulate the stress-activated protein kinase (SAPK) and extracellular signal-regulated protein kinase (ERK) pathways by activating SEK and MEK1/2 respectively. It can also enhance transcription from a nuclear factor kappa-B (NFκB)-dependent reporter gene. Other previously identified MAPK kinase kinases include c-Raf, Mos, MEKK1, B-Raf, TAK1, A-Raf, Tpl-2, MRKK2, MUK, SPRK, MAPKKK5, MEKK4, and MST. The human RC Kinase disclosed herein also may be involved in such signaling. Thus, regulation of its activity can be used to treat disorders in which such signaling is defective or dysregulated.

Expression profiling of RC Kinase showed that it is expressed highly in the lung and trachea, and that it can be found to be expressed in activated B cells and other leukocytes. Some of the ESTs which are expressed from human RC Kinase, e.g., GenBank accession numbers BU676900, B0484791, CA311871, BQ045211, and BM969829, are also expressed in the lung epithelial cells and in primary lung cystic fibrosis epithelial cells. Furthermore, microarray analysis comparing lungs from patients with chronic obstructive pulmonary disease (COPD) and lungs from normal lungs showed that RC Kinase is upregulated an average of 4.58 fold in the COPD lungs (FIG. 1). Thus, human RC Kinase could be a potential target for treating lung disease, such as COPD.

COPD is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659-681, 1998; Barnes, Chest 117, 10S-14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

The expression of RC Kinase in cell increase significantly after treatment of the cells with 95 nM potassium chloride (KCl), which subjects the cells to a hyperosmotic stress. Additionally, some cell lines increase its expression of RC Kinase in response to 500 μm hydrogen peroxide ($H_2O_2$), a treatment which subjects the cells to an oxidative stress and which has been reported to impair the capacity of B cells to stimulate specific T cells. Such upregulation of RC Kinase in the cell lines in response to hyperosmotic and oxidative stress suggests that higher expression of RC Kinase in the lungs of COPD patients may be the result of cellular stresses caused by the irritants in tobacco smoke or stresses caused by the inflammatory response to those irritants.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as tobacco smoke, activate macrophages which are resident in the respiratory tract, as well as epithelial cells leading to release of chemokines (e.g., interleukin-8) and other chemotactic factors. These chemotactic factors act to increase the trafficking of neutrophils, monocytes, and lymphocytes from the blood into the lung tissue and airways. $CD8^+$ lymphocytes recruited into the airways can recognize proteins that have been altered by inhaled chemicals, such as tobacco smoke, and induce apoptosis of the cells expressing such altered proteins. The lymphocytes can also release inflammatory mediators to recruit other leukocytes to the lungs. Apoptotic cells killed by the lymphocytes can additionally release proteolytic enzymes. Neutrophils and monocytes recruited into the airways can release a variety of potentially damaging mediators such as proteolytic enzymes and reactive oxygen species. Although not as well studied, B cells have also been found in increased numbers in the lungs of smokers with airway obstruction, particularly within lymphoid nodules that develop in the airway adventitia (Bosken, C H et al., *Am Rev Respir Dis.,* 145(4 Pt 1):911-7, 1992). The B cells may play roles in antigen presentation, inflammatory cytokine production, and the generation of antibodies such as IgE and IgA that target, promote, and maintain the immune response in the lungs of COPD sufferers. Matrix degradation and emphysema, along with airway wall thickening, surfactant dysfunction, and mucus hypersecretion, all are potential sequelae of this inflammatory response that lead to impaired airflow and gas exchange.

RC Kinase has the ability to phosphorylate the MAP kinase kinase MKK4, and to a lesser extent, the MAP kinase kinase MKK6, indicating that RC Kinase is an upstream activator in one or more MAP kinase signaling cascades. As described above, the activation of MAP kinase signaling cascades has many cellular consequences, including cell proliferation, differentiation, adaptation to environmental stress, cytokine production, and apoptosis. The activation of MKK4 has been shown in many cases to lead to the phosphorylation of JNK-type MAP kinases, which in turn can activate c-Jun, a component of the AP-1 transcription factor complex. JNK-type MAP kinases are also known to inhibit NFAT transcription factors. In addition, other MAPK kinase kinases, such as MEKK1, that are initiators of the signaling cascades that result in the phosphorylation of JNK-type MAP kinases, have been found to be able to activate the transcription factor NFκB, indicating that this transcription factor is also a downstream target of these cascades. Activation of MKK6, on the other hand, leads to the phosphorylation of p38-type MAP kinases, which are known to be important in the activation of the immune response and are key regulators of inflammatory cytokine expression.

RC Kinase appears to be upregulated and possibly activated by cellular stress, then phosphorylates MKK4 (and to a lesser extent MKK6), which leads to the activation of transcription factors AP-1 and NFκB. As a result of activation of this signaling cascade, Interleukin-8 production is increased and leads to the recruitment of inflammatory cells, such as neutrophils, that play a role in the pathology of COPD. The occurrence of cellular stress, the activation of the transcription factors AP-1 and NFκB, and the overproduction of Interleukin-8 are characteristic of numerous inflammatory diseases, many of which may be treated or prevented through the regulation of RC Kinase. Such diseases include asthma; allergic rhinitis; atopic dermatitis; hives; conjunctivitis; vernal catarrh; chronic arthrorheumatism; systemic lupus erythematosus; psoriasis; diabrotic colitis; systemic inflammatory response syndrome (SIRS); sepsis; polymyositis; dermatomyositis (DM); Polyaritis nodoa (PN); mixed connective tissue disease (MCTD); Sjoegren's syndrome; and gout.

Human RC Kinase ESTs, e.g., GenBank accession number BI832332, BX090530, N47620, and N57475, also are expressed in normal brain medulla and in multiple sclerosis lesions in the central nervous system. Thus, human RC Kinase could be a potential target for treating multiple sclerosis and other central nervous system disorders.

Human RC Kinase ESTs, e.g., GenBank accession number AI683447, also are expressed in well-differentiated endometrial adenocarcinoma. Thus, human RC Kinase could be a potential target for treating cancers. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects RC Kinase activity can be administered to a human cell, either in vitro or in vivo, to reduce RC Kinase activity. The reagent preferably binds to an expression product of a human RC Kinase gene. If the expression product is a polypeptide, the reagent is preferably an antibody. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmol of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202-05 (1993); Chiou et al., Gene Therapeutics: Methods and Applications of Direct Gene Transfer (J. A. Wolff, ed.) (1994); Wu & Wu, *J. Biol. Chem.* 263, 621-24 (1988); Wu et al., *J. Biol. Chem.* 269, 542-46 (1994); Zenke et al., *Proc. Natl. Acad. Sci. U.S.A.* 87, 3655-59 (1990); Wu et al., *J. Biol. Chem.* 266, 338-42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEMO or calcium phosphate-mediated transfection.

Determination of a Therapeutically Effective Dose

The determination of a therapeutically effective dose is well within the capability of those skilled in the art. A therapeutically effective dose refers to that amount of active ingredient which increases or decreases extracellular matrix degradation relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 μgrams, up to a total dose of about 1 μg, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 μg to about 50 μg/kg, about 50 μg to about 5 mg/kg, about 100 μg to about 500 μg/kg of patient body weight, and about 200 to about 250 μg/kg of patient body weight. For administration of polynucleotides encoding single-chain antibodies, effective in vivo dosages are in the range of about 100 ng to about 200 ng, 500 ng to about 50 mg, about 1 μg to about 2 mg, about 5 μg to about 500 μg, and about 20 μg to about 100 μg of DNA.

If the expression product is mRNA, the reagent is preferably an antisense oligonucleotide or a ribozyme. Polynucleotides which express antisense oligonucleotides or ribozymes can be introduced into cells by a variety of methods, as described above.

Preferably, a reagent reduces expression of a RC Kinase polynucleotide or activity of a RC Kinase polypeptide by at least about 10, preferably about 50, more preferably about 75, 90, or 100% relative to the absence of the reagent. The effectiveness of the mechanism chosen to decrease the level of expression of a RC Kinase polynucleotide or the activity of a RC Kinase polypeptide can be assessed using methods well known in the art, such as hybridization of nucleotide probes to RC Kinase-specific mRNA, quantitative RT-PCR, immunologic detection of a RC Kinase polypeptide, or measurement of RC Kinase activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents and patent applications cited in this disclosure are expressly incorporated herein. A more complete understanding can be obtained by reference to the following specific examples which are provided for purposes of illustration only and are not intended to limit the scope of the invention.

Example 1

Detection of RC Kinase Activity

Figure 8:
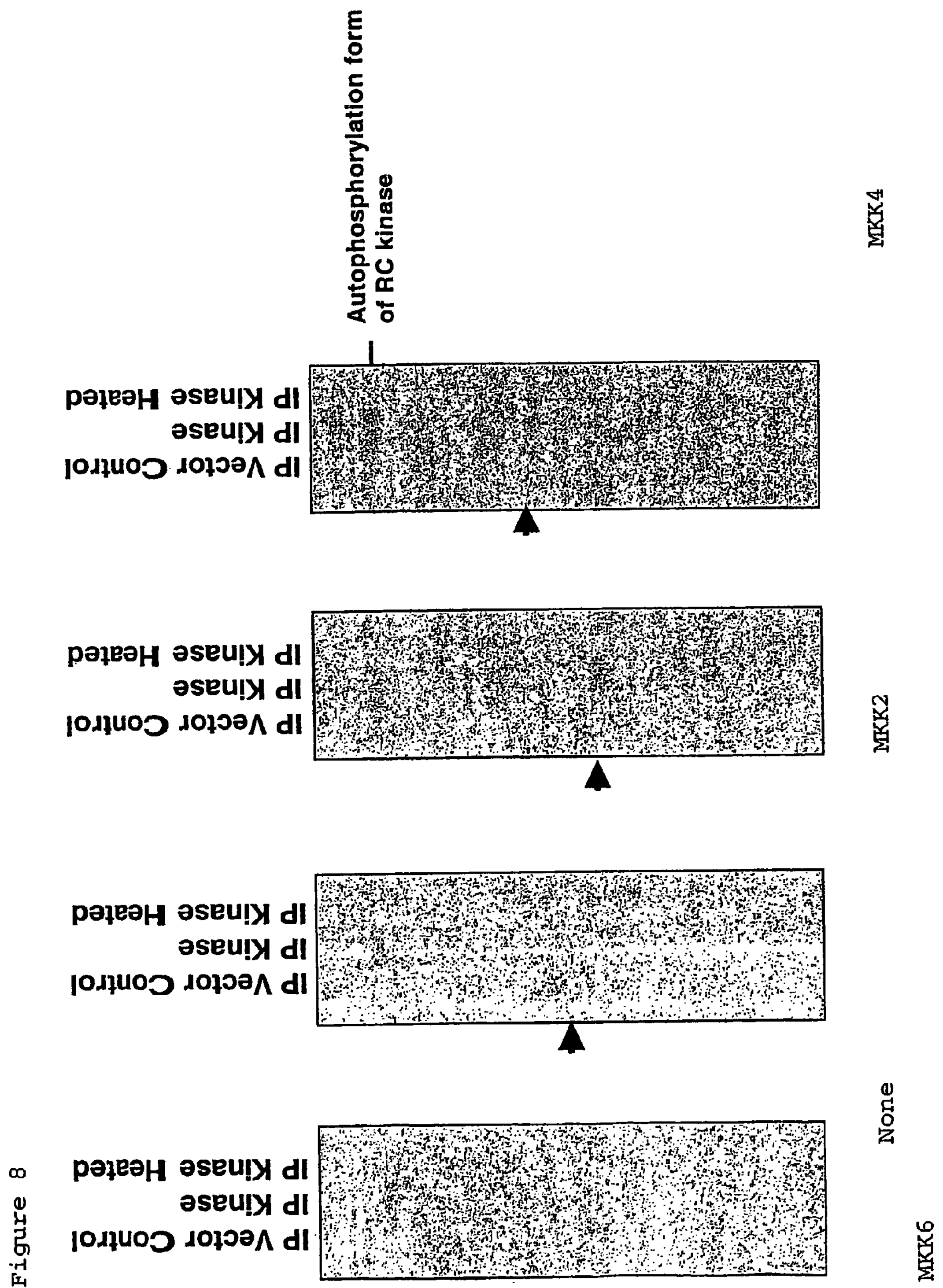
FIG. 8 shows the phosphorylating activity of human RC Kinase on various MAP Kinase Kinases tested as substrates. RC Kinase was able to phosphorylate itself and MKK4, but showed only minor activity against MKK6 and no detectable activity against MEK2. RC Kinase was prepared by immunoprecipitation of lysates of RC Kinase transfectants, then added to a mixture of substrate and [$^{33}$P]-ATP. Phosphorylation activity was detected by autoradiography after incubation and size separation on SDS-PAGE. As controls, immunoprecipitate from an empty vector-transfectant and heat-inactivated immunoprecipitate from an RC Kinase transfectant were used.

For high level expression of a FLAG-tagged RC Kinase polypeptide, HEK293 cells were transfected with the expression vector pcDNA3.1-RC Kinase polypeptide (expressing the DNA-sequence of ID NO: 1 with a FLAG epitope sequence at its amino terminal) using the transfection reagent Polyfect (Qiagen). The cells were harvested 48 h after infection and lysed in 50 mM Tris, pH 7.4, 150 mM NaCl, 1 mM EDTA, 1% Triton X, 1 mM NaF, 1 mM $Na_3VO_4$, and Proteinase Inhibitor Cocktail (Roche). RC Kinase polypeptide was then immunoprecipitated from the lysate using anti-FLAG antibodies. An in vitro kinase assay was performed in a volume of 40 μl with immunoprecipitated FLAG-RC Kinase polypeptide in 50 mM Tris-HCl, pH 8.0, 50 mM NaCl, 5 mM $MgCl_2$, 1 mM dithiothreitol. The reaction is started by the addition of 4 μl of 1 mM ATP supplemented with 5 μCi of (-$^{32}$P)ATP and incubated for 30 min at 37° C. Afterward, the samples were subjected to SDS-PAGE and phosphorylated proteins were detected by autoradiography. Histone H1, myelin basic protein, MEK2, MKK4, and MKK6 were tested as substrates. It was shown that the polypeptide with the amino acid sequence of SEQ ID NO: 7 has RC Kinase activity, specifically that it has the ability to phosphorylate other RC Kinase polypeptides, MKK4, and MKK6. (FIG. 8)

Example 2

Identification of a Test Compound which Binds to a RC Kinase Polypeptide

Purified RC Kinase polypeptides comprising a glutathione-S-transferase protein and absorbed onto glutathione-derivatized wells of 96-well microtiter plates are contacted with test compounds from a small molecule library at pH 7.0 in a physiological buffer solution. RC Kinase polypeptides comprise, an amino acid sequence shown in SEQ ID NOS: 2, 5, 6, or 7. The test compounds comprise a fluorescent tag. The samples are incubated for 5 minutes to one hour. Control samples are incubated in the absence of a test compound.

The buffer solution containing the test compounds is washed from the wells. Binding of a test compound to a RC Kinase polypeptide is detected by fluorescence measurements of the contents of the wells. A test compound which increases the fluorescence in a well by at least 15% relative to fluorescence of a well in which a test compound was not incubated is identified as a compound which binds to a RC Kinase polypeptide.

Example 3

Identification of a Test Compound which Decreases RC Kinase Activity

RC Kinase polypeptides, purified as described in Example 1, are contacted with test compounds from a small molecule library and assayed for RC Kinase activity using any of the substrates mentioned in Example 1 or other substrates of RC Kinase. As controls, RC Kinase polypeptides in the absence of a test compound also are assayed. Kinase activity is measured as described in Example 1 or as taught in Trost et al., *J. Biol. Chem.* 275, 7373-77, 2000; Hayashi et al., *Biochem. Biophys. Res. Commun.* 264, 449-56, 1999; Masure et al., *Eur. J. Biochem* 265, 353-60, 1999; and Mukhopadhyay et al., *J. Bacteriol.* 181, 6615-22, 1999.

Alternatively, RC Kinase activity can be measured indirectly by measuring downstream effects, for example, by assaying NFκB or AP-1 reporter gene activity in RC Kinase expressing cells, or by assaying Interleukin-8 production by RC kinase expressing cells. For example, Mercury™ Pathway Profiling Luciferase System 2 (CLONTECH) reporter genes can be used by transfecting cells as well as RC Kinase expression vector. Since in the presence of AP-1 or NFκB reporter as well as RC Kinase in transfected cell show strong Luciferase activity, these cells can monitor the efficacy of a compound whether it inhibit RC Kinase or not by measuring its reporter activity indirectly. RC Kinase expressing cells are contacted with test compounds from a small molecule library and assayed for Interleukin-8 production is also able to monitor RC Kinase activity indirectly. As controls, the same assays are conducted in the absence of test compounds.

A test compound which decreases RC Kinase activity relative to the control by at least 20% is identified as a RC Kinase inhibitor.

Example 4

Identification of a Test Compound which Decreases RC Kinase Gene Expression

A test compound is administered to a culture of cells transfected with an expression construct which expresses RC Kinase and incubated at 37° C. for 10 to 45 minutes. A culture of the same type of cells incubated for the same time without the test compound provides a negative control.

RNA is isolated from the two cultures as described in Chirgwin et al., *Biochem* 18, 5294-99, 1979). Northern blots are prepared using 20 to 30 μg total RNA and hybridized with a $^{32}$P-labeled RC Kinase-specific probe at 65° C. in Express-hyb (CLONTECH). The probe comprises at least 11 contiguous nucleotides selected from the complement of SEQ ID NO: 1, 2, 3, 4, 5, or 6. A test compound which decreases the RC Kinase-specific signal relative to the signal obtained in the absence of the test compound is identified as an inhibitor of RC Kinase gene expression.

Example 5

Treatment of Chronic Obstructive Pulmonary Disease with a Reagent which Specifically Binds to a RC Kinase Gene Product Synthesis of antisense RC Kinase oligonucleotides comprising at least 11 contiguous nucleotides selected from the complement of SEQ ID NO: 1, 2, 3, 4, 5, or 6 is performed on a Pharmacia Gene Assembler series synthesizer using the phosphoramidite procedure Neumann et al., *Chem. Rev.* 90, 534-83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the *Limulus* Amebocyte Assay (Bang, *Biol. Bull* (Woods Hole, Mass.) 105, 361-362, 1953).

An aqueous composition containing the antisense oligonucleotides at a concentration of 0.1-100 μM is administered intrabronchially to a patient with chronic obstructive pulmonary disease. The severity of the disease is suppressed due to decreased RC Kinase activity.

Example 6

Disease-Specific Expression of RC Kinase Detected by Microarray Analysis

Target Preparation

Human total RNA was prepared from frozen lung tissue obtained from four normal individuals and three individuals diagnosed with chronic obstructive pulmonary disease (Analytical Biological Services Inc. Wilmington, Del., USA) using Trizol™ (Invitrogen Corp., Carlsbad, Calif., USA). Five micrograms of each of the total RNAs was added to a reaction mix in a final volume of 12 μl, containing bacterial control mRNAs (2.5 pg/μl araB/entF, 8.33 pg/μl fixB/gnd and 25 pg/μl hisB/leuB) and 1.0 μl of 0.5 pmol/μl T7-$(dT)_{24}$ oligonucleotide primer. The mixture was incubated for 10 min at 70° C. and chilled on ice. With the mixture remaining on ice, 4 μl of 5× first-strand buffer, 2 μl 0.1 M DTT, 1 μl of 10 mM dNTP mix and 1 μl Superscript™ II RNase H— reverse transcriptase (200 U/μl) was added to make a final volume of 20 μl, and the mixture incubated for 1 h in a 42° C. water bath. Second-strand cDNA was synthesized in a final volume of 150 μl, in a mixture containing 30 μl of 5× second-strand buffer, 3 μl of 10 mM dNTP mix, 4 μl of *Escherichia coli* DNA polymerase I (10 U/μl) and 1 μl of RNase H (2 U/μl) for 2 h at 16° C. The cDNA was purified using a Qiagen QIAquick purification kit, dried down, and resuspended in IVT reaction mix, containing 3.0 μl nuclease-free water, 4.0 μl 10× reaction buffer, 4.0 μl 75 mM ATP, 4.0 μl 75 mM GTP, 3.0 μl 75 mM CTP, 3.0 μl 75 mM UTP, 7.5 μl 10 mM Biotin 11-CTP, 7.5 μl 10 mM Biotin 11-UTP (PerkinElmer Life Sciences Inc. Boston, Mass., USA) and 4.0 μl enzyme mix. The reaction mix was incubated for 14 h at 37° C. and cRNA target purified using an RNeasy® kit (Qiagen). cRNA yield was quantified by measuring the UV absorbance at 260 nm, and fragmented in 40 mM Tris-acetate (TrisOAc) pH 7.9, 100 mM KOAc and 31.5 mM MgOAc, at 94° C. for 20 min. This results typically in a fragmented target with a size range between 100 and 200 bases.

Array Hybridization

Ten micrograms of fragmented target cRNA was used for hybridization of each UniSet Human I Expression Bioarray chip (AmershamBiosciences), in 260 μl of hybridization solution containing 78 μl Amersham Hyb buffer component A and 130 μl Amersham Hyb buffer component B. The hybridization solution was heated at 90° C. for 5 min to denature the cRNA and chilled on ice. The sample was vortexed for 5 s at maximum speed, and 250 μl injected into the inlet port of the hybridization chamber. The slides were loaded into a ISF-4-W shaking incubator (Kuhner, Birsfelden, Switzerland), with the hybridization chambers facing up. Slides were incubated for 24 h at 37° C., while shaking at 300 r.p.m.

Post-Hybridization Processing Using Streptavidin-Cy5

The slides were removed from the ISF-4-W shaker, and the hybridization chamber removed from each slide. Each slide was briefly rinsed in TNT buffer (0.1 M Tris-HCl pH 7.6, 0.15 M NaCl, 0.05% Tween-20) at room temperature, and then washed in TNT buffer at 42° C. for 60 min. The signal was developed using a 1:500 dilution of streptavidin-Cy5 (AmershamBiosciences), for 30 min at room temperature. Excess dye was removed by washing four times with TNT buffer, for 5 min each, at room temperature. Slides were rinsed in 0.05% Tween-20 and dried under nitrogen gas. Processed slides were scanned using an Axon GenePix 4000B Scanner with the laser set to 635 nm, the photomultiplier tube (PMT) voltage to 600 and the scan resolution to 10 μm. Images were acquired with the Axon GenePixPro v4.0 Scanning Software (AmershamBiosciences), and analyzed using the CodeLink™ Expression Analysis Software (AmershamBiosciences).

Data Analysis

CodeLink™ Expression Analysis Software (AmershamBiosciences) automatically creates signal data for each spotted dot as a Microsoft Excel formatted spreadsheet. The data was then compared using the computer program Spotfire Decision Site 7.0 (Spotfire Japan K.K., Tokyo, Japan) to determine the fold difference between each gene in normal and COPD lung. As a result of this analysis, the RC Kinase gene transcript was found to be expressed higher in COPD than in normal lung (FIGS. 1, 2).

Example 7

Tissue-Specific Expression of RC Kinase

The qualitative expression pattern of RC Kinase in various tissues is determined by Reverse Transcription-Polymerase Chain Reaction (RT-PCR).

To demonstrate that RC Kinase is involved in the disease process of COPD, 25 μg of total RNA from the following sources were used as template in reactions to synthesize first-strand cDNA for expression profiling: Human Total RNA Panel I-V (Clontech Laboratories, Palo Alto, Calif., USA), normal human lung primary cell lines (BioWhittaker Clonetics, Walkersville, Md., USA), human umbilical vein endothelial cells (HUVECs) (Kurabo, Osaka, Japan), several common cell lines (ATCC, Washington, D.C.), and various cells purified from peripheral blood. First-strand cDNA was synthesized using oligo (dT) (Nippon Gene Research Laboratories, Sendai, Japan) and the SUPERSCRIPT™ First-Strand Synthesis System for RT-PCR (Life Technologies, Rockville, Md.) according to the manufacturer's protocol. For these samples, $1/1250^{th}$ of the synthesized first-strand cDNA was subsequently used as template for quantitative PCR. Additional samples were purchased as presynthesized cDNAs (Human Immune System MTC Panel and Human Blood Fractions MTC Panel, Clontech Laboratories), and for these, 10 ng of cDNA was used as template for quantitative PCR.

Quantitative PCR was performed in a LightCycler (Roche Molecular Biochemicals, Indianapolis, Ind.) with oligonucleotide primers 5'-AATGGCACCCACAGTGACATGCTT-3' (SEQ ID NO: 13) and 5'-CCCTCGGTGTGTGCCCGATGTAAAA-3' (SEQ ID NO: 14) in the presence of the DNA-binding fluorescent dye SYBR Green I. Results were then converted into copy numbers of the gene transcript per ng of template cDNA by fitting to a standard curve. The standard curve was derived by simultaneously performing the quantitative PCR reaction on PCR products of known concentrations amplified beforehand from the target gene.

Figure 4:
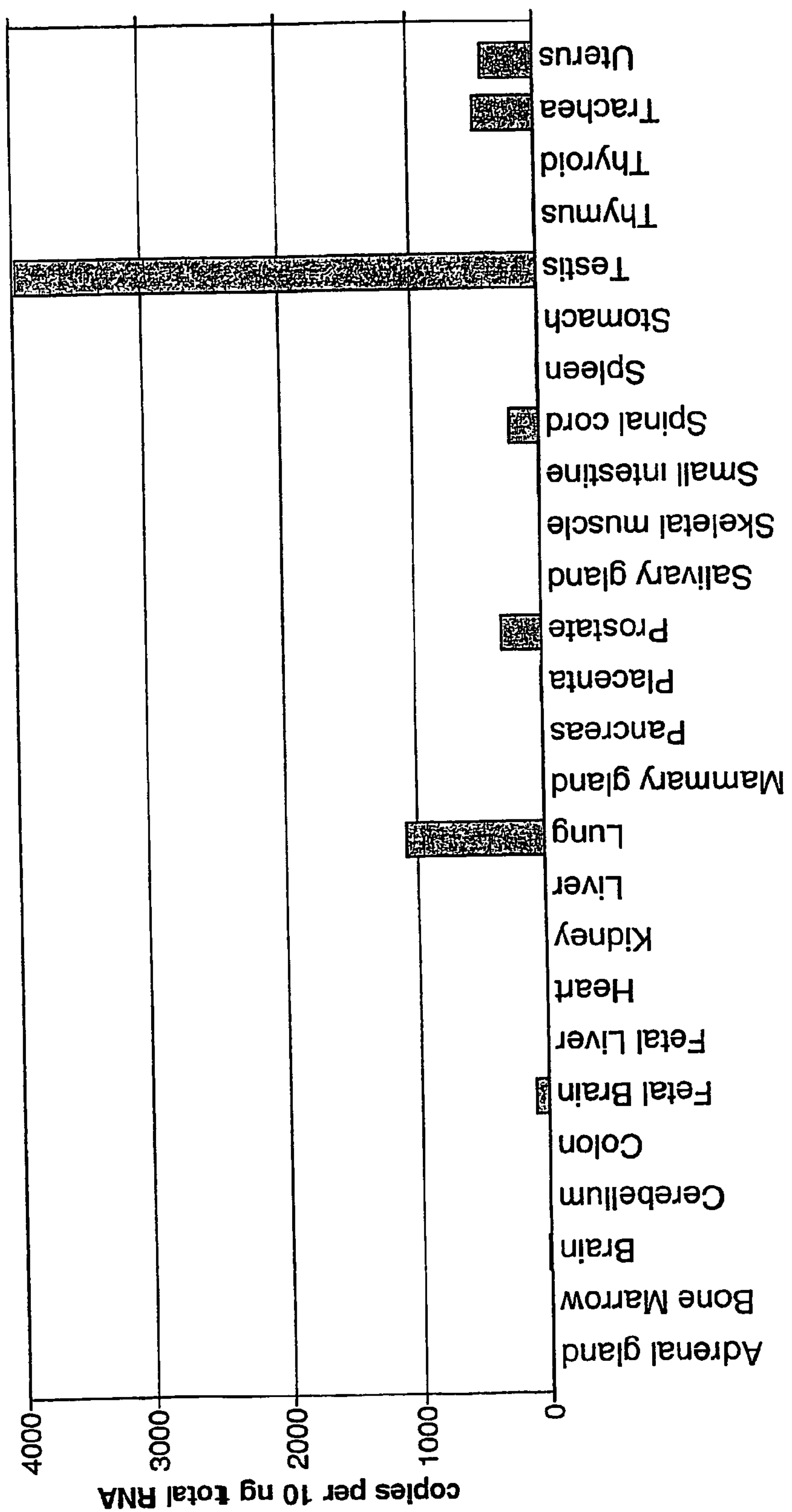
FIG. 4 shows the quantitative RT-PCR expression profiles of human RC Kinase in various tissues.
Figure 5:
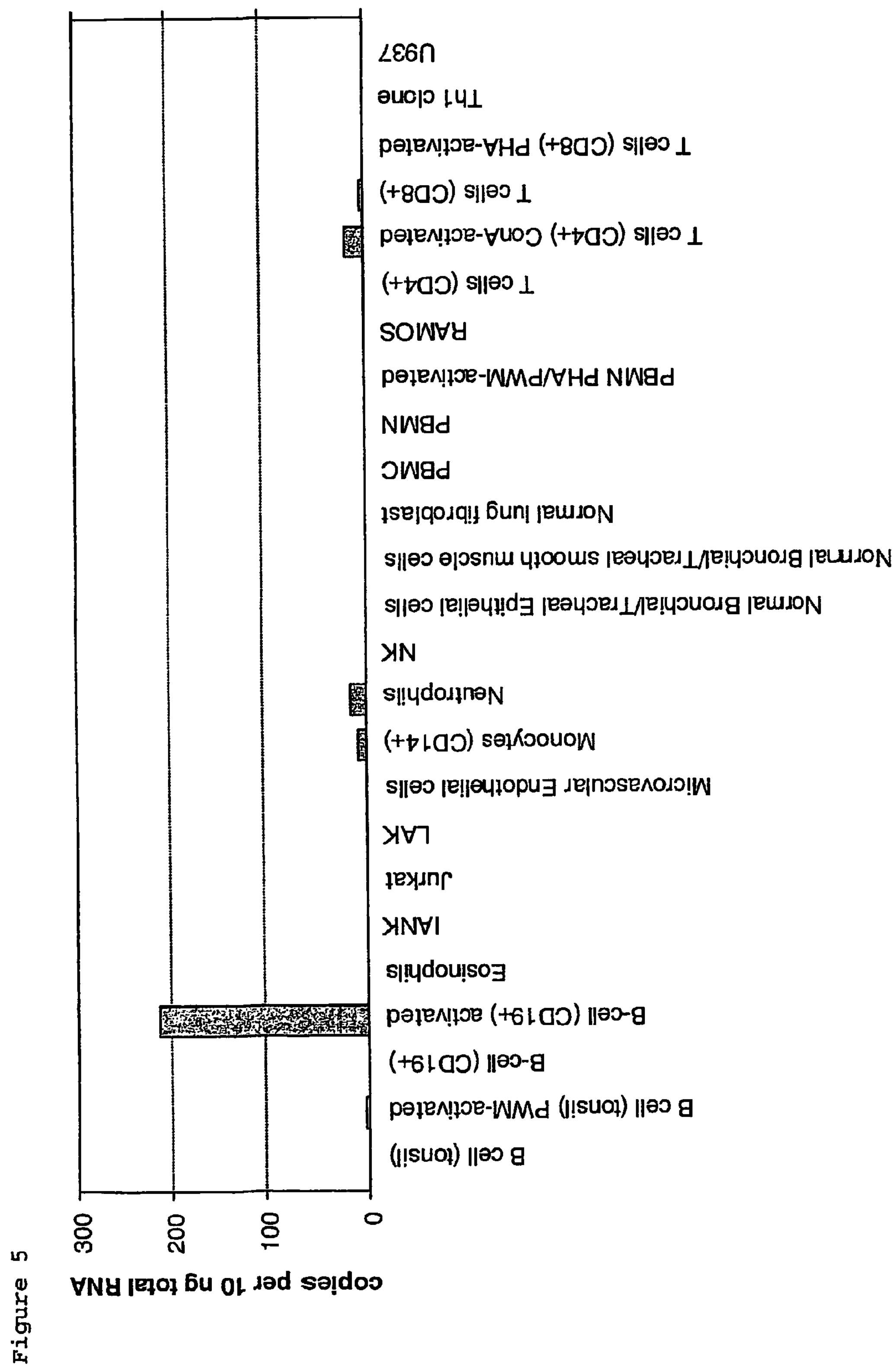
FIG. 5 shows the quantitative RT-PCR expression profiles of human RC Kinase in various immune related cells, primary lung cell lines, and immortalized cell lines.

To correct for differences in mRNA transcription levels per cell in the various tissue types, a normalization procedure was performed using similarly calculated expression levels of five different housekeeping genes: glyceraldehyde-3-phosphatase (GAPDH), hypoxanthine guanine phosphoribosyl transferase (HPRT), beta-actin, porphobilinogen deaminase (PBGD), and beta-2-microglobulin. The level of housekeeping gene expression is considered to be relatively constant for all tissues (Adams et al., 1993, Adams et al., 1995, Liew et al., 1994) and therefore can be used as a gauge to approximate relative numbers of cells per ng of cDNA template. Expression levels of the five housekeeping genes in all tissue samples were measured in three independent reactions per gene using the LightCycler and a constant amount (25 μg) of starting RNA. The calculated copy numbers for each gene, derived from comparison with simultaneously reacted standards of known concentrations, were recorded and converted into a percentage of the sum of the copy numbers of the gene in all tissue samples. For each tissue sample, the sum of the percentage values for each gene was calculated, and a normalization factor was calculated by dividing the sum-percentage value for each tissue by the sum percentage value of one of the tissues arbitrarily selected as a standard. To normalize an experimentally obtained value for the expression of a particular gene in a tissue sample, the obtained value was multiplied by the normalization factor for the tissue tested. This normalization method was used for all tissues except those derived from the Human Blood Fractions MTC Panel, which were normalized against the single housekeeping gene, beta-2-microglobulin, due to wide variation in other housekeeping gene expression in these tissues depending on activation status. The results of this expression profiling are given in FIG. 4 and FIG. 5, showing the normalized values for the copy numbers of mRNA per 10 ng of first-strand cDNA in each sample tested.

Figure 3:
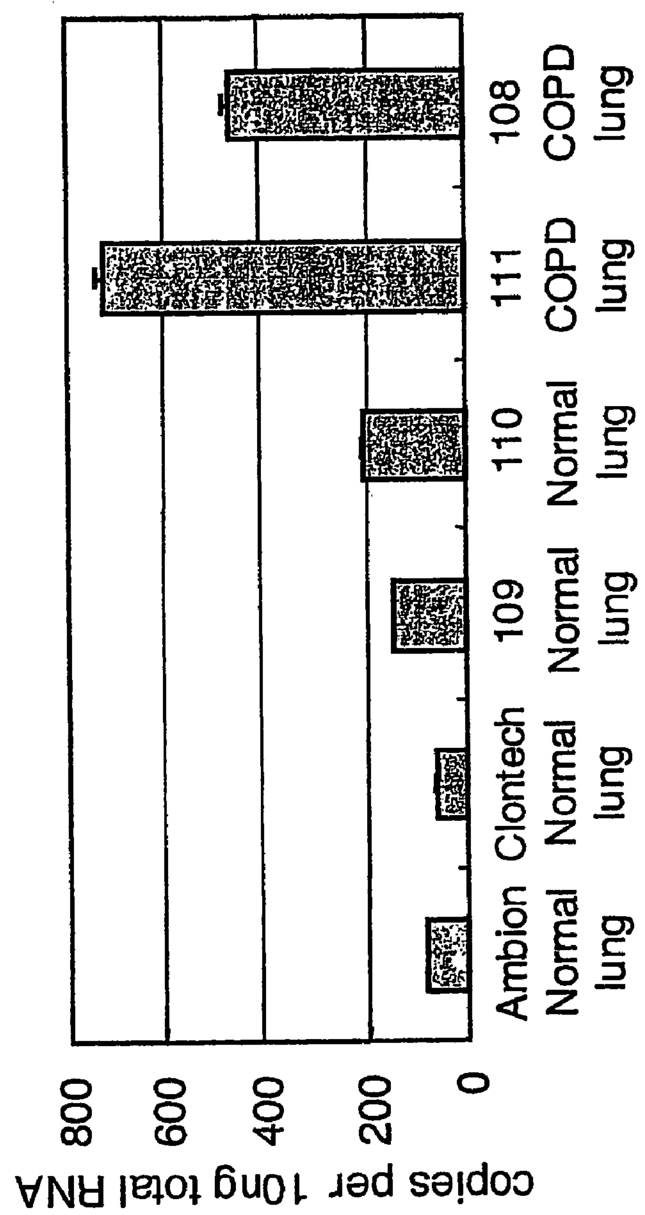
FIG. 3 shows confirmation by quantitative RT-PCR of the relative expression levels of RC Kinase in normal and COPD lung. The results, generated on the same set of tissues as used in the microarray analysis, correlate well with the microarray experiment results shown in FIG. 2.

To measure the relative copy numbers of the genes in patient samples and healthy lung samples, total RNA was prepared from frozen lung tissue obtained from four normal individuals and two individuals diagnosed with chronic obstructive pulmonary disease (Analytical biological Services Inc. Wilmington, Del., USA) using Trizol™ (Invitrogen Corp., Carlsbad, Calif., USA). cDNA was then synthesized as above and used as template for quantitative PCR as described above. Normalization was performed using the single housekeeping gene GAPDH. The different levels of expression of the RC Kinase gene transcript between the normal and COPD lung tissue samples are shown in FIG. 3, which displays the ratio of RC Kinase transcript to GAPDH transcript measured in each sample tested.

Example 8

Cloning of the RCKinase cDNA

Due to discrepancies between the nucleotide sequence of RC Kinase available in public databases (GenBank accession number NM_025052, length 2022 bp), and ESTs matching to this gene locus, an attempt was made to obtain the correct full-length sequence using RACE (rapid amplification of cDNA ends). RACE templates for this purpose were synthesized from human lung tissue using the GeneRacer™ kit (Invitrogen Corp., Carlsbad, Calif., USA). PCR amplification of the RC Kinase cDNA was then carried out using the gene-specific oligonucleotide primer 5'-CCCTCGGTGTGCTCCGATGTAAAA-3' (SEQ ID NO: 14) and the GeneRacer 5' primer included in the kit. The PCR amplification generated a product of approximately 5 kilobases in length, indicating a significantly longer transcript than that registered in the GenBank database.

To amplify the full-length sequence of RC Kinase, PCR primers were designed within predicted upstream exons and downstream exons of the RC Kinase gene. The upstream exons were predicted by aligning the mouse ortholog of RC Kinase, generated by the gene prediction program GenomeScan and registered in GenBank with the accession number XM_136210, with the genomic locus of human RC Kinase. Regions of alignment were considered to be potential exons of the human gene. Downstream exons were predicted by alignment of ESTs with the genomic locus and selecting the 3'-most regions of alignment. Primers used for amplification of the full-length sequence of RC Kinase were 5'-TTCAAAGAAACAGCAGCTTTTGGACATT-3' (SEQ ID NO: 15) and 5'-GCATCTGCAGTGGAACTGGGAAGAA-3' (SEQ ID NO: 16).

PCR products were cloned into a pCR4-TOPO sequencing vector (Invitrogen, Carlsbad, Calif.), cycle-sequenced with an ABI Prism Dye Terminator Cycle Sequencing Reaction Kit (Applied Biosystems, Foster City, Calif.), and analyzed on an ABI Prism 377 sequencing system (Applied Biosystems).

Example 9

Figure 6:
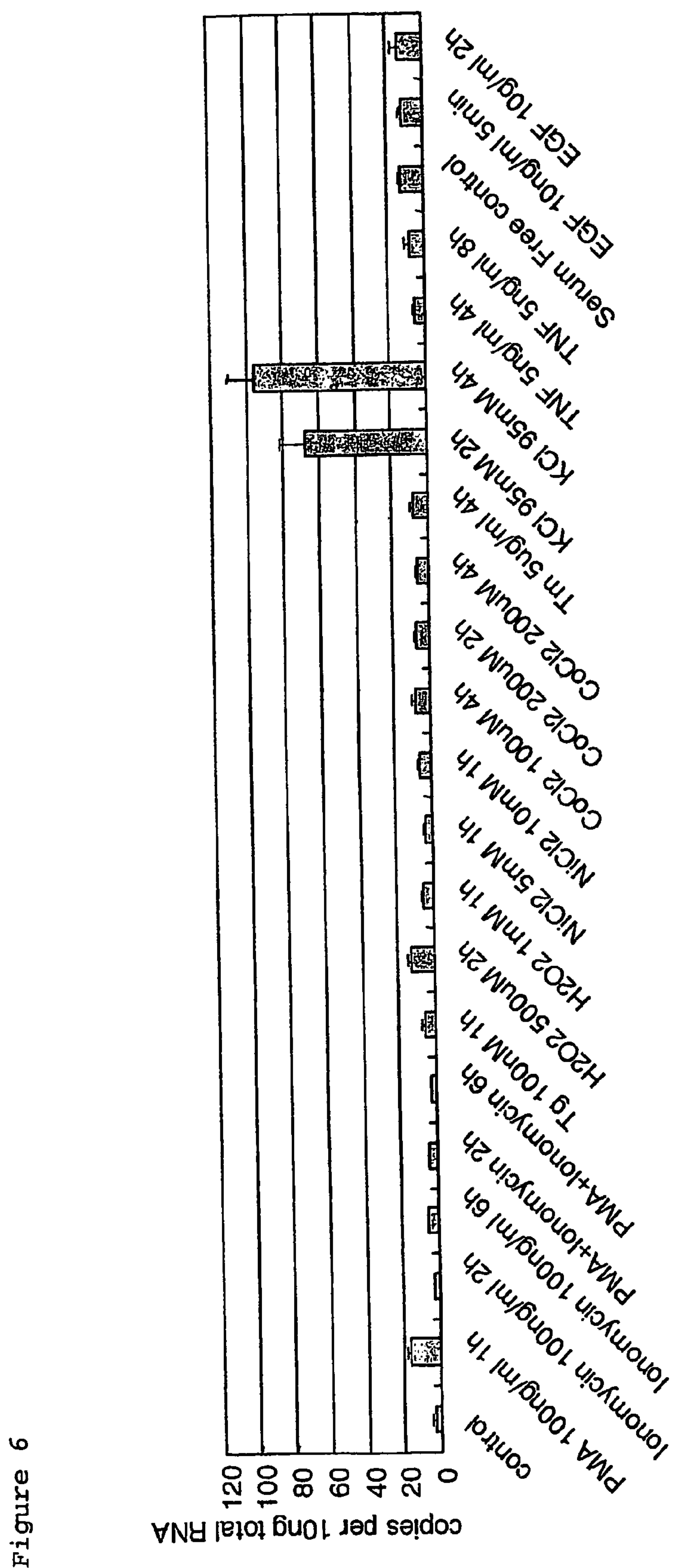
FIG. 6 shows changes in the expression level of human RC Kinase in the HEK293 cell line in response to treatment with various stimuli that cause cell growth or cellular stress. RC Kinase expression is upregulated after stimulation with 95 mM KCl.
Figure 7:
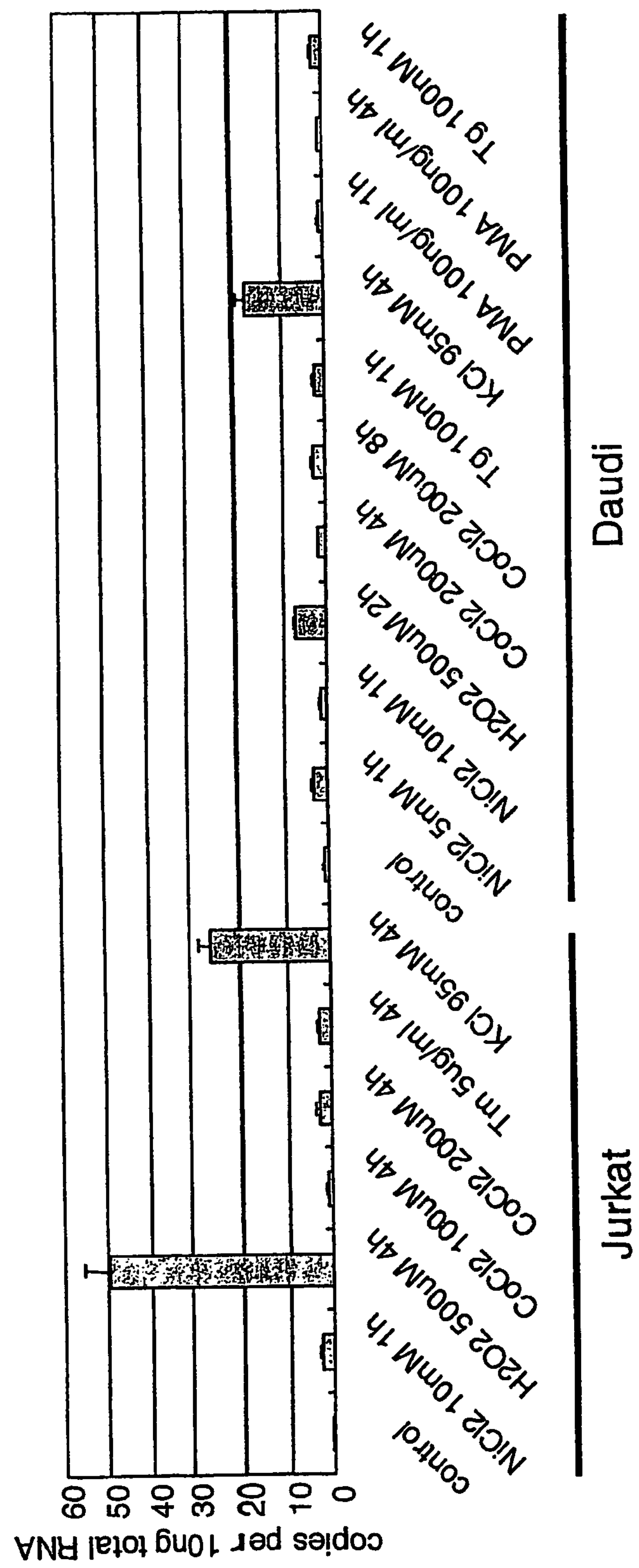
FIG. 7 shows changes in the expression level of human RC Kinase in the Jurkat and Daudi cell lines in response to treatment with various stimuli that cause cell growth or cellular stress. Both Jurkat and Daudi cells show upregulation of RC Kinase expression after stimulation with 95 mM KCl, and Jurkat cells show upregulation of RC Kinase expression after stimulation with 500 μM $H_2O_2$.

Because the occurrence of COPD is strongly correlated with the long-term repeated inhalation of irritants contained in tobacco smoke, the applicants performed an analysis to determine the influence of various cellular stress inducing compounds on the expression of RC Kinase. As shown in FIGS. 6 and 7, the expression of RC Kinase in the cell lines HEK293, Jurkat, and Daudi increased significantly after treatment of the cells with 95 mM potassium chloride (KCl), which subjects the cells to a hyperosmotic stress. Additionally, the Jurkat cell line (and to a smaller degree, the Daudi cell line) increased its expression of RC Kinase in response to 500 μm hydrogen peroxide ($H_2O_2$), a treatment which subjects the cells to an oxidative stress and which has been reported to impair the capacity of B cells to stimulate specific T cells. Such upregulation of RC Kinase in the cell lines in response to hyperosmotic and oxidative stress suggests that higher expression of RC Kinase in the lungs of COPD patients may be the result of cellular stresses caused by the irritants in tobacco smoke or stresses caused by the inflammatory response to those irritants.

Example 10

Figure 9:
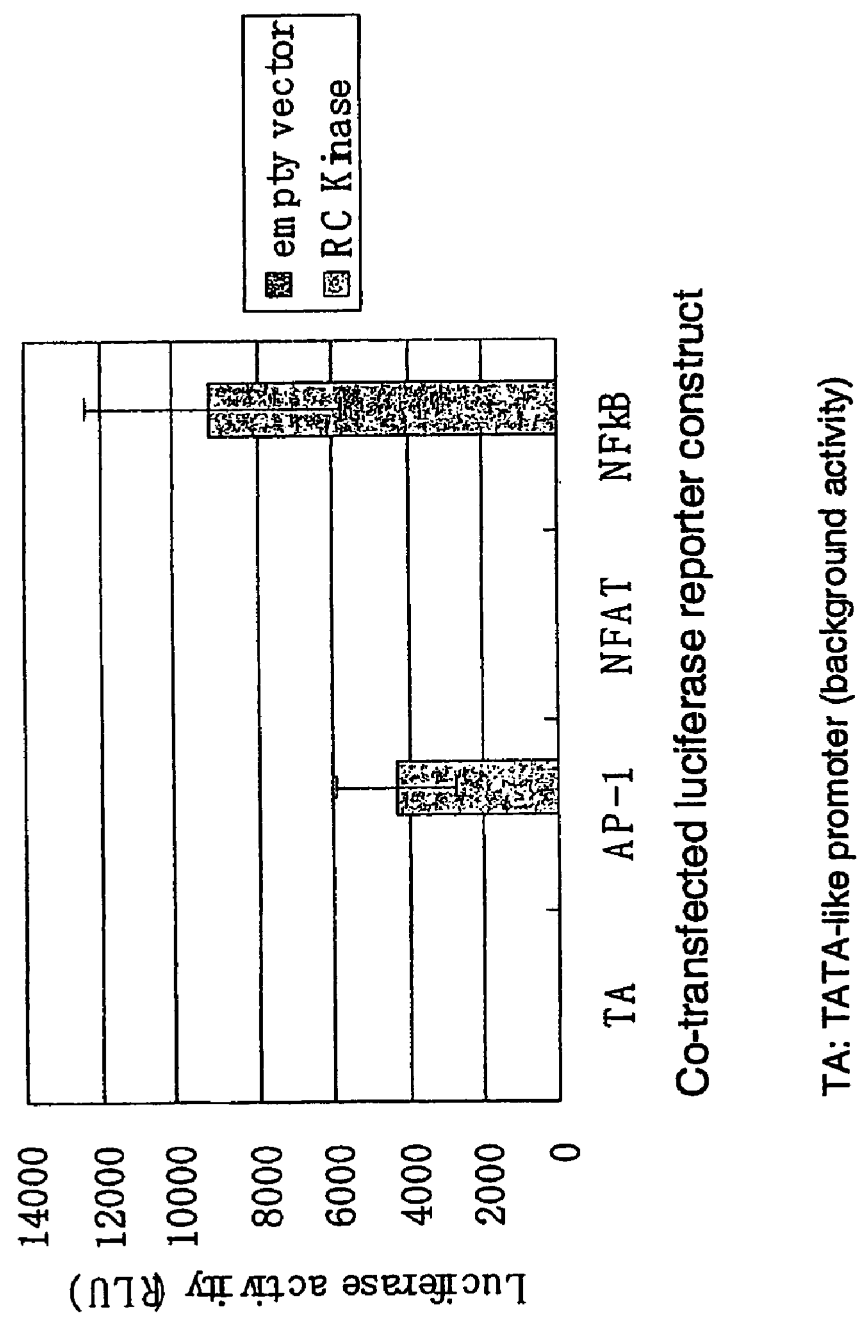
FIG. 9 shows the ability of human RC Kinase to induce the activation of the transcription factors AP-1 and NFκB. An RC Kinase expression vector or an empty vector was transfected into HEK293 cells together with luciferase reporter gene constructs for the transcription factors AP-1, NFAT, NFκB, and the TATA-like promoter. Luciferase activity (expressed in relative light units (RLU) compared with the TATA-like promoter's background luciferase production) was measured 48 hours after transfection.
Figure 10:
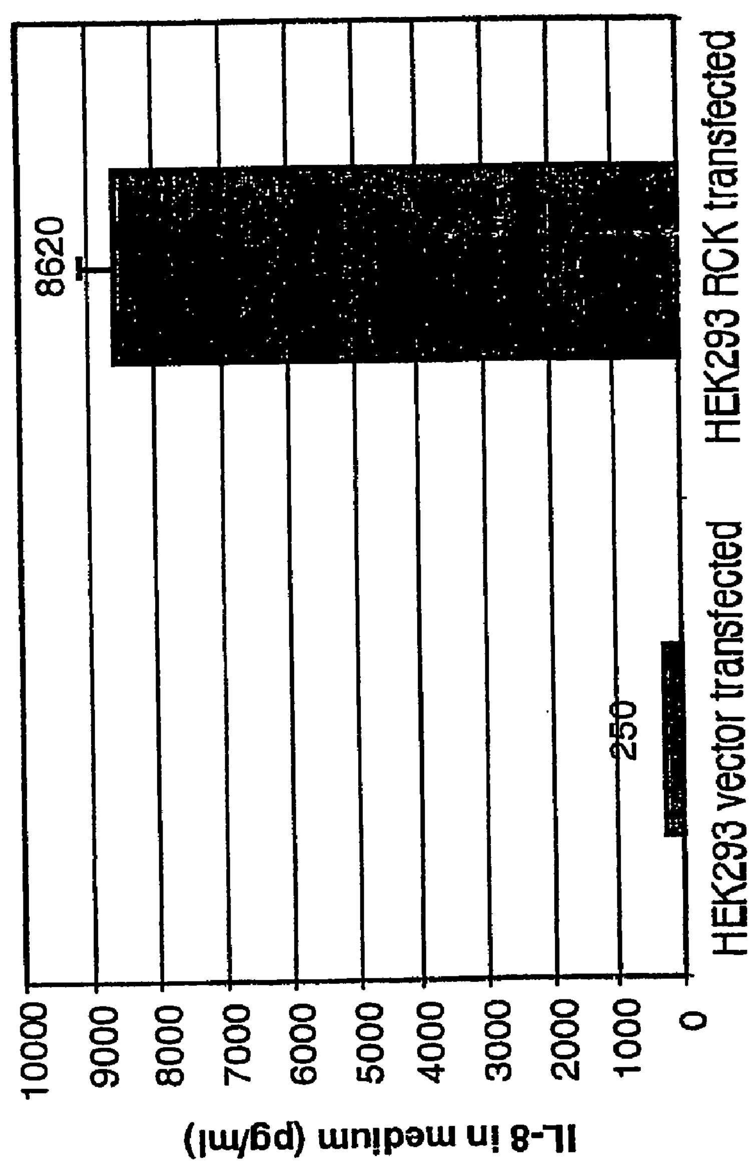
FIG. 10 shows the enhanced production of Interleukin-8 in HEK293 cells transfected with an RC Kinase expression construct. IL-8 protein levels in the culture medium were measured by an enzyme-linked immunosorbent assay 48 hours after the transfection of either an empty vector or an RC Kinase expression construct.
Figure 11:
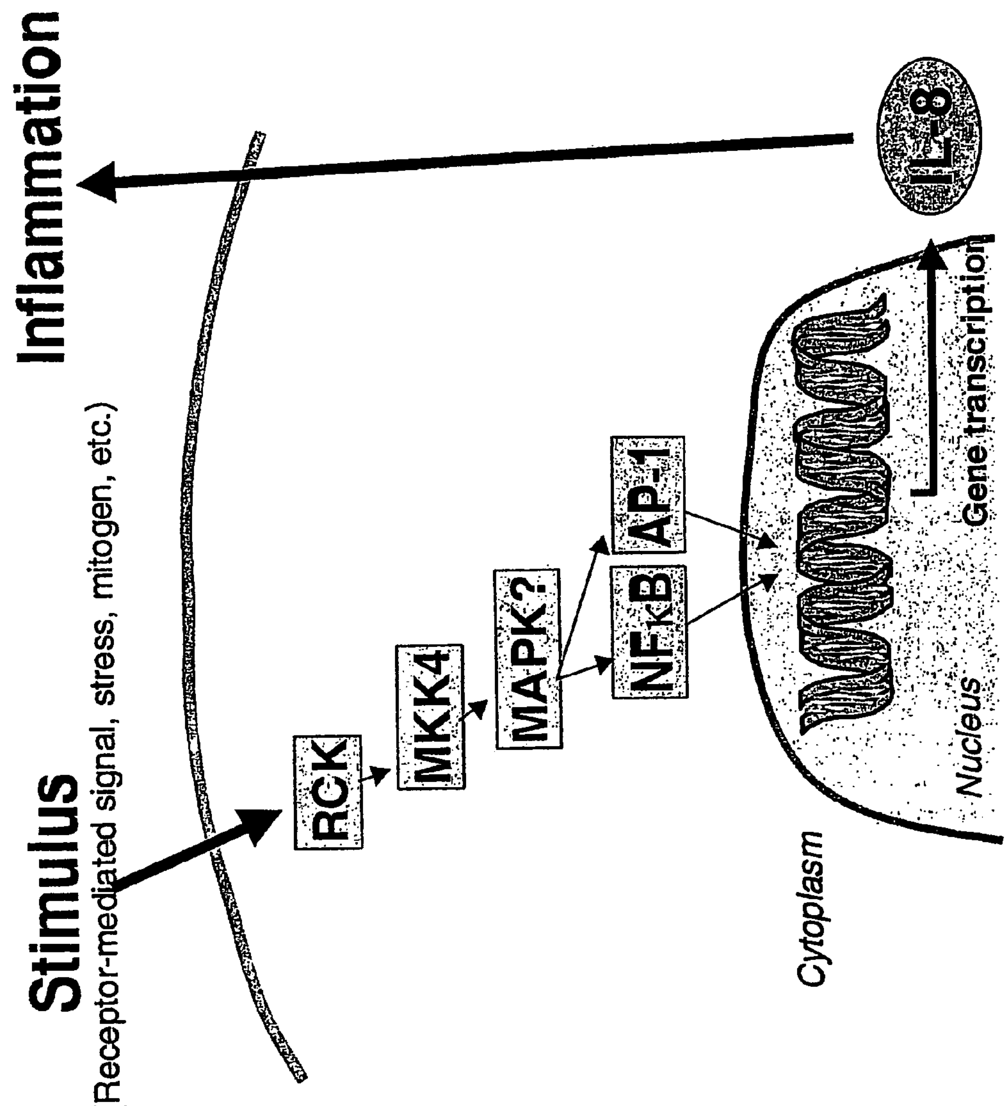
FIG. 11 shows an illustration indicating the role of RC Kinase in a MAP kinase phosphorelay system. RC Kinase is activated in response to receptor-mediated signaling, stress, mitogens, or other stimuli, or its expression is upregulated in response to such stimuli. As a result, MKK4 and possibly other substrates are phosphorylated, leading eventually to the activation of the transcription factors NFκB and AP-1. The transcription factors then contribute to the upregulation of expression of IL-8 and other inflammatory mediators, contributing to inflammation and other COPD-related pathology.

In order to determine whether the overexpression of RC Kinase has the potential to activate transcription factors, the applicants used a luciferase reporter gene assay to measure specific transcription factor activation. As shown in FIG. 9, the transfection and overexpression of RC Kinase lead to the activation of the transcription factors AP-1 and NFκB. Very little activation of the transcription factor NFAT could be detected. The consequences of this transcription factor activation were then studied by the applicants using microarrays to analyze which genes show increased transcription when RC Kinase is overexpressed. As a result, it was found that the expression of the chemokine Interleukin-8 was strongly increased in RC Kinase transfected cells. To confirm this result, the amounts of Interleukin-8 in the culture medium from cells transfected with an RC Kinase expression vector and from cells transfected with an empty vector were compared by enzyme-linked immunosorbent assay. As shown in FIG. 10, overexpression of RC Kinase causes a nearly 35-fold increase in the production of Interleukin-8 by the cells. Therefore, as illustrated in FIG. 11, RC Kinase appears to be upregulated and possibly activated by cellular stress, then phosphorylates MKK4 (and to a lesser extent MKK6), which leads to the activation of transcription factors AP-1 and NFκB. As a result of activation of this signaling cascade, Interleukin-8 production is increased and leads to the recruitment of inflammatory cells, such as neutrophils, that play a role in the pathology of COPD.

Example 11

Measurement of Interleukin-8 Production by Cells Expressing RC Kinase

Levels of h-IL-8 in the culture media of HEK293 cells expressing RC Kinase were measured using MAXISORP 96-well flat-bottom plates (Nunc, Roskilde, Denmark) using the Duoset ELISA Development System for human IL-8 (Genzyme Diagnostics, Cambridge, Mass.).

Culture medium was collected from HEK293 cells two days after transfection with an empty vector or an RC Kinase expression vector. 100 μl of the collected medium was diluted and put into wells of plates that had been precoated overnight with primary antibody and blocked with 300 μl of 1% BSA-PBS for 1 h at room temperature. The plates were then incubates for 2 h at room temperature. After washing the plates twice with 300 μl of PBS-0.05% Tween, 100 μl of 0.25 μg/ml secondary antibody diluted with PBS-0.1% BSA-0.05% Tween was added to the wells and the plates were incubated for an additional 1 h at room temperature. The plates were then washed three times with 300 μl of PBS-0.05% Tween. 100 μl of 0.25 μg/ml detection antibody (streptavidin-HRP) diluted with PBS-0.1% BSA-0.05% Tween was added, and the plates incubated for 1 h at room temperature. After washing the plates four times with 300 μl of PBS-0.05% Tween, the plates were developed using a peroxidase mediated color (Sumitomo Bakelite, Tokyo, Japan) and the absorbance was measured at OD 450 nm. The concentration of Interleukin-8 was then calculated by comparing the measured absorbance against the absorbance of serially diluted IL-8 standards prepared simultaneously.

As a result, it was shown that overexpression of RC Kinase in HEK293 cells causes an approximate 35 fold increase in the production of Interleukin 8 (FIG. 10).

The invention claimed is:

1. An isolated polynucleotide encoding a RC Kinase polypeptide and being selected from the group consisting of:

a) a polynucleotide encoding a RC Kinase polypeptide comprising an amino acid sequence selected from the group consisting of: amino acid sequences which are at least 90% identical to the amino acid sequence shown in SEQ ID NO: 10; and the amino acid sequence shown in SEQ ID NO: 10;

b) a polynucleotide comprising the sequence of SEQ ID NO: 4; and c) a polynucleotide the sequence of which deviates from the polynucleotide sequences specified in (a) or (b) due to the degeneration of the genetic code.

2. An expression vector containing the polynucleotide of claim 1.

3. An host cell containing the expression vector of claim 2.

4. A method for producing a RC Kinase polypeptide, wherein the method comprises the following steps: a) culturing the host cell of claim 3 under conditions suitable for the expression of the RC Kinase polypeptide; and b) recovering the RC Kinase polypeptide from the host cell culture.

5. An isolated polynucleotide encoding a RC Kinase polypeptide and being selected from the group consisting of:

a) a polynucleotide encoding a RC Kinase polypeptide comprising an amino acid sequence selected from the group consisting of: amino acid sequences which are at least 96% identical to the amino acid sequence shown in SEQ ID NO: 10; and the amino acid sequence shown in SEQ ID NO: 10;

b) a polynucleotide comprising the sequence of SEQ ID NO: 4; and c) a polynucleotide the sequence of which deviates from the polynucleotide sequences specified in (a) or (b) due to the degeneration of the genetic code.

6. An expression vector containing the polynucleotide of claim 5.

7. An host cell containing the expression vector of claim 6.

8. A method for producing a RC Kinase polypeptide, wherein the method comprises the following steps: a) culturing the host cell of claim 7 under conditions suitable for the expression of the RC Kinase polypeptide; and b) recovering the RC Kinase polypeptide from the host cell culture.

9. An isolated polynucleotide encoding a RC Kinase polypeptide and being selected from the group consisting of:

a) a polynucleotide encoding a RC Kinase polypeptide consisting of the amino acid sequence shown in SEQ ID NO: 10;

b) a polynucleotide consisting of the sequence shown in SEQ ID NO: 4; and c) a polynucleotide the sequence of which deviates from the polynucleotide sequences specified in (a) or (b) due to the degeneration of the genetic code.

10. An expression vector containing the polynucleotide of claim 9.

11. An host cell containing the expression vector of claim 10.

12. A method for producing a RC Kinase polypeptide, wherein the method comprises the following steps: a) culturing the host cell of claim 11 under conditions suitable for the expression of the RC Kinase polypeptide; and b) recovering the RC Kinase polypeptide from the host cell culture.

* * * * *

SEQUENCE LISTING

```
<160> NUMBER OF SEQ ID NOS: 16

<210> SEQ ID NO 1
<211> LENGTH: 3719
<212> TYPE: DNA
<213> ORGANISM: Homo sapiens

<400> SEQUENCE: 1

ttcaaagaaa cagcagcttt tggacatttt aatgagttct atgccaaaac cagaaagaca      60

tgctgagtca ttgcttgaca tttgtcatga tacaaactct tctccaactg atttgatgac     120

agttaccaaa aatcaaaaca tcatcttgca aagcatcagc agaagtgagg agttcgacca     180

agatggtgac tgcagtcatt ccacactggt taatgaagaa gaagatccca gtggtggtag     240

acaggactgg caacccagga cagaagagtt ttcgacctct catatgaagt acagtggccg     300

aagcatcaag ttccttctgc caccactgtc actcttgccc acgcgatctg gtgtccttac     360

tatcccccaa aatcacaagt ttccaaaaga aaaagaaaga aacattccaa gtctcacatc     420
```

-continued

```
ttttgtgcct aagctctcag tgtctgttcg tcaatctgat gagctcagcc catcaaacga    480
gcctccggga gccctagtta agtcgttgat ggatccgact ctcaggtctt ctgatggctt    540
catttggtca agaaacatgt gctcttttcc taagactaac catcacaggc aatgcctgga    600
gaaggaggaa aactggaaat ccaaggaaat agaagaatgt aacaaaattg aaatcactca    660
ctttgaaaaa gggcagtctt tggtgtcttt tgagaatttg aaggaaggca atattcctgc    720
agttagggaa gaggatattg actgccatgg tagtaaaacg cgaaaacctg aagaagagaa    780
ctctcaatat ctttcatcaa gaaagaatga gagttcagta gccaaaaact atgaacaaga    840
tccagaaata gtatgtacca ttccaagcaa gttccaagaa acccagcatt cagaaataac    900
tccaagccag gatgaagaga tgagaaataa taaagctgct tcaaaaagag tttcattaca    960
taaaaatgaa gcaatggaac caaacaatat tttagaagag tgtactgtac ttaaaagctt   1020
atccagtgta gtctttgatg accccattga taaactccca gaaggttgta gcagcatgga   1080
gacaaacata aaaatatcaa tagcagaaag agccaaacca gaaatgagta ggatggtgcc   1140
tcttatccac atcaccttcc ctgtggatgg aagccccaag gaaccagtga tagccaaacc   1200
aagcctccaa acaagaaagg gaaccattca taacaaccat agtgtcaaca tacctgtaca   1260
ccaagaaaat gacaagcata agatgaattc ccataggagt aagttggatt caaagaccaa   1320
gacaagtaag aagacacctc agaattttgt gatttctact gaaggtccca ttaagcctac   1380
catgcataaa accagcataa aaacacaaat tttcccggct ttgggacttg tggaccccag   1440
gccttggcaa ttgcccaggt ttcaaaagaa aatgccacag atagcaaaga agcaatcaac   1500
tcaccggact cagaaaccta aaaagcaatc atttccttgc atctgtaaaa atccaggaac   1560
acagaagtca tgtgttcctc tctctgttca accgacagag ccaagactaa attacctaga   1620
tcttaagtat agtgatatgt tcaaagaaat caattcaact gctaatggac ctggaatcta   1680
tgaaatgttt gggacccctg tttattgtca tgtgcgagag actgaaaggg atgaaaacac   1740
gtattaccgt gagatatgtt cggctccatc aggcagacgt atcaccaata aatgtcgatc   1800
ttcacacagt gagaggaaga gcaatatcag aacaagactt tctcagaaaa aaacacatat   1860
gaaatgccca aagacttcat ttggcattaa acaagagcac aaagtcttaa tttctaaaga   1920
aaagagttcc aaggctgtac atagcaacct acatgacatt gaaaatggtg atggtatttc   1980
agaaccagac tggcagataa agtcttcagg aaatgagttt ctatcttcca aagatgaaat   2040
tcatcccatg aacttggctc agacacctga gcagtccatg aaacagaatg aattccctcc   2100
tgtctcagat ttatccattg ttgaagaagt ttctatggaa gagtctactg gtgatagaga   2160
catttctaac aatcaaatac tcaccacaag cctcagagat ctgcaagaac ttgaagagct   2220
acatcaccag atcccattta tcccttcaga agacagctgg gcagtgccca gtgagaagaa   2280
ttctaacaag tatgtacagc aagaaaagca gaatacagca tctcttagta aagtaaatgc   2340
cagccgaatt ttaactaatg atctagagtt tgatagtgtt tcagatcact ctaaaacact   2400
tacaaatttc tctttccaag caaaacaaga aagtgcatct tcccagacat atcaatattg   2460
ggtacattat ttggatcatg atagtttagc aaataagtca atcacatatc aaatgtttgg   2520
aaaaacctta agtggcacaa attcaatttc ccaagaaatt atggactctg taaataatga   2580
agaattgaca gatgaactat taggttgtct agctgcagaa ttattagctc ttgatgagaa   2640
agataacaac tcttgccaaa aaatggcaaa tgaaacagat cctgaaaacc taaatcttgt   2700
cctcagatgg agaggaagta ccccaaaaga aatgggcaga gagacaacaa aagtcaaaat   2760
acagaggcat agtagtgggc tcaggatata tgacagggag gagaaatttc tcatctcaaa   2820
```

```
tgaaaagaag atattttctg aaaatagttt aaagtctgaa gaacctatcc tatggaccaa   2880

gggtgagatt cttggaaagg gagcctacgg cacagtatac tgtggtctca ctagtcaagg   2940

acagctaata gctgtaaaac aggtggcttt ggatacctct aataaattag ctgctgaaaa   3000

ggaataccgg aaactacagg aagaagtaga tttgctcaaa gcactgaaac atgtcaacat   3060

tgtggcctat ttggggacat gcttgcaaga gaacactgtg agcattttca tggagtttgt   3120

tcctggtggc tcaatctcta gtattataaa ccgttttggg ccattgcctg agatggtgtt   3180

ctgtaaatat acgaaacaaa tacttcaagg tgttgcttat ctccatgaga actgtgtggt   3240

acatcgcgat atcaaaggaa ataatgttat gctcatgcca actggaataa taaagctgat   3300

tgactttggc tgtgccaggc gtttggcctg ggcaggttta aatggcaccc acagtgacat   3360

gcttaagtcc atgcatggga ctccatattg gatggcccca gaagtcatca atgagtctgg   3420

ctatggacgg aaatcagata tctggagcat tggttgtact gtgtttgaga tggctacagg   3480

gaagcctcca ctggcttcca tggacaggat ggccgccatg ttttacatcg gagcacaccg   3540

agggctgatg cctcctttac cagaccactt ctcagaaaat gcagcagact ttgtgcgcat   3600

gtgcctgacc agggaccagc atgagcgacc ttctgctctc cagctcctga agcactcctt   3660

cttggagaga agtcactgaa tatacatcaa gactttcttc ccagttccac tgcagatgc    3719
```

```
<210> SEQ ID NO 2
<211> LENGTH: 3338
<212> TYPE: DNA
<213> ORGANISM: Homo sapiens

<400> SEQUENCE: 2
```

```
ttcgaccaag atggtgactg cagtcattcc acactggtta atgaagaaga agatcccagt     60

ggtggtagac aggactggca acccaggaca gaaggtgttg agatcactgt aacttttcca    120

agagatgtca gtcctcccca agaaatgagc caagaagact taaaagaaaa gaatctgata    180

aactcatcgc ttcaagaatg ggcacaagca catgcagttt ctcatccaaa tgaaatagaa    240

acggtggagc tcaggaaaaa gaagctgacc atgcggccct tagttttgca aaaagaggaa    300

agttccaggg agctctgcaa tgtgaacttg ggctttttgc taccaagatc ttgtttagaa    360

ctgaacattt ccaagtctgt aaccagagaa gatgctcctc attttctgaa ggagcagcaa    420

agaaaatctg aagagttttc gacctctcat atgaagtaca gtggccgaag catcaagttc    480

cttctgccac cactgtcact cttgcccacg cgatctggtg tccttactat cccccaaaat    540

cacaagtttc caaaagaaaa agaaagaaac attccaagtc tcacatcttt tgtgcctaag    600

ctctcagtgt ctgttcgtca atctgatgag ctcagcccat caaacgagcc tccgggagcc    660

ctagttaagt cgttgatgga tccgactctc aggtcttctg atggcttcat ttggtcaaga    720

aacatgtgct cttttcctaa gactaaccat cacaggcaat gcctggagaa ggaggaaaac    780

tggaaatcca aggaaataga agaatgtaac aaaattgaaa tcactcactt tgaaaaaggg    840

cagtctttgg tgtcttttga gaatttgaag gaaggcaata ttcctgcagt tagggaagag    900

gatattgact gccatggtag taaaacgcga aaacctgaag aagagaactc tcaatatctt    960

tcatcaagaa agaatgagag ttcagtagcc aaaaactatg aacaagatcc agaaatagta   1020

tgtaccattc caagcaagtt ccaagaaacc cagcattcag aaataactcc aagccaggat   1080

gaagagatga gaaataataa agctgcttca aaaagagttt cattacataa aaatgaagca   1140

atggaaccaa acaatatttt agaagagtgt actgtactta aaagcttatc cagtgtagtc   1200
```

-continued

```
tttgatgacc ccattgataa actcccagaa ggttgtagca gcatggagac aaacataaaa   1260

atatcaatag cagaaagagc caaaccagaa atgagtagga tggtgcctct tatccacatc   1320

accttccctg tggatggaag ccccaaggaa ccagtgatag ccaaaccaag cctccaaaca   1380

agaaagggaa ccattcataa caaccatagt gtcaacatac ctgtacacca agaaaatgac   1440

aagcataaga tgaattccca taggagtaag ttggattcaa agaccaagac aagtaagaag   1500

acacctcaga attttgtgat ttctactgaa ggtcccatta agcctaccat gcataaaacc   1560

agcataaaaa cacaaatttt cccggctttg ggacttgtgg accccaggcc ttggcaattg   1620

cccaggtttc aaaagaaaat gccacagata gcaaagaagc aatcaactca ccggactcag   1680

aaacctaaaa agcaatcatt tccttgcatc tgtaaaaatc caggaacaca gaagtcatgt   1740

gttcctctct ctgttcaacc gacagagcca agactaaatt acctagatct taagtatagt   1800

gatatgttca aagaaatcaa ttcaactgct aatggacctg gaatctatga aatgtttggg   1860

acccctgttt attgtcatgt gcgagagact gaaagggatg aaaacacgta ttaccgtgag   1920

atatgttcgg ctccatcagg cagacgtatc accaataaat gtcgatcttc acacagtgag   1980

aggaagagca atatcagaac aagactttct cagaaaaaaa cacatatgaa atgcccaaag   2040

acttcatttg gcattaaaca agagcacaaa gtcttaattt ctaaagaaaa gagttccaag   2100

gctgtacata gcaacctaca tgacattgaa aatggtgatg gtatttcaga accagactgg   2160

cagataaagt cttcaggaaa tgagtttcta tcttccaaag atgaaattca tcccatgaac   2220

ttggctcaga cacctgagca gtccatgaaa cagaatgaat tccctcctgt ctcagattta   2280

tccattgttg aagaagtttc tatggaagag tctactggtg atagagacat ttctaacaat   2340

caaatactca ccacaagcct cagagatctg caagaacttg aagagctaca tcaccagatc   2400

ccatttatcc cttcagaaga cagctgggca gtgcccagtg agaagaattc taacaagtat   2460

gtacagcaag aaaagcagaa tacagcatct cttagtaaag taaatgccag ccgaatttta   2520

actaatgatc tagagtttga tagtgtttca gatcactcta aaacacttac aaatttctct   2580

ttccaagcaa aacaagaaag tgcatcttcc cagacatatc aatattgggt acattatttg   2640

gatcatgata gtttagcaaa taagtcaatc acatatcaaa tgtttggaaa aaccttaagt   2700

ggcacaaatt caatttccca agaaattatg gactctgtaa ataatgaaga attgacagat   2760

gaactattag gttgtctagc tgcagaatta ttagctcttg atgagaaaga taacaactct   2820

tgccaaaaaa tggcaaatga aacagatcct gaaaacctaa atcttgtcct cagatggaga   2880

ggaagtaccc caaaagaaat gggcagagag acaacaaaag tcaaaataca gaggcatagt   2940

agtgggctca ggatatatga cagggaggag aaatttctca tctcaaatga aaagaagata   3000

ttttctgaaa atagtttaaa gtctgaagaa cctatcctat ggaccaaggg tgagattctt   3060

ggaaagggag cctacggcac agtatactgt ggtctcacta gtcaaggaca gctaatagct   3120

gtaaaacagg tggctttgga tacctctaat aaattagctg ctgaaaagga ataccggaaa   3180

ctacaggaag aagtagattt gctcaaagca ctgaaacatg tgcctgacca gggaccagca   3240

tgagcgacct tctgctctcc agctcctgaa gcactccttc ttggagagaa gtcactgaat   3300

atacatcaag actttcttcc cagttccact gcagatgc                           3338
```

<210> SEQ ID NO 3
<211> LENGTH: 3510
<212> TYPE: DNA
<213> ORGANISM: Homo sapiens

<400> SEQUENCE: 3

-continued

```
ttcaaagaaa cagcagcttt tggacatttt aatgagttct atgccaaaac cagaaagaca     60
tgctgagtca ttgcttgaca tttgtcatga tacaaactct tctccaactg atttgatgac    120
agttaccaaa aatcaaaaca tcatcttgca aagcatcagc agaagtgagg agttcgacca    180
agatggtgac tgcagtcatt ccacactggt taatgaagaa gaagatccca gtggtggtag    240
acaggactgg caacccagga cagaaggtgt tgagatcact gtaacttttc caagagatgt    300
cagtcctccc caagaaatga gccaagaaga cttaaaagaa aagaatctga taaactcatc    360
gcttcaagaa tgggcacaag cacatgcagt ttctcatcca aatgaaatag aaacggtgga    420
gctcaggaaa aagaagctga ccatgcggcc cttagttttg caaaaagagg aaagttccag    480
ggagctctgc aatgtgaact tgggcttttt gctaccaaga tcttgtttag aactgaacat    540
ttccaagtct gtaaccagag aagatgctcc tcattttctg aaggagcagc aaagaaaatc    600
tgaagagttt tcgacctctc atatgaagta cagtggccga agcatcaagt tccttctgcc    660
accactgtca ctcttgccca cgcgatctgg tgtccttact atcccccaaa atcacaagtt    720
tccaaaagaa aaagaaagaa acattccaag tctcacatct tttgtgccta agctctcagt    780
gtctgttcgt caatctgatg agctcagccc atcaaacgag cctccgggag ccctagttaa    840
gtcgttgatg gatccgactc tcaggtcttc tgatggcttc atttggtcaa gaaacatgtg    900
ctcttttcct aagactaacc atcacaggca atgcctggag aaggaggaaa actggaaatc    960
caaggaaata gaagaatgta acaaaattga aatcactcac tttgaaaaag ggcagtcttt   1020
ggtgtctttt gagaatttga aggaaggcaa tattcctgca gttagggaag aggatattga   1080
ctgccatggt agtaaaacgc gaaaacctga agaagagaac tctcaatatc tttcatcaag   1140
aaagaatgag agttcagtag ccaaaaacta tgaacaagat ccagaaatag tatgtaccat   1200
tccaagcaag ttccaagaaa cccagcattc agaaataact ccaagccagg atgaagagat   1260
gagaaataat aaagctgctt caaaaagagt ttcattacat aaaaatgaag caatggaacc   1320
aaacaatatt ttagaagagt gtactgtact taaaagctta tccagtgtag tctttgatga   1380
ccccattgat aaactcccag aaggttgtag cagcatggag acaaacataa aaatatcaat   1440
agcagaaaga gccaaaccag aaatgagtag gatggtgcct cttatccaca tcaccttccc   1500
tgtggatgga agccccaagg aaccagtgat agccaaacca agcctccaaa caagaaaggg   1560
aaccattcat aacaaccata gtgtcaacat acctgtacac caagaaaatg acaagcataa   1620
gatgaattcc cataggagta agttggattc aaagaccaag acaagtaaga agacacctca   1680
gaattttgtg atttctactg aaggtcccat taagcctacc atgcataaaa ccagcataaa   1740
aacacaaatt ttcccggctt tgggacttgt ggaccccagg ccttggcaat tgcccaggtt   1800
tcaaaagaaa atgccacaga tagcaaagaa gcaatcaact caccggactc agaaacctaa   1860
aaagcaatca tttccttgca tctgtaaaaa tccaggaaca cagaagtcat gtgttcctct   1920
ctctgttcaa ccgacagagc caagactaaa ttacctagat cttaagtata gtgatatgtt   1980
caaagaaatc aattcaactg ctaatggacc tggaatctat gaaatgtttg ggacccctgt   2040
ttattgtcat gtgcgagaga ctgaaaggga tgaaaacacg tattaccgtg agatatgttc   2100
ggctccatca ggcagacgta tcaccaataa atgtcgatct tcacacagtg agaggaagag   2160
caatatcaga acaagacttt ctcagaaaaa aacacatatg aaatgcccaa agacttcatt   2220
tggcattaaa caagagcaca aagtcttaat ttctaaagaa aagagttcca aggctgtaca   2280
tagcaaccta catgacattg aaaatggtga tggtatttca gaaccagact ggcagataaa   2340
```

-continued

```
gtcttcagga aatgagtttc tatcttccaa agatgaaatt catcccatga acttggctca   2400

gacacctgag cagtccatga aacagaatga attccctcct gtctcagatt tatccattgt   2460

tgaagaagtt tctatggaag agtctactgg tgatagagac atttctaaca atcaaatact   2520

caccacaagc ctcagagatc tgcaagaact tgaagagcta catcaccaga tcccatttat   2580

cccttcagaa gacagctggg cagtgcccag tgagaagaat tctaacaagt atgtacagca   2640

agaaaagcag aatacagcat ctcttagtaa agtaaatgcc agccgaattt taactaatga   2700

tctagagttt gatagtgttt cagatcactc taaaacactt acaaatttct ctttccaagc   2760

aaaacaagaa agtgcatctt cccagacata tcaatattgg gtacattatt tggatcatga   2820

tagtttagca aataagtcaa tcacatatca aatgtttgga aaaaccttaa gtggcacaaa   2880

ttcaatttcc caagaaatta tggactctgt aaataatgaa gaattgacag atgaactatt   2940

aggttgtcta gctgcagaat tattagctct tgatgagaaa gataacaact cttgccaaaa   3000

aatggcaaat gaaacagatc ctgaaaacct aaatcttgtc ctcagatgga gaggaagtac   3060

cccaaaagaa atgggcagag agacaacaaa agtcaaaata cagaggcata gtagtgggct   3120

caggatatat gacagggagg agaaatttct catctcaaat gaaaagaaga tattttctga   3180

aaatagttta aagtctgaag aacctatcct atggaccaag ggtgagattc ttggaaaggg   3240

agcctacggc acagtatact gtggtctcac tagtcaagga cagctaatag ctgtaaaaca   3300

ggtggctttg gatacctcta ataaattagc tgctgaaaag gaataccgga aactacagga   3360

agaagtagat ttgctcaaag cactgaaaca tgtgcctgac cagggaccag catgagcgac   3420

cttctgctct ccagctcctg aagcactcct tcttggagag aagtcactga atatacatca   3480

agactttctt cccagttcca ctgcagatgc                                    3510
```

<210> SEQ ID NO 4
<211> LENGTH: 4058
<212> TYPE: DNA
<213> ORGANISM: Homo sapiens

<400> SEQUENCE: 4

```
ttcaaagaaa cagcagcttt tggacatttt aatgagttct atgccaaaac cagaaagaca     60

tgctgagtca ttgcttgaca tttgtcatga tacaaactct tctccaactg atttgatgac    120

agttaccaaa aatcaaaaca tcatcttgca aagcatcagc agaagtgagg agttcgacca    180

agatggtgac tgcagtcatt ccacactggt taatgaagaa gaagatccca gtggtggtag    240

acaggactgg caacccagga cagaaggtgt tgagatcact gtaacttttc caagagatgt    300

cagtcctccc caagaaatga gccaagaaga cttaaaagaa aagaatctga taaactcatc    360

gcttcaagaa tgggcacaag cacatgcagt ttctcatcca aatgaaatag aaacggtgga    420

gctcaggaaa aagaagctga ccatgcggcc cttagttttg caaaaagagg aaagttccag    480

ggagctctgc aatgtgaact tgggcttttt gctaccaaga tcttgtttag aactgaacat    540

ttccaagtct gtaaccagag aagatgctcc tcattttctg aaggagcagc aaagaaaatc    600

tgaagagttt tcgacctctc atatgaagta cagtggccga agcatcaagt tccttctgcc    660

accactgtca ctcttgccca cgcgatctgg tgtccttact atcccccaaa atcacaagtt    720

tccaaaagaa aaagaaagaa acattccaag tctcacatct tttgtgccta agctctcagt    780

gtctgttcgt caatctgatg agctcagccc atcaaacgag cctccgggag ccctagttaa    840

gtcgttgatg gatccgactc tcaggtcttc tgatggcttc atttggtcaa gaaacatgtg    900

ctcttttcct aagactaacc atcacaggca atgcctggag aaggaggaaa actggaaatc    960
```

-continued

```
caaggaaata gaagaatgta acaaaattga aatcactcac tttgaaaaag ggcagtcttt   1020
ggtgtctttt gagaatttga aggaaggcaa tattcctgca gttagggaag aggatattga   1080
ctgccatggt agtaaaacgc gaaaacctga agaagagaac tctcaatatc tttcatcaag   1140
aaagaatgag agttcagtag ccaaaaacta tgaacaagat ccagaaatag tatgtaccat   1200
tccaagcaag ttccaagaaa cccagcattc agaaataact ccaagccagg atgaagagat   1260
gagaaataat aaagctgctt caaaaagagt ttcattacat aaaaatgaag caatggaacc   1320
aaacaatatt ttagaagagt gtactgtact taaaagctta tccagtgtag tctttgatga   1380
ccccattgat aaactcccag aaggttgtag cagcatggag acaaacataa aaatatcaat   1440
agcagaaaga gccaaaccag aaatgagtag gatggtgcct cttatccaca tcaccttccc   1500
tgtggatgga agccccaagg aaccagtgat agccaaacca agcctccaaa caagaaaggg   1560
aaccattcat aacaaccata gtgtcaacat acctgtacac caagaaaatg acaagcataa   1620
gatgaattcc cataggagta agttggattc aaagaccaag acaagtaaga agacacctca   1680
gaattttgtg atttctactg aaggtcccat taagcctacc atgcataaaa ccagcataaa   1740
aacacaaatt ttcccggctt tgggacttgt ggaccccagg ccttggcaat tgcccaggtt   1800
tcaaaagaaa atgccacaga tagcaaagaa gcaatcaact caccggactc agaaacctaa   1860
aaagcaatca tttccttgca tctgtaaaaa tccaggaaca cagaagtcat gtgttcctct   1920
ctctgttcaa ccgacagagc caagactaaa ttacctagat cttaagtata gtgatatgtt   1980
caaagaaatc aattcaactg ctaatggacc tggaatctat gaaatgtttg ggacccctgt   2040
ttattgtcat gtgcgagaga ctgaaaggga tgaaaacacg tattaccgtg agatatgttc   2100
ggctccatca ggcagacgta tcaccaataa atgtcgatct tcacacagtg agaggaagag   2160
caatatcaga acaagacttt ctcagaaaaa aacacatatg aaatgcccaa agacttcatt   2220
tggcattaaa caagagcaca aagtcttaat ttctaaagaa aagagttcca aggctgtaca   2280
tagcaaccta catgacattg aaaatggtga tggtatttca gaaccagact ggcagataaa   2340
gtcttcagga aatgagtttc tatcttccaa agatgaaatt catcccatga acttggctca   2400
gacacctgag cagtccatga aacagaatga attccctcct gtctcagatt tatccattgt   2460
tgaagaagtt tctatggaag agtctactgg tgatagagac atttctaaca atcaaatact   2520
caccacaagc ctcagagatc tgcaagaact tgaagagcta catcaccaga tcccatttat   2580
cccttcagaa gacagctggg cagtgcccag tgagaagaat tctaacaagt atgtacagca   2640
agaaaagcag aatacagcat ctcttagtaa agtaaatgcc agccgaattt taactaatga   2700
tctagagttt gatagtgttt cagatcactc taaaacactt acaaatttct ctttccaagc   2760
aaaacaagaa agtgcatctt cccagacata tcaatattgg gtacattatt tggatcatga   2820
tagtttagca aataagtcaa tcacatatca aatgtttgga aaaaccttaa gtggcacaaa   2880
ttcaatttcc caagaaatta tggactctgt aaataatgaa gaattgacag atgaactatt   2940
aggttgtcta gctgcagaat tattagctct tgatgagaaa gataacaact cttgccaaaa   3000
aatggcaaat gaaacagatc ctgaaaacct aaatcttgtc ctcagatgga gaggaagtac   3060
cccaaaagaa atgggcagag agacaacaaa agtcaaaata cagaggcata gtagtgggct   3120
caggatatat gacagggagg agaaatttct catctcaaat gaaaagaaga tattttctga   3180
aaatagttta aagtctgaag aacctatcct atggaccaag ggtgagattc ttggaaaggg   3240
agcctacggc acagtatact gtggtctcac tagtcaagga cagctaatag ctgtaaaaca   3300
```

-continued

```
ggtggctttg gatacctcta ataaattagc tgctgaaaag gaataccgga aactacagga   3360

agaagtagat ttgctcaaag cactgaaaca tgtcaacatt gtggcctatt tggggacatg   3420

cttgcaagag aacactgtga gcattttcat ggagtttgtt cctggtggct caatctctag   3480

tattataaac cgttttgggc cattgcctga gatggtgttc tgtaaatata cgaaacaaat   3540

acttcaaggt gttgcttatc tccatgagaa ctgtgtggta catcgcgata tcaaaggaaa   3600

taatgttatg ctcatgccaa ctggaataat aaagctgatt gactttggct gtgccaggcg   3660

tttggcctgg gcaggtttaa atggcaccca cagtgacatg cttaagtcca tgcatgggac   3720

tccatattgg atggccccag aagtcatcaa tgagtctggc tatggacgga aatcagatat   3780

ctggagcatt ggttgtactg tgtttgagat ggctacaggg aagcctccac tggcttccat   3840

ggacaggatg gccgccatgt tttacatcgg agcacaccga gggctgatgc ctcctttacc   3900

agaccacttc tcagaaaatg cagcagactt tgtgcgcatg tgcctgacca gggaccagca   3960

tgagcgacct tctgctctcc agctcctgaa gcactccttc ttggagagaa gtcactgaat   4020

atacatcaag actttcttcc cagttccact gcagatgc                           4058
```

```
<210> SEQ ID NO 5
<211> LENGTH: 1460
<212> TYPE: DNA
<213> ORGANISM: Homo sapiens

<400> SEQUENCE: 5

ttcaaagaaa cagcagcttt tggacatttt aatgagttct atgccaaaac cagaaagaca     60

tgctgagtca ttgcttgaca tttgtcatga tacaaactct tctccaactg atttgatgac    120

agttaccaaa aatcaaaaca tcatcttgca aagcatcagc agaagtgagg agttcgacca    180

agatggtgac tgcagtcatt ccacactggt taatgaagaa gaagatccca gtggtggtag    240

acaggactgg caacccagga cagaaggtgt tgagatcact gtaacttttc caagagatgt    300

cagtcctccc caagaaatga gccaagaaga cttaaaagaa aagaatctga taaactcatc    360

gcttcaagaa tgggcacaag cacatgcagt ttctcatcca aatgaaatag aaacggtgga    420

gctcaggaaa aagaagctga ccatgcggcc cttagttttg caaaaagagg aaagttccag    480

ggagctctgc aatgtgaact tgggcttttt gctaccaaga tcttgtttag aactgaacat    540

ttccaagtct gtaaccagag aagatgctcc tcattttctg aaggagcagc aaagaaaatc    600

tgaagagttt tcgacctctc atatgaagta cagtggccga agcatcaaga ggcatagtag    660

tgggctcagg atatatgaca gggaggagaa atttctcatc tcaaatgaaa agaagatatt    720

ttctgaaaat agtttaaagt ctgaagaacc tatcctatgg accaaggtag atttgctcaa    780

agcactgaaa catgtcaaca ttgtggccta tttggggaca tgcttgcaag agaacactgt    840

gagcattttc atggagtttg ttcctggtgg ctcaatctct agtattataa accgttttgg    900

gccattgcct gagatggtgt tctgtaaata tacgaaacaa atacttcaag gtgttgctta    960

tctccatgag aactgtgtgg tacatcgcga tatcaaagga aataatgtta tgctcatgcc   1020

aactggaata ataaagctga ttgactttgg ctgtgccagg cgtttggcct gggcaggttt   1080

aaatggcacc cacagtgaca tgcttaagtc catgcatggg actccatatt ggatggcccc   1140

agaagtcatc aatgagtctg gctatggacg gaaatcagat atctggagca ttggttgtac   1200

tgtgtttgag atggctacag ggaagcctcc actggcttcc atggacagga tggccgccat   1260

gttttacatc ggagcacacc gagggctgat gcctccttta ccagaccact tctcagaaaa   1320

tgcagcagac tttgtgcgca tgtgcctgac cagggaccag catgagcgac cttctgctct   1380
```

-continued

```
ccagctcctg aagcactcct tcttggagag aagtcactga atatacatca agactttctt   1440

cccagttcca ctgcagatgc                                                1460


<210> SEQ ID NO 6
<211> LENGTH: 1604
<212> TYPE: DNA
<213> ORGANISM: Homo sapiens

<400> SEQUENCE: 6

ttcaaagaaa cagcagcttt tggacatttt aatgagttct atgccaaaac cagaaagaca     60

tgctgagtca ttgcttgaca tttgtcatga tacaaactct tctccaactg atttgatgac    120

agttaccaaa aatcaaaaca tcatcttgca aagcatcagc agaagtgagg agttcgacca    180

agatggtgac tgcagtcatt ccacactggt taatgaagaa gaagatccca gtggtggtag    240

acaggactgg caacccagga cagaaggtgt tgagatcact gtaacttttc caagagatgt    300

cagtcctccc caagaaatga gccaagaaga cttaaaagaa aagaatctga taaactcatc    360

gcttcaagaa tgggcacaag cacatgcagt ttctcatcca aatgaaatag aaacggtgga    420

gctcaggaaa aagaagctga ccatgcggcc cttagttttg caaaaaagag gaaagttccag    480

ggagctctgc aatgtgaact tgggcttttt gctaccaaga tcttgtttag aactgaacat    540

ttccaagtct gtaaccagag aagatgctcc tcattttctg aaggagcagc aaagaaaatc    600

tgaagagttt tcgacctctc atatgaagta cagtggccga agcatcaaga ggcatagtag    660

tgggctcagg atatatgaca gggaggagaa atttctcatc tcaaatgaaa agaagatatt    720

ttctgaaaat agtttaaagt ctgaagaacc tatcctatgg accaagggtg agattcttgg    780

aaagggagcc tacggcacag tatactgtgg tctcactagt caaggacagc taatagctgt    840

aaaacaggtg gctttggata cctctaataa attagctgct gaaaaggaat accggaaact    900

acaggaagaa gtagatttgc tcaaagcact gaaacatgtc aacattgtgg cctatttggg    960

gacatgcttg caagagaaca ctgtgagcat tttcatggag tttgttcctg gtggctcaat   1020

ctctagtatt ataaaccgtt ttgggccatt gcctgagatg gtgttctgta aatatacgaa   1080

acaaatactt caaggtgttg cttatctcca tgagaactgt gtggtacatc gcgatatcaa   1140

aggaaataat gttatgctca tgccaactgg aataataaag ctgattgact ttggctgtgc   1200

caggcgtttg gcctgggcag gtttaaatgg cacccacagt gacatgctta agtccatgca   1260

tgggactcca tattggatgg ccccagaagt catcaatgag tctggctatg gacggaaatc   1320

agatatctgg agcattggtt gtactgtgtt tgagatggct acagggaagc ctccactggc   1380

ttccatggac aggatggccg ccatgtttta catcggagca caccgagggc tgatgcctcc   1440

tttaccagac cacttctcag aaaatgcagc agactttgtg cgcatgtgcc tgaccaggga   1500

ccagcatgag cgaccttctg ctctccagct cctgaagcac tccttcttgg agagaagtca   1560

ctgaatatac atcaagactt tcttcccagt tccactgcag atgc                    1604


<210> SEQ ID NO 7
<211> LENGTH: 1225
<212> TYPE: PRT
<213> ORGANISM: Homo sapiens

<400> SEQUENCE: 7

Ser Lys Lys Gln Gln Leu Leu Asp Ile Leu Met Ser Ser Met Pro Lys
 1               5                  10                  15

Pro Glu Arg His Ala Glu Ser Leu Leu Asp Ile Cys His Asp Thr Asn
```

-continued

```
            20                  25                  30

Ser Ser Pro Thr Asp Leu Met Thr Val Thr Lys Asn Gln Asn Ile Ile
        35                  40                  45

Leu Gln Ser Ile Ser Arg Ser Glu Glu Phe Asp Gln Asp Gly Asp Cys
    50                  55                  60

Ser His Ser Thr Leu Val Asn Glu Glu Glu Asp Pro Ser Gly Gly Arg
65                  70                  75                  80

Gln Asp Trp Gln Pro Arg Thr Glu Glu Phe Ser Thr Ser His Met Lys
                85                  90                  95

Tyr Ser Gly Arg Ser Ile Lys Phe Leu Leu Pro Pro Leu Ser Leu Leu
            100                 105                 110

Pro Thr Arg Ser Gly Val Leu Thr Ile Pro Gln Asn His Lys Phe Pro
        115                 120                 125

Lys Glu Lys Glu Arg Asn Ile Pro Ser Leu Thr Ser Phe Val Pro Lys
    130                 135                 140

Leu Ser Val Ser Val Arg Gln Ser Asp Glu Leu Ser Pro Ser Asn Glu
145                 150                 155                 160

Pro Pro Gly Ala Leu Val Lys Ser Leu Met Asp Pro Thr Leu Arg Ser
                165                 170                 175

Ser Asp Gly Phe Ile Trp Ser Arg Asn Met Cys Ser Phe Pro Lys Thr
            180                 185                 190

Asn His His Arg Gln Cys Leu Glu Lys Glu Glu Asn Trp Lys Ser Lys
        195                 200                 205

Glu Ile Glu Glu Cys Asn Lys Ile Glu Ile Thr His Phe Glu Lys Gly
    210                 215                 220

Gln Ser Leu Val Ser Phe Glu Asn Leu Lys Glu Gly Asn Ile Pro Ala
225                 230                 235                 240

Val Arg Glu Glu Asp Ile Asp Cys His Gly Ser Lys Thr Arg Lys Pro
                245                 250                 255

Glu Glu Glu Asn Ser Gln Tyr Leu Ser Ser Arg Lys Asn Glu Ser Ser
            260                 265                 270

Val Ala Lys Asn Tyr Glu Gln Asp Pro Glu Ile Val Cys Thr Ile Pro
        275                 280                 285

Ser Lys Phe Gln Glu Thr Gln His Ser Glu Ile Thr Pro Ser Gln Asp
    290                 295                 300

Glu Glu Met Arg Asn Asn Lys Ala Ala Ser Lys Arg Val Ser Leu His
305                 310                 315                 320

Lys Asn Glu Ala Met Glu Pro Asn Asn Ile Leu Glu Glu Cys Thr Val
                325                 330                 335

Leu Lys Ser Leu Ser Ser Val Val Phe Asp Asp Pro Ile Asp Lys Leu
            340                 345                 350

Pro Glu Gly Cys Ser Ser Met Glu Thr Asn Ile Lys Ile Ser Ile Ala
        355                 360                 365

Glu Arg Ala Lys Pro Glu Met Ser Arg Met Val Pro Leu Ile His Ile
    370                 375                 380

Thr Phe Pro Val Asp Gly Ser Pro Lys Glu Pro Val Ile Ala Lys Pro
385                 390                 395                 400

Ser Leu Gln Thr Arg Lys Gly Thr Ile His Asn Asn His Ser Val Asn
                405                 410                 415

Ile Pro Val His Gln Glu Asn Asp Lys His Lys Met Asn Ser His Arg
            420                 425                 430

Ser Lys Leu Asp Ser Lys Thr Lys Thr Ser Lys Lys Thr Pro Gln Asn
        435                 440                 445
```

-continued

```
Phe Val Ile Ser Thr Glu Gly Pro Ile Lys Pro Thr Met His Lys Thr
    450                 455                 460

Ser Ile Lys Thr Gln Ile Phe Pro Ala Leu Gly Leu Val Asp Pro Arg
465                 470                 475                 480

Pro Trp Gln Leu Pro Arg Phe Gln Lys Lys Met Pro Gln Ile Ala Lys
                485                 490                 495

Lys Gln Ser Thr His Arg Thr Gln Lys Pro Lys Lys Gln Ser Phe Pro
            500                 505                 510

Cys Ile Cys Lys Asn Pro Gly Thr Gln Lys Ser Cys Val Pro Leu Ser
        515                 520                 525

Val Gln Pro Thr Glu Pro Arg Leu Asn Tyr Leu Asp Leu Lys Tyr Ser
    530                 535                 540

Asp Met Phe Lys Glu Ile Asn Ser Thr Ala Asn Gly Pro Gly Ile Tyr
545                 550                 555                 560

Glu Met Phe Gly Thr Pro Val Tyr Cys His Val Arg Glu Thr Glu Arg
                565                 570                 575

Asp Glu Asn Thr Tyr Tyr Arg Glu Ile Cys Ser Ala Pro Ser Gly Arg
            580                 585                 590

Arg Ile Thr Asn Lys Cys Arg Ser Ser His Ser Glu Arg Lys Ser Asn
        595                 600                 605

Ile Arg Thr Arg Leu Ser Gln Lys Lys Thr His Met Lys Cys Pro Lys
    610                 615                 620

Thr Ser Phe Gly Ile Lys Gln Glu His Lys Val Leu Ile Ser Lys Glu
625                 630                 635                 640

Lys Ser Ser Lys Ala Val His Ser Asn Leu His Asp Ile Glu Asn Gly
                645                 650                 655

Asp Gly Ile Ser Glu Pro Asp Trp Gln Ile Lys Ser Ser Gly Asn Glu
            660                 665                 670

Phe Leu Ser Ser Lys Asp Glu Ile His Pro Met Asn Leu Ala Gln Thr
        675                 680                 685

Pro Glu Gln Ser Met Lys Gln Asn Glu Phe Pro Pro Val Ser Asp Leu
    690                 695                 700

Ser Ile Val Glu Glu Val Ser Met Glu Glu Ser Thr Gly Asp Arg Asp
705                 710                 715                 720

Ile Ser Asn Asn Gln Ile Leu Thr Thr Ser Leu Arg Asp Leu Gln Glu
                725                 730                 735

Leu Glu Glu Leu His His Gln Ile Pro Phe Ile Pro Ser Glu Asp Ser
            740                 745                 750

Trp Ala Val Pro Ser Glu Lys Asn Ser Asn Lys Tyr Val Gln Gln Glu
        755                 760                 765

Lys Gln Asn Thr Ala Ser Leu Ser Lys Val Asn Ala Ser Arg Ile Leu
    770                 775                 780

Thr Asn Asp Leu Glu Phe Asp Ser Val Ser Asp His Ser Lys Thr Leu
785                 790                 795                 800

Thr Asn Phe Ser Phe Gln Ala Lys Gln Glu Ser Ala Ser Ser Gln Thr
                805                 810                 815

Tyr Gln Tyr Trp Val His Tyr Leu Asp His Asp Ser Leu Ala Asn Lys
            820                 825                 830

Ser Ile Thr Tyr Gln Met Phe Gly Lys Thr Leu Ser Gly Thr Asn Ser
        835                 840                 845

Ile Ser Gln Glu Ile Met Asp Ser Val Asn Asn Glu Glu Leu Thr Asp
    850                 855                 860
```

-continued

```
Glu Leu Leu Gly Cys Leu Ala Ala Glu Leu Leu Ala Leu Asp Glu Lys
865                 870                 875                 880

Asp Asn Asn Ser Cys Gln Lys Met Ala Asn Glu Thr Asp Pro Glu Asn
                885                 890                 895

Leu Asn Leu Val Leu Arg Trp Arg Gly Ser Thr Pro Lys Glu Met Gly
            900                 905                 910

Arg Glu Thr Thr Lys Val Lys Ile Gln Arg His Ser Ser Gly Leu Arg
        915                 920                 925

Ile Tyr Asp Arg Glu Glu Lys Phe Leu Ile Ser Asn Glu Lys Lys Ile
    930                 935                 940

Phe Ser Glu Asn Ser Leu Lys Ser Glu Glu Pro Ile Leu Trp Thr Lys
945                 950                 955                 960

Gly Glu Ile Leu Gly Lys Gly Ala Tyr Gly Thr Val Tyr Cys Gly Leu
                965                 970                 975

Thr Ser Gln Gly Gln Leu Ile Ala Val Lys Gln Val Ala Leu Asp Thr
            980                 985                 990

Ser Asn Lys Leu Ala Ala Glu Lys Glu Tyr Arg Lys Leu Gln Glu Glu
        995                 1000                1005

Val Asp Leu Leu Lys Ala Leu Lys His Val Asn Ile Val Ala Tyr Leu
    1010                1015                1020

Gly Thr Cys Leu Gln Glu Asn Thr Val Ser Ile Phe Met Glu Phe Val
1025                1030                1035                1040

Pro Gly Gly Ser Ile Ser Ser Ile Ile Asn Arg Phe Gly Pro Leu Pro
                1045                1050                1055

Glu Met Val Phe Cys Lys Tyr Thr Lys Gln Ile Leu Gln Gly Val Ala
            1060                1065                1070

Tyr Leu His Glu Asn Cys Val Val His Arg Asp Ile Lys Gly Asn Asn
        1075                1080                1085

Val Met Leu Met Pro Thr Gly Ile Ile Lys Leu Ile Asp Phe Gly Cys
    1090                1095                1100

Ala Arg Arg Leu Ala Trp Ala Gly Leu Asn Gly Thr His Ser Asp Met
1105                1110                1115                1120

Leu Lys Ser Met His Gly Thr Pro Tyr Trp Met Ala Pro Glu Val Ile
                1125                1130                1135

Asn Glu Ser Gly Tyr Gly Arg Lys Ser Asp Ile Trp Ser Ile Gly Cys
            1140                1145                1150

Thr Val Phe Glu Met Ala Thr Gly Lys Pro Pro Leu Ala Ser Met Asp
        1155                1160                1165

Arg Met Ala Ala Met Phe Tyr Ile Gly Ala His Arg Gly Leu Met Pro
    1170                1175                1180

Pro Leu Pro Asp His Phe Ser Glu Asn Ala Ala Asp Phe Val Arg Met
1185                1190                1195                1200

Cys Leu Thr Arg Asp Gln His Glu Arg Pro Ser Ala Leu Gln Leu Leu
                1205                1210                1215

Lys His Ser Phe Leu Glu Arg Ser His
            1220                1225


<210> SEQ ID NO 8
<211> LENGTH: 1080
<212> TYPE: PRT
<213> ORGANISM: Homo sapiens

<400> SEQUENCE: 8

Phe Asp Gln Asp Gly Asp Cys Ser His Ser Thr Leu Val Asn Glu Glu
 1               5                  10                  15
```

-continued

```
Glu Asp Pro Ser Gly Gly Arg Gln Asp Trp Gln Pro Arg Thr Glu Gly
            20                  25                  30

Val Glu Ile Thr Val Thr Phe Pro Arg Asp Val Ser Pro Pro Gln Glu
        35                  40                  45

Met Ser Gln Glu Asp Leu Lys Glu Lys Asn Leu Ile Asn Ser Ser Leu
    50                  55                  60

Gln Glu Trp Ala Gln Ala His Ala Val Ser His Pro Asn Glu Ile Glu
65                  70                  75                  80

Thr Val Glu Leu Arg Lys Lys Lys Leu Thr Met Arg Pro Leu Val Leu
                85                  90                  95

Gln Lys Glu Glu Ser Ser Arg Glu Leu Cys Asn Val Asn Leu Gly Phe
            100                 105                 110

Leu Leu Pro Arg Ser Cys Leu Glu Leu Asn Ile Ser Lys Ser Val Thr
        115                 120                 125

Arg Glu Asp Ala Pro His Phe Leu Lys Glu Gln Gln Arg Lys Ser Glu
    130                 135                 140

Glu Phe Ser Thr Ser His Met Lys Tyr Ser Gly Arg Ser Ile Lys Phe
145                 150                 155                 160

Leu Leu Pro Pro Leu Ser Leu Leu Pro Thr Arg Ser Gly Val Leu Thr
                165                 170                 175

Ile Pro Gln Asn His Lys Phe Pro Lys Glu Lys Glu Arg Asn Ile Pro
            180                 185                 190

Ser Leu Thr Ser Phe Val Pro Lys Leu Ser Val Ser Val Arg Gln Ser
        195                 200                 205

Asp Glu Leu Ser Pro Ser Asn Glu Pro Pro Gly Ala Leu Val Lys Ser
    210                 215                 220

Leu Met Asp Pro Thr Leu Arg Ser Ser Asp Gly Phe Ile Trp Ser Arg
225                 230                 235                 240

Asn Met Cys Ser Phe Pro Lys Thr Asn His His Arg Gln Cys Leu Glu
                245                 250                 255

Lys Glu Glu Asn Trp Lys Ser Lys Glu Ile Glu Glu Cys Asn Lys Ile
            260                 265                 270

Glu Ile Thr His Phe Glu Lys Gly Gln Ser Leu Val Ser Phe Glu Asn
        275                 280                 285

Leu Lys Glu Gly Asn Ile Pro Ala Val Arg Glu Glu Asp Ile Asp Cys
    290                 295                 300

His Gly Ser Lys Thr Arg Lys Pro Glu Glu Glu Asn Ser Gln Tyr Leu
305                 310                 315                 320

Ser Ser Arg Lys Asn Glu Ser Ser Val Ala Lys Asn Tyr Glu Gln Asp
                325                 330                 335

Pro Glu Ile Val Cys Thr Ile Pro Ser Lys Phe Gln Glu Thr Gln His
            340                 345                 350

Ser Glu Ile Thr Pro Ser Gln Asp Glu Glu Met Arg Asn Asn Lys Ala
        355                 360                 365

Ala Ser Lys Arg Val Ser Leu His Lys Asn Glu Ala Met Glu Pro Asn
    370                 375                 380

Asn Ile Leu Glu Glu Cys Thr Val Leu Lys Ser Leu Ser Ser Val Val
385                 390                 395                 400

Phe Asp Asp Pro Ile Asp Lys Leu Pro Glu Gly Cys Ser Ser Met Glu
                405                 410                 415

Thr Asn Ile Lys Ile Ser Ile Ala Glu Arg Ala Lys Pro Glu Met Ser
            420                 425                 430
```

-continued

```
Arg Met Val Pro Leu Ile His Ile Thr Phe Pro Val Asp Gly Ser Pro
        435                 440                 445

Lys Glu Pro Val Ile Ala Lys Pro Ser Leu Gln Thr Arg Lys Gly Thr
    450                 455                 460

Ile His Asn Asn His Ser Val Asn Ile Pro Val His Gln Glu Asn Asp
465                 470                 475                 480

Lys His Lys Met Asn Ser His Arg Ser Lys Leu Asp Ser Lys Thr Lys
                485                 490                 495

Thr Ser Lys Lys Thr Pro Gln Asn Phe Val Ile Ser Thr Glu Gly Pro
            500                 505                 510

Ile Lys Pro Thr Met His Lys Thr Ser Ile Lys Thr Gln Ile Phe Pro
        515                 520                 525

Ala Leu Gly Leu Val Asp Pro Arg Pro Trp Gln Leu Pro Arg Phe Gln
    530                 535                 540

Lys Lys Met Pro Gln Ile Ala Lys Lys Gln Ser Thr His Arg Thr Gln
545                 550                 555                 560

Lys Pro Lys Lys Gln Ser Phe Pro Cys Ile Cys Lys Asn Pro Gly Thr
                565                 570                 575

Gln Lys Ser Cys Val Pro Leu Ser Val Gln Pro Thr Glu Pro Arg Leu
            580                 585                 590

Asn Tyr Leu Asp Leu Lys Tyr Ser Asp Met Phe Lys Glu Ile Asn Ser
        595                 600                 605

Thr Ala Asn Gly Pro Gly Ile Tyr Glu Met Phe Gly Thr Pro Val Tyr
    610                 615                 620

Cys His Val Arg Glu Thr Glu Arg Asp Glu Asn Thr Tyr Tyr Arg Glu
625                 630                 635                 640

Ile Cys Ser Ala Pro Ser Gly Arg Arg Ile Thr Asn Lys Cys Arg Ser
                645                 650                 655

Ser His Ser Glu Arg Lys Ser Asn Ile Arg Thr Arg Leu Ser Gln Lys
            660                 665                 670

Lys Thr His Met Lys Cys Pro Lys Thr Ser Phe Gly Ile Lys Gln Glu
        675                 680                 685

His Lys Val Leu Ile Ser Lys Glu Lys Ser Ser Lys Ala Val His Ser
    690                 695                 700

Asn Leu His Asp Ile Glu Asn Gly Asp Gly Ile Ser Glu Pro Asp Trp
705                 710                 715                 720

Gln Ile Lys Ser Ser Gly Asn Glu Phe Leu Ser Ser Lys Asp Glu Ile
                725                 730                 735

His Pro Met Asn Leu Ala Gln Thr Pro Glu Gln Ser Met Lys Gln Asn
            740                 745                 750

Glu Phe Pro Pro Val Ser Asp Leu Ser Ile Val Glu Glu Val Ser Met
        755                 760                 765

Glu Glu Ser Thr Gly Asp Arg Asp Ile Ser Asn Asn Gln Ile Leu Thr
    770                 775                 780

Thr Ser Leu Arg Asp Leu Gln Glu Leu Glu Glu Leu His His Gln Ile
785                 790                 795                 800

Pro Phe Ile Pro Ser Glu Asp Ser Trp Ala Val Pro Ser Glu Lys Asn
                805                 810                 815

Ser Asn Lys Tyr Val Gln Gln Glu Lys Gln Asn Thr Ala Ser Leu Ser
            820                 825                 830

Lys Val Asn Ala Ser Arg Ile Leu Thr Asn Asp Leu Glu Phe Asp Ser
        835                 840                 845

Val Ser Asp His Ser Lys Thr Leu Thr Asn Phe Ser Phe Gln Ala Lys
```

-continued

```
    850                 855                 860

Gln Glu Ser Ala Ser Ser Gln Thr Tyr Gln Tyr Trp Val His Tyr Leu
865                 870                 875                 880

Asp His Asp Ser Leu Ala Asn Lys Ser Ile Thr Tyr Gln Met Phe Gly
                885                 890                 895

Lys Thr Leu Ser Gly Thr Asn Ser Ile Ser Gln Glu Ile Met Asp Ser
            900                 905                 910

Val Asn Asn Glu Glu Leu Thr Asp Glu Leu Leu Gly Cys Leu Ala Ala
        915                 920                 925

Glu Leu Leu Ala Leu Asp Glu Lys Asp Asn Asn Ser Cys Gln Lys Met
    930                 935                 940

Ala Asn Glu Thr Asp Pro Glu Asn Leu Asn Leu Val Leu Arg Trp Arg
945                 950                 955                 960

Gly Ser Thr Pro Lys Glu Met Gly Arg Glu Thr Thr Lys Val Lys Ile
                965                 970                 975

Gln Arg His Ser Ser Gly Leu Arg Ile Tyr Asp Arg Glu Glu Lys Phe
            980                 985                 990

Leu Ile Ser Asn Glu Lys Lys Ile Phe Ser Glu Asn Ser Leu Lys Ser
        995                 1000                1005

Glu Glu Pro Ile Leu Trp Thr Lys Gly Glu Ile Leu Gly Lys Gly Ala
    1010                1015                1020

Tyr Gly Thr Val Tyr Cys Gly Leu Thr Ser Gln Gly Gln Leu Ile Ala
1025                1030                1035                1040

Val Lys Gln Val Ala Leu Asp Thr Ser Asn Lys Leu Ala Ala Glu Lys
                1045                1050                1055

Glu Tyr Arg Lys Leu Gln Glu Glu Val Asp Leu Leu Lys Ala Leu Lys
            1060                1065                1070

His Val Pro Asp Gln Gly Pro Ala
        1075                1080


<210> SEQ ID NO 9
<211> LENGTH: 1137
<212> TYPE: PRT
<213> ORGANISM: Homo sapiens

<400> SEQUENCE: 9

Ser Lys Lys Gln Gln Leu Leu Asp Ile Leu Met Ser Ser Met Pro Lys
 1               5                  10                  15

Pro Glu Arg His Ala Glu Ser Leu Leu Asp Ile Cys His Asp Thr Asn
            20                  25                  30

Ser Ser Pro Thr Asp Leu Met Thr Val Thr Lys Asn Gln Asn Ile Ile
        35                  40                  45

Leu Gln Ser Ile Ser Arg Ser Glu Glu Phe Asp Gln Asp Gly Asp Cys
    50                  55                  60

Ser His Ser Thr Leu Val Asn Glu Glu Glu Asp Pro Ser Gly Gly Arg
65                  70                  75                  80

Gln Asp Trp Gln Pro Arg Thr Glu Gly Val Glu Ile Thr Val Thr Phe
                85                  90                  95

Pro Arg Asp Val Ser Pro Pro Gln Glu Met Ser Gln Glu Asp Leu Lys
            100                 105                 110

Glu Lys Asn Leu Ile Asn Ser Ser Leu Gln Glu Trp Ala Gln Ala His
        115                 120                 125

Ala Val Ser His Pro Asn Glu Ile Glu Thr Val Glu Leu Arg Lys Lys
    130                 135                 140
```

-continued

```
Lys Leu Thr Met Arg Pro Leu Val Leu Gln Lys Glu Glu Ser Ser Arg
145                 150                 155                 160

Glu Leu Cys Asn Val Asn Leu Gly Phe Leu Leu Pro Arg Ser Cys Leu
                165                 170                 175

Glu Leu Asn Ile Ser Lys Ser Val Thr Arg Glu Asp Ala Pro His Phe
            180                 185                 190

Leu Lys Glu Gln Gln Arg Lys Ser Glu Glu Phe Ser Thr Ser His Met
        195                 200                 205

Lys Tyr Ser Gly Arg Ser Ile Lys Phe Leu Leu Pro Pro Leu Ser Leu
    210                 215                 220

Leu Pro Thr Arg Ser Gly Val Leu Thr Ile Pro Gln Asn His Lys Phe
225                 230                 235                 240

Pro Lys Glu Lys Glu Arg Asn Ile Pro Ser Leu Thr Ser Phe Val Pro
                245                 250                 255

Lys Leu Ser Val Ser Val Arg Gln Ser Asp Glu Leu Ser Pro Ser Asn
            260                 265                 270

Glu Pro Pro Gly Ala Leu Val Lys Ser Leu Met Asp Pro Thr Leu Arg
        275                 280                 285

Ser Ser Asp Gly Phe Ile Trp Ser Arg Asn Met Cys Ser Phe Pro Lys
    290                 295                 300

Thr Asn His His Arg Gln Cys Leu Glu Lys Glu Glu Asn Trp Lys Ser
305                 310                 315                 320

Lys Glu Ile Glu Glu Cys Asn Lys Ile Glu Ile Thr His Phe Glu Lys
                325                 330                 335

Gly Gln Ser Leu Val Ser Phe Glu Asn Leu Lys Glu Gly Asn Ile Pro
            340                 345                 350

Ala Val Arg Glu Glu Asp Ile Asp Cys His Gly Ser Lys Thr Arg Lys
        355                 360                 365

Pro Glu Glu Glu Asn Ser Gln Tyr Leu Ser Ser Arg Lys Asn Glu Ser
    370                 375                 380

Ser Val Ala Lys Asn Tyr Glu Gln Asp Pro Glu Ile Val Cys Thr Ile
385                 390                 395                 400

Pro Ser Lys Phe Gln Glu Thr Gln His Ser Glu Ile Thr Pro Ser Gln
                405                 410                 415

Asp Glu Glu Met Arg Asn Asn Lys Ala Ala Ser Lys Arg Val Ser Leu
            420                 425                 430

His Lys Asn Glu Ala Met Glu Pro Asn Asn Ile Leu Glu Glu Cys Thr
        435                 440                 445

Val Leu Lys Ser Leu Ser Ser Val Val Phe Asp Asp Pro Ile Asp Lys
    450                 455                 460

Leu Pro Glu Gly Cys Ser Ser Met Glu Thr Asn Ile Lys Ile Ser Ile
465                 470                 475                 480

Ala Glu Arg Ala Lys Pro Glu Met Ser Arg Met Val Pro Leu Ile His
                485                 490                 495

Ile Thr Phe Pro Val Asp Gly Ser Pro Lys Glu Pro Val Ile Ala Lys
            500                 505                 510

Pro Ser Leu Gln Thr Arg Lys Gly Thr Ile His Asn Asn His Ser Val
        515                 520                 525

Asn Ile Pro Val His Gln Glu Asn Asp Lys His Lys Met Asn Ser His
    530                 535                 540

Arg Ser Lys Leu Asp Ser Lys Thr Lys Thr Ser Lys Lys Thr Pro Gln
545                 550                 555                 560

Asn Phe Val Ile Ser Thr Glu Gly Pro Ile Lys Pro Thr Met His Lys
```

-continued

```
                565                 570                 575

Thr Ser Ile Lys Thr Gln Ile Phe Pro Ala Leu Gly Leu Val Asp Pro
            580                 585                 590

Arg Pro Trp Gln Leu Pro Arg Phe Gln Lys Lys Met Pro Gln Ile Ala
        595                 600                 605

Lys Lys Gln Ser Thr His Arg Thr Gln Lys Pro Lys Lys Gln Ser Phe
    610                 615                 620

Pro Cys Ile Cys Lys Asn Pro Gly Thr Gln Lys Ser Cys Val Pro Leu
625                 630                 635                 640

Ser Val Gln Pro Thr Glu Pro Arg Leu Asn Tyr Leu Asp Leu Lys Tyr
                645                 650                 655

Ser Asp Met Phe Lys Glu Ile Asn Ser Thr Ala Asn Gly Pro Gly Ile
            660                 665                 670

Tyr Glu Met Phe Gly Thr Pro Val Tyr Cys His Val Arg Glu Thr Glu
        675                 680                 685

Arg Asp Glu Asn Thr Tyr Tyr Arg Glu Ile Cys Ser Ala Pro Ser Gly
    690                 695                 700

Arg Arg Ile Thr Asn Lys Cys Arg Ser Ser His Ser Glu Arg Lys Ser
705                 710                 715                 720

Asn Ile Arg Thr Arg Leu Ser Gln Lys Lys Thr His Met Lys Cys Pro
                725                 730                 735

Lys Thr Ser Phe Gly Ile Lys Gln Glu His Lys Val Leu Ile Ser Lys
            740                 745                 750

Glu Lys Ser Ser Lys Ala Val His Ser Asn Leu His Asp Ile Glu Asn
        755                 760                 765

Gly Asp Gly Ile Ser Glu Pro Asp Trp Gln Ile Lys Ser Ser Gly Asn
    770                 775                 780

Glu Phe Leu Ser Ser Lys Asp Glu Ile His Pro Met Asn Leu Ala Gln
785                 790                 795                 800

Thr Pro Glu Gln Ser Met Lys Gln Asn Glu Phe Pro Pro Val Ser Asp
                805                 810                 815

Leu Ser Ile Val Glu Glu Val Ser Met Glu Glu Ser Thr Gly Asp Arg
            820                 825                 830

Asp Ile Ser Asn Asn Gln Ile Leu Thr Thr Ser Leu Arg Asp Leu Gln
        835                 840                 845

Glu Leu Glu Glu Leu His His Gln Ile Pro Phe Ile Pro Ser Glu Asp
    850                 855                 860

Ser Trp Ala Val Pro Ser Glu Lys Asn Ser Asn Lys Tyr Val Gln Gln
865                 870                 875                 880

Glu Lys Gln Asn Thr Ala Ser Leu Ser Lys Val Asn Ala Ser Arg Ile
                885                 890                 895

Leu Thr Asn Asp Leu Glu Phe Asp Ser Val Ser Asp His Ser Lys Thr
            900                 905                 910

Leu Thr Asn Phe Ser Phe Gln Ala Lys Gln Glu Ser Ala Ser Ser Gln
        915                 920                 925

Thr Tyr Gln Tyr Trp Val His Tyr Leu Asp His Asp Ser Leu Ala Asn
    930                 935                 940

Lys Ser Ile Thr Tyr Gln Met Phe Gly Lys Thr Leu Ser Gly Thr Asn
945                 950                 955                 960

Ser Ile Ser Gln Glu Ile Met Asp Ser Val Asn Asn Glu Glu Leu Thr
                965                 970                 975

Asp Glu Leu Leu Gly Cys Leu Ala Ala Glu Leu Leu Ala Leu Asp Glu
            980                 985                 990
```

-continued

```
Lys Asp Asn Asn Ser Cys Gln Lys Met Ala Asn Glu Thr Asp Pro Glu
        995                 1000                1005

Asn Leu Asn Leu Val Leu Arg Trp Arg Gly Ser Thr Pro Lys Glu Met
    1010                1015                1020

Gly Arg Glu Thr Thr Lys Val Lys Ile Gln Arg His Ser Ser Gly Leu
1025                1030                1035                1040

Arg Ile Tyr Asp Arg Glu Glu Lys Phe Leu Ile Ser Asn Glu Lys Lys
                1045                1050                1055

Ile Phe Ser Glu Asn Ser Leu Lys Ser Glu Glu Pro Ile Leu Trp Thr
            1060                1065                1070

Lys Gly Glu Ile Leu Gly Lys Gly Ala Tyr Gly Thr Val Tyr Cys Gly
        1075                1080                1085

Leu Thr Ser Gln Gly Gln Leu Ile Ala Val Lys Gln Val Ala Leu Asp
    1090                1095                1100

Thr Ser Asn Lys Leu Ala Ala Glu Lys Glu Tyr Arg Lys Leu Gln Glu
1105                1110                1115                1120

Glu Val Asp Leu Leu Lys Ala Leu Lys His Val Pro Asp Gln Gly Pro
                1125                1130                1135

Ala


<210> SEQ ID NO 10
<211> LENGTH: 1338
<212> TYPE: PRT
<213> ORGANISM: Homo sapiens

<400> SEQUENCE: 10

Ser Lys Lys Gln Gln Leu Leu Asp Ile Leu Met Ser Ser Met Pro Lys
 1               5                  10                  15

Pro Glu Arg His Ala Glu Ser Leu Leu Asp Ile Cys His Asp Thr Asn
            20                  25                  30

Ser Ser Pro Thr Asp Leu Met Thr Val Thr Lys Asn Gln Asn Ile Ile
        35                  40                  45

Leu Gln Ser Ile Ser Arg Ser Glu Glu Phe Asp Gln Asp Gly Asp Cys
    50                  55                  60

Ser His Ser Thr Leu Val Asn Glu Glu Glu Asp Pro Ser Gly Gly Arg
65                  70                  75                  80

Gln Asp Trp Gln Pro Arg Thr Glu Gly Val Glu Ile Thr Val Thr Phe
                85                  90                  95

Pro Arg Asp Val Ser Pro Pro Gln Glu Met Ser Gln Glu Asp Leu Lys
            100                 105                 110

Glu Lys Asn Leu Ile Asn Ser Ser Leu Gln Glu Trp Ala Gln Ala His
        115                 120                 125

Ala Val Ser His Pro Asn Glu Ile Glu Thr Val Glu Leu Arg Lys Lys
    130                 135                 140

Lys Leu Thr Met Arg Pro Leu Val Leu Gln Lys Glu Glu Ser Ser Arg
145                 150                 155                 160

Glu Leu Cys Asn Val Asn Leu Gly Phe Leu Leu Pro Arg Ser Cys Leu
                165                 170                 175

Glu Leu Asn Ile Ser Lys Ser Val Thr Arg Glu Asp Ala Pro His Phe
            180                 185                 190

Leu Lys Glu Gln Gln Arg Lys Ser Glu Glu Phe Ser Thr Ser His Met
        195                 200                 205

Lys Tyr Ser Gly Arg Ser Ile Lys Phe Leu Leu Pro Pro Leu Ser Leu
    210                 215                 220
```

-continued

```
Leu Pro Thr Arg Ser Gly Val Leu Thr Ile Pro Gln Asn His Lys Phe
225                 230                 235                 240

Pro Lys Glu Lys Glu Arg Asn Ile Pro Ser Leu Thr Ser Phe Val Pro
                245                 250                 255

Lys Leu Ser Val Ser Val Arg Gln Ser Asp Glu Leu Ser Pro Ser Asn
            260                 265                 270

Glu Pro Pro Gly Ala Leu Val Lys Ser Leu Met Asp Pro Thr Leu Arg
        275                 280                 285

Ser Ser Asp Gly Phe Ile Trp Ser Arg Asn Met Cys Ser Phe Pro Lys
    290                 295                 300

Thr Asn His His Arg Gln Cys Leu Glu Lys Glu Glu Asn Trp Lys Ser
305                 310                 315                 320

Lys Glu Ile Glu Glu Cys Asn Lys Ile Glu Ile Thr His Phe Glu Lys
                325                 330                 335

Gly Gln Ser Leu Val Ser Phe Glu Asn Leu Lys Glu Gly Asn Ile Pro
            340                 345                 350

Ala Val Arg Glu Glu Asp Ile Asp Cys His Gly Ser Lys Thr Arg Lys
        355                 360                 365

Pro Glu Glu Glu Asn Ser Gln Tyr Leu Ser Ser Arg Lys Asn Glu Ser
    370                 375                 380

Ser Val Ala Lys Asn Tyr Glu Gln Asp Pro Glu Ile Val Cys Thr Ile
385                 390                 395                 400

Pro Ser Lys Phe Gln Glu Thr Gln His Ser Glu Ile Thr Pro Ser Gln
                405                 410                 415

Asp Glu Glu Met Arg Asn Asn Lys Ala Ala Ser Lys Arg Val Ser Leu
            420                 425                 430

His Lys Asn Glu Ala Met Glu Pro Asn Asn Ile Leu Glu Glu Cys Thr
        435                 440                 445

Val Leu Lys Ser Leu Ser Ser Val Val Phe Asp Asp Pro Ile Asp Lys
    450                 455                 460

Leu Pro Glu Gly Cys Ser Ser Met Glu Thr Asn Ile Lys Ile Ser Ile
465                 470                 475                 480

Ala Glu Arg Ala Lys Pro Glu Met Ser Arg Met Val Pro Leu Ile His
                485                 490                 495

Ile Thr Phe Pro Val Asp Gly Ser Pro Lys Glu Pro Val Ile Ala Lys
            500                 505                 510

Pro Ser Leu Gln Thr Arg Lys Gly Thr Ile His Asn Asn His Ser Val
        515                 520                 525

Asn Ile Pro Val His Gln Glu Asn Asp Lys His Lys Met Asn Ser His
    530                 535                 540

Arg Ser Lys Leu Asp Ser Lys Thr Lys Thr Ser Lys Lys Thr Pro Gln
545                 550                 555                 560

Asn Phe Val Ile Ser Thr Glu Gly Pro Ile Lys Pro Thr Met His Lys
                565                 570                 575

Thr Ser Ile Lys Thr Gln Ile Phe Pro Ala Leu Gly Leu Val Asp Pro
            580                 585                 590

Arg Pro Trp Gln Leu Pro Arg Phe Gln Lys Lys Met Pro Gln Ile Ala
        595                 600                 605

Lys Lys Gln Ser Thr His Arg Thr Gln Lys Pro Lys Lys Gln Ser Phe
    610                 615                 620

Pro Cys Ile Cys Lys Asn Pro Gly Thr Gln Lys Ser Cys Val Pro Leu
625                 630                 635                 640
```

-continued

```
Ser Val Gln Pro Thr Glu Pro Arg Leu Asn Tyr Leu Asp Leu Lys Tyr
                645                 650                 655

Ser Asp Met Phe Lys Glu Ile Asn Ser Thr Ala Asn Gly Pro Gly Ile
            660                 665                 670

Tyr Glu Met Phe Gly Thr Pro Val Tyr Cys His Val Arg Glu Thr Glu
        675                 680                 685

Arg Asp Glu Asn Thr Tyr Tyr Arg Glu Ile Cys Ser Ala Pro Ser Gly
    690                 695                 700

Arg Arg Ile Thr Asn Lys Cys Arg Ser Ser His Ser Glu Arg Lys Ser
705                 710                 715                 720

Asn Ile Arg Thr Arg Leu Ser Gln Lys Lys Thr His Met Lys Cys Pro
                725                 730                 735

Lys Thr Ser Phe Gly Ile Lys Gln Glu His Lys Val Leu Ile Ser Lys
            740                 745                 750

Glu Lys Ser Ser Lys Ala Val His Ser Asn Leu His Asp Ile Glu Asn
        755                 760                 765

Gly Asp Gly Ile Ser Glu Pro Asp Trp Gln Ile Lys Ser Ser Gly Asn
    770                 775                 780

Glu Phe Leu Ser Ser Lys Asp Glu Ile His Pro Met Asn Leu Ala Gln
785                 790                 795                 800

Thr Pro Glu Gln Ser Met Lys Gln Asn Glu Phe Pro Pro Val Ser Asp
                805                 810                 815

Leu Ser Ile Val Glu Glu Val Ser Met Glu Glu Ser Thr Gly Asp Arg
            820                 825                 830

Asp Ile Ser Asn Asn Gln Ile Leu Thr Thr Ser Leu Arg Asp Leu Gln
        835                 840                 845

Glu Leu Glu Glu Leu His His Gln Ile Pro Phe Ile Pro Ser Glu Asp
    850                 855                 860

Ser Trp Ala Val Pro Ser Glu Lys Asn Ser Asn Lys Tyr Val Gln Gln
865                 870                 875                 880

Glu Lys Gln Asn Thr Ala Ser Leu Ser Lys Val Asn Ala Ser Arg Ile
                885                 890                 895

Leu Thr Asn Asp Leu Glu Phe Asp Ser Val Ser Asp His Ser Lys Thr
            900                 905                 910

Leu Thr Asn Phe Ser Phe Gln Ala Lys Gln Glu Ser Ala Ser Ser Gln
        915                 920                 925

Thr Tyr Gln Tyr Trp Val His Tyr Leu Asp His Asp Ser Leu Ala Asn
    930                 935                 940

Lys Ser Ile Thr Tyr Gln Met Phe Gly Lys Thr Leu Ser Gly Thr Asn
945                 950                 955                 960

Ser Ile Ser Gln Glu Ile Met Asp Ser Val Asn Asn Glu Glu Leu Thr
                965                 970                 975

Asp Glu Leu Leu Gly Cys Leu Ala Ala Glu Leu Leu Ala Leu Asp Glu
            980                 985                 990

Lys Asp Asn Asn Ser Cys Gln Lys Met Ala Asn Glu Thr Asp Pro Glu
        995                 1000                1005

Asn Leu Asn Leu Val Leu Arg Trp Arg Gly Ser Thr Pro Lys Glu Met
    1010                1015                1020

Gly Arg Glu Thr Thr Lys Val Lys Ile Gln Arg His Ser Ser Gly Leu
1025                1030                1035                1040

Arg Ile Tyr Asp Arg Glu Glu Lys Phe Leu Ile Ser Asn Glu Lys Lys
                1045                1050                1055

Ile Phe Ser Glu Asn Ser Leu Lys Ser Glu Glu Pro Ile Leu Trp Thr
```

-continued

```
            1060                1065                1070

Lys Gly Glu Ile Leu Gly Lys Gly Ala Tyr Gly Thr Val Tyr Cys Gly
        1075                1080                1085

Leu Thr Ser Gln Gly Gln Leu Ile Ala Val Lys Gln Val Ala Leu Asp
    1090                1095                1100

Thr Ser Asn Lys Leu Ala Ala Glu Lys Glu Tyr Arg Lys Leu Gln Glu
1105                1110                1115                1120

Glu Val Asp Leu Leu Lys Ala Leu Lys His Val Asn Ile Val Ala Tyr
                1125                1130                1135

Leu Gly Thr Cys Leu Gln Glu Asn Thr Val Ser Ile Phe Met Glu Phe
            1140                1145                1150

Val Pro Gly Gly Ser Ile Ser Ser Ile Ile Asn Arg Phe Gly Pro Leu
        1155                1160                1165

Pro Glu Met Val Phe Cys Lys Tyr Thr Lys Gln Ile Leu Gln Gly Val
    1170                1175                1180

Ala Tyr Leu His Glu Asn Cys Val Val His Arg Asp Ile Lys Gly Asn
1185                1190                1195                1200

Asn Val Met Leu Met Pro Thr Gly Ile Ile Lys Leu Ile Asp Phe Gly
                1205                1210                1215

Cys Ala Arg Arg Leu Ala Trp Ala Gly Leu Asn Gly Thr His Ser Asp
            1220                1225                1230

Met Leu Lys Ser Met His Gly Thr Pro Tyr Trp Met Ala Pro Glu Val
        1235                1240                1245

Ile Asn Glu Ser Gly Tyr Gly Arg Lys Ser Asp Ile Trp Ser Ile Gly
    1250                1255                1260

Cys Thr Val Phe Glu Met Ala Thr Gly Lys Pro Pro Leu Ala Ser Met
1265                1270                1275                1280

Asp Arg Met Ala Ala Met Phe Tyr Ile Gly Ala His Arg Gly Leu Met
                1285                1290                1295

Pro Pro Leu Pro Asp His Phe Ser Glu Asn Ala Ala Asp Phe Val Arg
            1300                1305                1310

Met Cys Leu Thr Arg Asp Gln His Glu Arg Pro Ser Ala Leu Gln Leu
        1315                1320                1325

Leu Lys His Ser Phe Leu Glu Arg Ser His
    1330                1335


<210> SEQ ID NO 11
<211> LENGTH: 472
<212> TYPE: PRT
<213> ORGANISM: Homo sapiens

<400> SEQUENCE: 11

Ser Lys Lys Gln Gln Leu Leu Asp Ile Leu Met Ser Ser Met Pro Lys
 1               5                  10                  15

Pro Glu Arg His Ala Glu Ser Leu Leu Asp Ile Cys His Asp Thr Asn
            20                  25                  30

Ser Ser Pro Thr Asp Leu Met Thr Val Thr Lys Asn Gln Asn Ile Ile
        35                  40                  45

Leu Gln Ser Ile Ser Arg Ser Glu Glu Phe Asp Gln Asp Gly Asp Cys
    50                  55                  60

Ser His Ser Thr Leu Val Asn Glu Glu Glu Asp Pro Ser Gly Gly Arg
65                  70                  75                  80

Gln Asp Trp Gln Pro Arg Thr Glu Gly Val Glu Ile Thr Val Thr Phe
                85                  90                  95
```

-continued

```
Pro Arg Asp Val Ser Pro Pro Gln Glu Met Ser Gln Glu Asp Leu Lys
            100                 105                 110

Glu Lys Asn Leu Ile Asn Ser Ser Leu Gln Glu Trp Ala Gln Ala His
        115                 120                 125

Ala Val Ser His Pro Asn Glu Ile Glu Thr Val Glu Leu Arg Lys Lys
    130                 135                 140

Lys Leu Thr Met Arg Pro Leu Val Leu Gln Lys Glu Glu Ser Ser Arg
145                 150                 155                 160

Glu Leu Cys Asn Val Asn Leu Gly Phe Leu Leu Pro Arg Ser Cys Leu
                165                 170                 175

Glu Leu Asn Ile Ser Lys Ser Val Thr Arg Glu Asp Ala Pro His Phe
            180                 185                 190

Leu Lys Glu Gln Gln Arg Lys Ser Glu Glu Phe Ser Thr Ser His Met
        195                 200                 205

Lys Tyr Ser Gly Arg Ser Ile Lys Arg His Ser Ser Gly Leu Arg Ile
    210                 215                 220

Tyr Asp Arg Glu Glu Lys Phe Leu Ile Ser Asn Glu Lys Lys Ile Phe
225                 230                 235                 240

Ser Glu Asn Ser Leu Lys Ser Glu Glu Pro Ile Leu Trp Thr Lys Val
                245                 250                 255

Asp Leu Leu Lys Ala Leu Lys His Val Asn Ile Val Ala Tyr Leu Gly
            260                 265                 270

Thr Cys Leu Gln Glu Asn Thr Val Ser Ile Phe Met Glu Phe Val Pro
        275                 280                 285

Gly Gly Ser Ile Ser Ser Ile Ile Asn Arg Phe Gly Pro Leu Pro Glu
    290                 295                 300

Met Val Phe Cys Lys Tyr Thr Lys Gln Ile Leu Gln Gly Val Ala Tyr
305                 310                 315                 320

Leu His Glu Asn Cys Val Val His Arg Asp Ile Lys Gly Asn Asn Val
                325                 330                 335

Met Leu Met Pro Thr Gly Ile Ile Lys Leu Ile Asp Phe Gly Cys Ala
            340                 345                 350

Arg Arg Leu Ala Trp Ala Gly Leu Asn Gly Thr His Ser Asp Met Leu
        355                 360                 365

Lys Ser Met His Gly Thr Pro Tyr Trp Met Ala Pro Glu Val Ile Asn
    370                 375                 380

Glu Ser Gly Tyr Gly Arg Lys Ser Asp Ile Trp Ser Ile Gly Cys Thr
385                 390                 395                 400

Val Phe Glu Met Ala Thr Gly Lys Pro Pro Leu Ala Ser Met Asp Arg
                405                 410                 415

Met Ala Ala Met Phe Tyr Ile Gly Ala His Arg Gly Leu Met Pro Pro
            420                 425                 430

Leu Pro Asp His Phe Ser Glu Asn Ala Ala Asp Phe Val Arg Met Cys
        435                 440                 445

Leu Thr Arg Asp Gln His Glu Arg Pro Ser Ala Leu Gln Leu Leu Lys
    450                 455                 460

His Ser Phe Leu Glu Arg Ser His
465                 470
```

```
<210> SEQ ID NO 12
<211> LENGTH: 520
<212> TYPE: PRT
<213> ORGANISM: Homo sapiens

<400> SEQUENCE: 12
```

-continued

```
Ser Lys Lys Gln Gln Leu Leu Asp Ile Leu Met Ser Ser Met Pro Lys
 1               5                  10                  15

Pro Glu Arg His Ala Glu Ser Leu Leu Asp Ile Cys His Asp Thr Asn
            20                  25                  30

Ser Ser Pro Thr Asp Leu Met Thr Val Thr Lys Asn Gln Asn Ile Ile
        35                  40                  45

Leu Gln Ser Ile Ser Arg Ser Glu Glu Phe Asp Gln Asp Gly Asp Cys
    50                  55                  60

Ser His Ser Thr Leu Val Asn Glu Glu Glu Asp Pro Ser Gly Gly Arg
65                  70                  75                  80

Gln Asp Trp Gln Pro Arg Thr Glu Gly Val Glu Ile Thr Val Thr Phe
                85                  90                  95

Pro Arg Asp Val Ser Pro Pro Gln Glu Met Ser Gln Glu Asp Leu Lys
            100                 105                 110

Glu Lys Asn Leu Ile Asn Ser Ser Leu Gln Glu Trp Ala Gln Ala His
        115                 120                 125

Ala Val Ser His Pro Asn Glu Ile Glu Thr Val Glu Leu Arg Lys Lys
    130                 135                 140

Lys Leu Thr Met Arg Pro Leu Val Leu Gln Lys Glu Glu Ser Ser Arg
145                 150                 155                 160

Glu Leu Cys Asn Val Asn Leu Gly Phe Leu Leu Pro Arg Ser Cys Leu
                165                 170                 175

Glu Leu Asn Ile Ser Lys Ser Val Thr Arg Glu Asp Ala Pro His Phe
            180                 185                 190

Leu Lys Glu Gln Gln Arg Lys Ser Glu Glu Phe Ser Thr Ser His Met
        195                 200                 205

Lys Tyr Ser Gly Arg Ser Ile Lys Arg His Ser Ser Gly Leu Arg Ile
    210                 215                 220

Tyr Asp Arg Glu Glu Lys Phe Leu Ile Ser Asn Glu Lys Lys Ile Phe
225                 230                 235                 240

Ser Glu Asn Ser Leu Lys Ser Glu Glu Pro Ile Leu Trp Thr Lys Gly
                245                 250                 255

Glu Ile Leu Gly Lys Gly Ala Tyr Gly Thr Val Tyr Cys Gly Leu Thr
            260                 265                 270

Ser Gln Gly Gln Leu Ile Ala Val Lys Gln Val Ala Leu Asp Thr Ser
        275                 280                 285

Asn Lys Leu Ala Ala Glu Lys Glu Tyr Arg Lys Leu Gln Glu Glu Val
    290                 295                 300

Asp Leu Leu Lys Ala Leu Lys His Val Asn Ile Val Ala Tyr Leu Gly
305                 310                 315                 320

Thr Cys Leu Gln Glu Asn Thr Val Ser Ile Phe Met Glu Phe Val Pro
                325                 330                 335

Gly Gly Ser Ile Ser Ser Ile Ile Asn Arg Phe Gly Pro Leu Pro Glu
            340                 345                 350

Met Val Phe Cys Lys Tyr Thr Lys Gln Ile Leu Gln Gly Val Ala Tyr
        355                 360                 365

Leu His Glu Asn Cys Val Val His Arg Asp Ile Lys Gly Asn Asn Val
    370                 375                 380

Met Leu Met Pro Thr Gly Ile Ile Lys Leu Ile Asp Phe Gly Cys Ala
385                 390                 395                 400

Arg Arg Leu Ala Trp Ala Gly Leu Asn Gly Thr His Ser Asp Met Leu
                405                 410                 415
```

```
Lys Ser Met His Gly Thr Pro Tyr Trp Met Ala Pro Glu Val Ile Asn
            420                 425                 430

Glu Ser Gly Tyr Gly Arg Lys Ser Asp Ile Trp Ser Ile Gly Cys Thr
        435                 440                 445

Val Phe Glu Met Ala Thr Gly Lys Pro Pro Leu Ala Ser Met Asp Arg
    450                 455                 460

Met Ala Ala Met Phe Tyr Ile Gly Ala His Arg Gly Leu Met Pro Pro
465                 470                 475                 480

Leu Pro Asp His Phe Ser Glu Asn Ala Ala Asp Phe Val Arg Met Cys
                485                 490                 495

Leu Thr Arg Asp Gln His Glu Arg Pro Ser Ala Leu Gln Leu Leu Lys
            500                 505                 510

His Ser Phe Leu Glu Arg Ser His
        515                 520


<210> SEQ ID NO 13
<211> LENGTH: 24
<212> TYPE: DNA
<213> ORGANISM: Homo sapiens
<220> FEATURE:
<221> NAME/KEY: misc_feature
<222> LOCATION: (1)...(24)

<400> SEQUENCE: 13

aatggcaccc acagtgacat gctt                                            24


<210> SEQ ID NO 14
<211> LENGTH: 24
<212> TYPE: DNA
<213> ORGANISM: Homo sapiens
<220> FEATURE:
<221> NAME/KEY: misc_feature
<222> LOCATION: (1)...(24)
<223> OTHER INFORMATION: Primer

<400> SEQUENCE: 14

ccctcggtgt gctccgatgt aaaa                                            24


<210> SEQ ID NO 15
<211> LENGTH: 28
<212> TYPE: DNA
<213> ORGANISM: Homo sapiens
<220> FEATURE:
<221> NAME/KEY: misc_feature
<222> LOCATION: (1)...(28)
<223> OTHER INFORMATION: Primer

<400> SEQUENCE: 15

ttcaaagaaa cagcagcttt tggacatt                                        28


<210> SEQ ID NO 16
<211> LENGTH: 25
<212> TYPE: DNA
<213> ORGANISM: Homo sapiens
<220> FEATURE:
<221> NAME/KEY: misc_feature
<222> LOCATION: (1)...(25)

<400> SEQUENCE: 16

gcatctgcag tggaactggg aagaa                                           25
```